US010759793B2

(12) United States Patent
Esteve Trias et al.

(10) Patent No.: US 10,759,793 B2
(45) Date of Patent: Sep. 1, 2020

(54) 2-(PYRAZOLOPYRIDIN-3-YL)PYRIMIDINE DERIVATIVES AS JAK INHIBITORS

(71) Applicant: ALMIRALL, S.A., Barcelona (ES)

(72) Inventors: Cristina Esteve Trias, Barcelona (ES); Joan Taltavull Moll, Barcelona (ES); Jacob Gonzalez Rodriguez, Barcelona (ES); Bernat Vidal Juan, Barcelona (ES)

(73) Assignee: Almirall, S.A., Barcelona (ES)

( * ) Notice: Subject to any disclaimer, the term of this patent is extended or adjusted under 35 U.S.C. 154(b) by 0 days.

(21) Appl. No.: 15/735,235

(22) PCT Filed: Jun. 10, 2016

(86) PCT No.: PCT/EP2016/063391
§ 371 (c)(1),
(2) Date: Dec. 11, 2017

(87) PCT Pub. No.: WO2016/198663
PCT Pub. Date: Dec. 15, 2016

(65) Prior Publication Data
US 2018/0162856 A1 Jun. 14, 2018

(30) Foreign Application Priority Data
Jun. 11, 2015 (EP) .................................. 15382305

(51) Int. Cl.
*C07D 471/04* (2006.01)
*C07D 239/24* (2006.01)
(52) U.S. Cl.
CPC ......... *C07D 471/04* (2013.01); *C07D 239/24* (2013.01)

(58) Field of Classification Search
CPC ................................................... C07D 471/04
See application file for complete search history.

(56) References Cited

U.S. PATENT DOCUMENTS 9,206,183 B2 * 12/2015 Bach Tana ........... C07D 487/04

FOREIGN PATENT DOCUMENTS

| JP | 2013-515688 | 5/2013 |
| WO | WO 2011/076419 A1 | 6/2011 |
| WO | WO 2011/101161 A1 | 8/2011 |
| WO | WO 2013/025628 A1 | 2/2013 |
| WO | WO 2015/086693 A1 | 6/2015 |

OTHER PUBLICATIONS

Thoma "Selective inhibitors of the Janus kinase Jak3—Are they effective?" Bioorganic & Medicinal Chemistry Letters 24 (2014) 4617-4621.*
Lin "A Novel Selective JAK2 Inhibitor Identified Using Pharmacological Interactions" Frontiers in Pharmacology Dec. 2018 | vol. 9 | Article 1379 pp. 1-14.*
O'Shea "Janus kinase Inhibitors in autoimmune diseases" Ann Rheum Dis. Apr. 2013 ; 72(0 2): ii111-ii115.*
International Search Report for International Application No. PCT/EP2016/063391, dated Jul. 18, 2016.
Written Opinion of the International Search Authority for International Application No. PCT/EP2016/063391.

* cited by examiner

*Primary Examiner* — David K O'Dell
(74) *Attorney, Agent, or Firm* — Finnegan, Henderson, Farabow, Garrett & Dunner, LLP

(57) ABSTRACT

New 2-(pyrazolopyridin-3-yl)pyrimidine derivatives are disclosed; as well as processes for their preparation, pharmaceutical compositions comprising them, and their use in therapy as inhibitors of Janus Kinases (JAK).

13 Claims, No Drawings

2-(PYRAZOLOPYRIDIN-3-YL)PYRIMIDINE DERIVATIVES AS JAK INHIBITORS

This application is a national stage filing under 35 U.S.C. § 371 of International Application No. PCT/EP2016/063391, filed on Jun. 10, 2016, which claims priority of European Patent Application No. 15382305.9, filed Jun. 11, 2015. The contents of these applications are each incorporated herein by reference.

FIELD OF THE INVENTION

The present invention relates to novel compounds having JAK inhibitory activity. This invention also relates to pharmaceutical compositions containing them, processes for their preparation and their use in the treatment of several disorders.

BACKGROUND OF THE INVENTION

Cytokines have critical functions in regulating many aspects of immunity and inflammation, ranging from the development and differentiation of immune cells to the suppression of immune responses. Type I and type II cytokine receptors lack intrinsic enzymatic activity capable of mediating signal transduction, and thus require association with tyrosine kinases for this purpose. The JAK family of kinases comprises four different members, namely JAK1, JAK2, JAK3 and TYK2, which bind to type I and type II cytokine receptors for controlling signal transduction (Murray P J, (2007). The JAK-STAT signalling pathway: input and output integration. *J Immunol,* 178: 2623). Each of the JAK kinases is selective for the receptors of certain cytokines. In this regard, JAK-deficient cell lines and mice have validated the essential role of each JAK protein in receptor signalling: JAK1 in class II cytokine receptors (IFN and IL-10 family), those sharing the gp130 chain (IL-6 family) and the common gamma chain (IL-2, IL-4, IL-7, IL-9, IL-15 and IL-21) (Rodig et al. (1998). Disruption of the JAK1 gene demonstrates obligatory and nonredundant roles of the JAKs in cytokine-induced biological response. *Cell,* 93:373; Guschin et al. (1995). A major role for the protein tyrosine kinase JAK1 in the JAK/STAT signal transduction pathway in response to interleukin-6. *EMBO J.* 14: 1421; Briscoe et al. (1996). Kinase-negative mutants of JAK1 can sustain intereferon-gamma-inducible gene expression but not an antiviral state. *EMBO J.* 15:799); JAK2 in hematopoietic factors (Epo, Tpo, GM-CSF, IL-3, IL-5) and type II IFNs (Parganas et al., (1998). JAK2 is essential for signalling through a variety of cytokine receptors. *Cell,* 93:385); JAK3 in receptors sharing the common gamma chain (IL-2 family) (Park et al., (1995). Developmental defects of lymphoid cells in JAK3 kinase-deficient mice. *Immunity,* 3:771; Thomis et al., (1995). Defects in B lymphocyte maturation and T lymphocyte activation in mice lacking JAK3. *Science,* 270:794; Russell et al., (1995). Mutation of JAK3 in a partient with SCID: Essential role of JAK3 in lymphoid development. *Science,* 270:797); and Tyk2 in the receptors of IL-12, IL-23, IL-13 and type I IFNs (Karaghiosoff et al., (2000). Partial impairment of cytokine responses in Tyk2-deficient mice. *Immunity,* 13:549; Shimoda et al., (2000). Tyk2 plays a restricted role in IFNg signaling, although it is required for IL-12-mediated T cell function. *Immunity,* 13:561; Minegishi et al., (2006). Human Tyrosine kinase 2 deficiency reveals its requisite roles in multiple cytokine signals involved in innate and acquired immunity. *Immunity,* 25:745).

Receptor stimulation leads sequentially to JAK activation by phosphorylation, receptor phosphorylation, STAT protein recruitment and STAT activation and dimerization. The STAT dimer then functions as a transcription factor, trans-locating to the nucleus and activating the transcription of multiple response genes. There are seven STAT proteins identified: STAT1, STAT2, STAT3, STAT4, STAT5a, STAT5b and STAT6. Each particular cytokine receptor associates preferentially with a particular STAT protein. Some associations are independent of cell type (ex: IFNg-STAT1) while others may be cell type dependent (Murray P J, (2007). The JAK-STAT signaling pathway: input and output integration. *J Immunol,* 178: 2623).

The phenotype of deficient mice has provided insights on the function of each JAK and the cytokine receptors signaling through them. JAK3 associates exclusively with the common gamma chain of the receptors for IL-2, IL-4, IL-7, IL-9, IL-15 and IL-21 cytokines. By virtue of this exclusive association, JAK3 knock out mice and common gamma chain deficient mice have an identical phenotype (Thomis et al., (1995). Defects in B lymphocyte maturation and T lymphocyte activation in mice lacking JAK3. *Science,* 270: 794; DiSanto et al., (1995). Lymphoid development in mice with a targeted deletion of the interleukin 2 receptor gamma chain. *PNAS,* 92:377). Moreover, this phenotype is shared to a great extent with SCID patients that hold mutations/defects in the common gamma chain or JAK3 genes (O'Shea et al., (2004). JAK3 and the pathogenesis of severe combined immunodeficiency. *Mol Immunol,* 41: 727). JAK3-deficient mice are viable but display abnormal lymphopoiesis which leads to a reduced thymus size (10-100 fold smaller than wild type). JAK3-deficient peripheral T cells are unresponsive and have an activated/memory cell phenotype (Baird et al., (1998). T cell development and activation in JAK3-deficient mice. *J. Leuk. Biol.* 63: 669). The thymic defect in these mice strongly resembles that seen in IL-7 and IL-7 receptor knockout mice, suggesting that the absence of IL-7 signaling accounts for this defect in JAK3−/−mice (von Freeden-Jeffry et al., (1995). Lymphopenia in Interleukin (IL)-7 Gene-deleted Mice Identifies IL-7 as a non-redundant Cytokine. *J Exp Med,* 181:1519; Peschon et al, (1994). Early lymphocyte expansion is severely impaired in interleukin 7 receptor-deficient mice. *J Exp Med,* 180: 1955). These mice, like SCID humans, have no NK cells, probably due to the absence of IL-15 signaling, a survival factor for these cells. JAK3 knockout mice, unlike SCID patients, show deficient B cell lymphopoiesis while in human patients, B cells are present in circulation but are not responsive leading to hypoglobulinemia (O'Shea et al., (2004). JAK3 and the pathogenesis of severe combined immunodeficiency. *Mol Immunol,* 41: 727). This is explained by species-specific differences in IL-7 function in B and T cell development in mice and humans. On the other hand, Grossman et al. (1999. Dysregulated myelopoiesis in mice lacking JAK3. *Blood,* 94:932:939) have shown that the loss of JAK3 in the T-cell compartment drives the expansion of the myeloid lineages leading to dysregulated myelopoiesis.

JAK2-deficient mice are embrionically lethal, due to the absence of definitive erythropoiesis. Myeloid progenitors fail to respond to Epo, Tpo, IL-3 or GM-CSF, while G-CSF and IL-6 signaling are not affected. JAK2 is not required for the generation, amplification or functional differentiation of lymphoid progenitors (Parganas et al., (1998). JAK2 is essential for signaling through a variety of cytokine receptors. *Cell,* 93:385).

JAK1-deficient mice die perinatally due to a nursing defect. JAK1 binds exclusively to the gp130 chain shared by the IL-6 cytokine family (i.e. LIF, CNTF, OSM, CT-1) and along with JAK3, is an essential component of the receptors sharing the common gamma chain, by binding to the non-shared receptor subunit. In this regard, JAK1-deficient mice show similar hematopoiesis defects as JAK3-deficient mice. In addition, they show defective responses to neurotrophic factors and to all interferons (class II cytokine receptors) (Rodig et al., (1998). Disruption of the JAK1 gene demonstrates obligatory and non-redundant roles of the JAKs in cytokine-induced biological response. *Cell*, 93:373).

Finally, Tyk2-deficient mice show an impaired response to IL-12 and IL-23 and only partially impaired to IFN-alpha (Karaghiosoff et al., (2000). Partial impairment of cytokine responses in Tyk2-deficient mice. *Immunity*, 13:549; Shimoda et al., (2000). Tyk2 plays a restricted role in IFNg signaling, although it is required for IL-12-mediated T cell function. *Immunity*, 13:561). However, human Tyk2 deficiency demonstrates that Tyk2 is involved in the signaling from IFN-α, IL-6, IL-10, IL-12 and IL-23 (Minegishi et al., (2006). Human Tyrosine kinase 2 deficiency reveals its requisite roles in multiple cytokine signals involved in innate and acquired immunity. *Immunity*, 25:745).

The role of JAK kinases in transducing the signal from a myriad of cytokines makes them potential targets for the treatment of diseases in which cytokines have a pathogenic role, such as dermatological diseases; respiratory diseases; allergic diseases; inflammatory or autoimmune-mediated; function disorders and neurological disorders; cardiovascular diseases; viral infection; metabolism/endocrine function disorders; neurological disorders and pain; bone marrow and organ transplant rejection; myelo-dysplastic syndrome; myeloproliferative disorders (MPDs); cancer and hematologic malignancies, leukemia, lymphomas and solid tumors.

In view of the numerous conditions that are contemplated to benefit by treatment involving modulation of the JAK pathway or of the JAK Kinases it is immediately apparent that new compounds that modulate JAK pathways and use of these compounds should provide substantial therapeutic benefits to a wide variety of patients.

Some substituted pyrimidines as Janus kinase inhibitors were described in WO 2013/025628 and WO 2011/101161.

Provided herein are novel 2-(pyrazolopyridin-3-yl)pyrimidine derivatives for use in the treatment of conditions in which targeting of the JAK pathway or inhibition of JAK kinases can be therapeutically useful.

The compounds described in the present invention are simultaneously potent JAK1, JAK2 and JAK3 inhibitors, i.e. pan-JAK inhibitors.

SUMMARY OF THE INVENTION

Thus the present invention is directed to a 2-(pyrazolopyridin-3-yl)pyrimidine derivative for use in the treatment of the human or animal body, which 2-(pyrazolopyridin-3-yl)pyrimidine derivative is a compound of formula (I), or a pharmaceutically acceptable salt, or solvate, or N-oxide, or stereoisomer or deuterated derivative thereof:

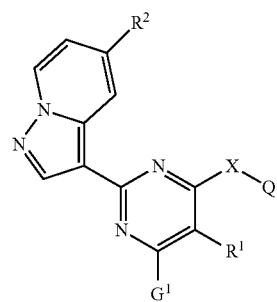

Formula (I)

wherein
X represents —O— or —NR$^3$— group,
R$^1$ and R$^2$ are independently selected from the group consisting of a hydrogen atom, a halogen atom, a linear or branched C$_{1-4}$ alkyl, a linear or branched C$_{1-4}$ alkoxy group and —CN group;
R$^3$ is selected from the group consisting of a hydrogen atom, a linear or branched C$_{1-4}$ alkyl group, a —(CH$_2$)$_{1-3}$NR'R" group and a —(CH$_2$)$_{1-3}$-pyrrolidine group;
G$^1$ is selected from the group consisting of —CN group, —CO—R$^a$ group, a —O—R$^6$ group, a —(CHR$^7$)$_m$—NR'R" group, a phenyl group, a monocyclic C$_{5-7}$ cycloalkyl group, a monocyclic 5- to 6-membered heteroaryl group containing at least one heteroatom selected from O, S and N and a monocyclic 5- to 6-membered heterocyclyl group containing at least one heteroatom selected from O, S and N, wherein the phenyl, cycloalkyl, heteroaryl and heterocyclyl groups are unsubstituted or substituted by one or more substituents selected from a halogen atom, a hydroxyl group, a linear or branched C$_{1-4}$ alkyl group, a linear or branched C$_{1-6}$-hydroxyalkyl group, a linear or branched C$_{1-4}$ alkoxy group, a —(CH$_2$)$_{0-2}$NR'R" group, —(CH$_2$)$_{0-2}$CN group and —CO—R$^a$ group, wherein R$^a$ represents a hydrogen atom, a hydroxyl group, a linear or branched C$_{1-3}$ alkyl group, a linear or branched C$_{1-3}$ alkoxy group or an amino group,
Q is selected from the group consisting of:

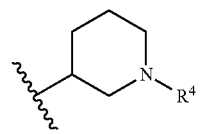

Q$_a$

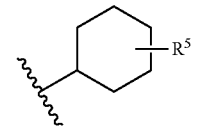

Q$_b$

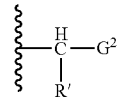

Q$_c$ wherein
R$^4$ is selected from the group consisting of a linear or branched C$_{1-4}$ alkyl group, —CO—R' group, —CO(CH$_2$)$_{1-2}$—OH group; —CO(CH$_2$)$_{1-2}$—CN group, —CO(CH$_2$)$_{1-2}$—CF$_3$ group, a cyanothiazole group, a monocyclic 4- to 6-membered heterocyclyl group containing at least one heteroatom selected from O, S and N and a monocyclic 5- to 6-membered heteroaryl group containing at least one heteroatom selected from O, S and N, wherein the heterocyclyl and heteroaryl group independently are unsubstituted or substituted with one or more substituents selected from —(CH$_2$)$_m$—CN group and a C$_{1-2}$ hydroxyalkyl group, R$^5$ represents a —(CH$_2$)$_m$—CN group or a —(CH$_2$)$_m$—OH group;

G$_2$ represents a phenyl group, a pyrimidine group or a pyridine group, wherein the phenyl, pyrimidine and pyridine groups are unsubstituted or substituted by one or more substituents selected from a halogen atom, a linear or branched C$_{1-4}$ alkyl group, a hydroxyl group, a —CN group, R$^6$ is selected from the group consisting of a hydrogen atom, —(CH$_2$)$_{(1-2)}$—CO—O—R''' group, a linear or branched (C$_{1-6}$ alkoxy)-(C$_{1-6}$ alkyl) group and a linear or branched C$_{1-6}$ alkyl group wherein said linear or branched C$_{1-6}$ alkyl group is unsubstituted or substituted with one or more substituents selected from a halogen atom, a hydroxyl group and —NR'R'' group, R$^7$ represents a hydrogen atom, a hydroxyl or a C$_{1-2}$ alkyl group, R' and R'' independently represents a hydrogen atom, a linear or branched C$_{1-3}$ alkyl group, a linear or branched C$_{1-3}$ hydroxyalkyl group, a linear or branched C$_{1-3}$ alkoxy group, R''' represents a C$_{1-2}$ alkyl group or a benzyl group, and m independently has a value from 0 to 3, wherein the 2-(pyrazolopyridin-3-yl)pyrimidine derivative is not:

3-{(3R)-3-[[2-(Dimethylamino)ethyl](5-fluoro-6-morpholin-4-yl-2-pyrazolo[1,5-a]pyridin-3-ylpyrimidin-4-yl)amino]piperidin-1-yl}-3-oxopropanenitrile 3-{(3R)-3-[(5-Fluoro-6-morpholin-4-yl-2-pyrazolo[1,5-a]pyridin-3-ylpyrimidin-4-yl) amino]piperidin-1-yl}-3-oxopropanenitrile (3-{(3R)-3-[(5-Fluoro-6-morpholin-4-yl-2-pyrazolo[1,5-a]pyridin-3-ylpyrimidin-4-yl)amino]piperidin-1-yl}oxetan-3-yl)acetonitrile Ethyl (3R)-3-[(5-fluoro-6-morpholin-4-yl-2-pyrazolo[1,5-a]pyridin-3-ylpyrimidin-4-yl)amino]piperidine-1-carboxylate 2-{(3R)-3-[(5-Fluoro-6-morpholin-4-yl-2-pyrazolo[1,5-a]pyridin-3-ylpyrimidin-4-yl)amino]piperidin-1-yl}-2-oxoethanol 3-[(3R)-3-({5-Fluoro-6-[4-(hydroxymethyl)piperidin-1-yl]-2-pyrazolo[1,5-a]pyridin-3-ylpyrimidin-4-yl}amino)piperidin-1-yl]-3-oxopropanenitrile 3-[(3R)-3-({5-Fluoro-6-[4-(hydroxymethyl)phenyl]-2-pyrazolo[1,5-a]pyridin-3-ylpyrimidin-4-yl}amino)piperidin-1-yl]-3-oxopropanenitrile 3-((3R)-3-{[5-Fluoro-6-(4-formylphenyl)-2-pyrazolo[1,5-a]pyridin-3-ylpyrimidin-4-yl]amino}piperidin-1-yl)-3-oxopropanenitrile 3-{(3R)-3-[(5-Fluoro-6-{3-hydroxy-4-[(methylamino)methyl]phenyl}-2-pyrazolo[1,5-a]pyridin-3-ylpyrimidin-4-yl)amino]piperidin-1-yl}-3-oxopropanenitrile 3-{(3R)-3-[(5-Fluoro-6-{4-hydroxy-3-[(methylamino)methyl]phenyl}-2-pyrazolo[1,5-a]pyridin-3-ylpyrimidin-4-yl)amino]piperidin-1-yl}-3-oxopropanenitrile The present invention also provides a 2-(pyrazolopyridin-3-yl)pyrimidine derivative, which 2-(pyrazolopyridin-3-yl)pyrimidine derivative is a compound of formula (I), or a pharmaceutically acceptable salt, or solvate, or N-oxide, or stereoisomer or deuterated derivative thereof:

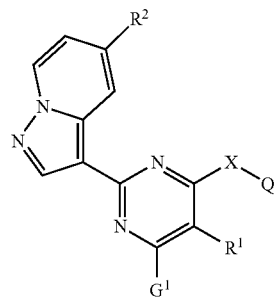

Formula (I)

wherein

X represents —O— or —NR$^3$— group,

R$^1$ and R$^2$ are independently selected from the group consisting of a hydrogen atom, a halogen atom, a linear or branched C$_{1-4}$ alkyl, a linear or branched C$_{1-4}$ alkoxy group and —CN group;

R$^3$ is selected from the group consisting of a hydrogen atom, a linear or branched C$_{1-4}$ alkyl group, a —(CH$_2$)$_{1-3}$NR'R'' group and a —(CH$_2$)$_{1-3}$-pyrrolidine group;

G$^1$ is selected from the group consisting of —CN group, —CO—R$^a$ group, a —O—R$^6$ group, a —(CHR$^7$)$_m$—NR'R'' group, a phenyl group, a monocyclic C$_{5-7}$ cycloalkyl group, a monocyclic 5- to 6-membered heteroaryl group containing at least one heteroatom selected from O, S and N and a monocyclic 5- to 6-membered heterocyclyl group containing at least one heteroatom selected from O, S and N, wherein the phenyl, cycloalkyl, heteroaryl and heterocyclyl groups are unsubstituted or substituted by one or more substituents selected from a halogen atom, a hydroxyl group, a linear or branched C$_{1-4}$ alkyl group, a linear or branched C$_{1-6}$-hydroxyalkyl group, a linear or branched C$_{1-4}$ alkoxy group, a —(CH$_2$)$_{0-2}$NR'R'' group, —(CH$_2$)$_{0-2}$CN group and —CO—R$^a$ group, wherein R$^a$ represents a hydrogen atom, a hydroxyl group, a linear or branched C$_{1-3}$ alkyl group, a linear or branched C$_{1-3}$ alkoxy group or an amino group, Q is selected from the group consisting of:

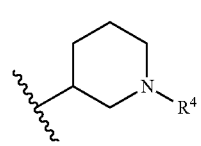

Q$_a$

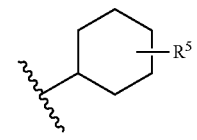

Q$_b$

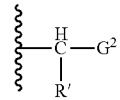

Q$_c$ wherein
R⁴ is selected from the group consisting of a linear or branched C$_{1-4}$ alkyl group, —CO—R' group, —CO(CH$_2$)$_{1-2}$—OH group; —CO(CH$_2$)$_{1-2}$—CN group, —CO(CH$_2$)$_{1-2}$—CF$_3$ group, a cyanothiazole group, a monocyclic 4- to 6-membered heterocyclyl group containing at least one heteroatom selected from O, S and N and a monocyclic 5- to 6-membered heteroaryl group containing at least one heteroatom selected from O, S and N, wherein the heterocyclyl and heteroaryl group independently are unsubstituted or substituted with one or more substituents selected from —(CH$_2$)$_m$—CN group and a C$_{1-2}$ hydroxyalkyl group, R⁵ represents a —(CH$_2$)$_m$—CN group or a —(CH$_2$)$_m$—OH group;

G² represents a phenyl group, a pyrimidine group or a pyridine group, wherein the phenyl, pyrimidine and pyridine groups are unsubstituted or substituted by one or more substituents selected from a halogen atom, a linear or branched C$_{1-4}$ alkyl group, a hydroxyl group, a —CN group, R⁶ is selected from the group consisting of a hydrogen atom, —(CH$_2$)$_{(0-2)}$—CO—O—R''' group, a linear or branched (C$_{1-6}$ alkoxy)-(C$_{1-6}$ alkyl) group and a linear or branched C$_{1-6}$ alkyl group wherein said linear or branched C$_{1-6}$ alkyl group is unsubstituted or substituted with one or more substituents selected from a halogen atom, a hydroxyl group and NR'R'' group, R⁷ represents a hydrogen atom, a hydroxyl or a C$_{1-2}$ alkyl group, R' and R'' independently represents a hydrogen atom, a linear or branched C$_{1-3}$ alkyl group, a linear or branched C$_{1-3}$ hydroxyalkyl group, a linear or branched C$_{1-3}$ alkoxy group, R''' represents a C$_{1-2}$ alkyl group or a benzyl group, and
m independently has a value from 0 to 3, wherein the 2-(pyrazolopyridin-3-yl)pyrimidine derivative is not:

3-{(3R)-3-[[2-(Dimethylamino)ethyl](5-fluoro-6-morpholin-4-yl-2-pyrazolo[1,5-a]pyridin-3-ylpyrimidin-4-yl)amino]piperidin-1-yl}-3-oxopropanenitrile 3-{(3R)-3-[(5-Fluoro-6-morpholin-4-yl-2-pyrazolo[1,5-a]pyridin-3-ylpyrimidin-4-yl)amino]piperidin-1-yl}-3-oxopropanenitrile (3-{(3R)-3-[(5-Fluoro-6-morpholin-4-yl-2-pyrazolo[1,5-a]pyridin-3-ylpyrimidin-4-yl)amino]piperidin-1-yl}oxetan-3-yl)acetonitrile Ethyl (3R)-3-[(5-fluoro-6-morpholin-4-yl-2-pyrazolo[1,5-a]pyridin-3-ylpyrimidin-4-yl)amino]piperidine-1-carboxylate 2-{(3R)-3-[(5-Fluoro-6-morpholin-4-yl-2-pyrazolo[1,5-a]pyridin-3-ylpyrimidin-4-yl)amino]piperidin-1-yl}-2-oxoethanol 3-[(3R)-3-({5-Fluoro-6-[4-(hydroxymethyl)piperidin-1-yl]-2-pyrazolo[1,5-a]pyridin-3-ylpyrimidin-4-yl}amino)piperidin-1-yl]-3-oxopropanenitrile 3-[(3R)-3-({5-Fluoro-6-[4-(hydroxymethyl)phenyl]-2-pyrazolo[1,5-a]pyridin-3-ylpyrimidin-4-yl}amino)piperidin-1-yl]-3-oxopropanenitrile 3-((3R)-3-{[5-Fluoro-6-(4-formylphenyl)-2-pyrazolo[1,5-a]pyridin-3-ylpyrimidin-4-yl]amino}piperidin-1-yl)-3-oxopropanenitrile 3-{(3R)-3-[(5-Fluoro-6-piperazin-1-yl-2-pyrazolo[1,5-a]pyridin-3-ylpyrimidin-4-yl)amino]piperidin-1-yl}-3-oxopropanenitrile 3-[(3R)-3-({6-[4-(Hydroxymethyl)phenyl]-5-methyl-2-pyrazolo[1,5-a]pyridin-3-ylpyrimidin-4-yl}amino)piperidin-1-yl]-3-oxopropanenitrile 3-((3R)-3-{[6-(4-Formylphenyl)-5-methyl-2-pyrazolo[1,5-a]pyridin-3-ylpyrimidin-4-yl]amino}piperidin-1-yl)-3-oxopropanenitrile 3-[(3R)-3-({5-Fluoro-6-[2-fluoro-4-(hydroxymethyl)phenyl]-2-pyrazolo[1,5-a]pyridin-3-ylpyrimidin-4-yl}amino)piperidin-1-yl]-3-oxopropanenitrile 3-((3R)-3-{[5-Fluoro-6-(2-fluoro-4-formylphenyl)-2-pyrazolo[1,5-a]pyridin-3-ylpyrimidin-4-yl]amino}piperidin-1-yl)-3-oxopropanenitrile 3-[(3R)-3-({5-Fluoro-6-[3-(hydroxymethyl)phenyl]-2-pyrazolo[1,5-a]pyridin-3-ylpyrimidin-4-yl}amino)piperidin-1-yl]-3-oxopropanenitrile 3-((3R)-3-{[5-Fluoro-6-(3-formylphenyl)-2-pyrazolo[1,5-a]pyridin-3-ylpyrimidin-4-yl]amino}piperidin-1-yl)-3-oxopropanenitrile 3-{(3R)-3-[(5-Fluoro-6-{3-hydroxy-4-[(methylamino)methyl]phenyl}-2-pyrazolo[1,5-a]pyridin-3-ylpyrimidin-4-yl)amino]piperidin-1-yl}-3-oxopropanenitrile 3-{(3R)-3-[(5-Fluoro-6-{4-hydroxy-3-[(methylamino)methyl]phenyl}-2-pyrazolo[1,5-a]pyridin-3-ylpyrimidin-4-yl)amino]piperidin-1-yl}-3-oxopropanenitrile (R)-3-(3-((5-Fluoro-6-(3-hydroxy-4-(hydroxymethyl)phenyl)-2-(pyrazolo[1,5-a]pyridin-3-yl)pyrimidin-4-yl)amino)piperidin-1-yl)-3-oxopropanenitrile (R)-3-(3-((5-Fluoro-6-(4-formyl-3-hydroxyphenyl)-2-(pyrazolo[1,5-a]pyridin-3-yl)pyrimidin-4-yl)amino)piperidin-1-yl)-3-oxopropanenitrile The invention further provides synthetic processes and intermediates described herein, which are useful for preparing said 2-(pyrazolopyridin-3-yl)pyrimidine derivatives.

The invention is also directed to a 2-(pyrazolopyridin-3-yl)pyrimidine derivative of the invention as described herein for use in the treatment of the human or animal body by therapy.

The invention also provides a pharmaceutical composition comprising the 2-(pyrazolopyridin-3-yl)pyrimidine derivatives of the invention and a pharmaceutically-acceptable diluent or carrier.

The invention is also directed to the 2-(pyrazolopyridin-3-yl)pyrimidine derivatives of the invention as described herein, for use in the treatment of a pathological condition or disease susceptible to amelioration by inhibition of Janus Kinases (JAK), in particular wherein the pathological condition or disease is selected from a dermatological disease, a respiratory disease, an allergic disease, an inflammatory or autoimmune-mediated disease, a function disorder, a neurological disorder, a cardiovascular disease, a viral infection, a metabolism/endocrine function disorder, a neurological disorder, pain, bone marrow and organ transplant rejection, myelo-dysplastic syndrome, a myeloproliferative disorder (MPDs), cancer, an hematologic malignancy, leukemia, lymphoma and solid tumor. More in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca.

The invention is also directed to use of the 2-(pyrazolopyridin-3-yl)pyrimidine derivatives of the invention as described herein, in the manufacture of a medicament for treatment of a pathological condition or disease susceptible to amelioration by inhibition of Janus Kinases (JAK), in particular wherein the pathological condition or disease is selected from a dermatological disease, a respiratory disease, an allergic disease, an inflammatory or autoimmune-mediated disease, a function disorder, a neurological disorder, a cardiovascular disease, a viral infection, a metabolism/endocrine function disorder, a neurological disorder, pain, bone marrow and organ transplant rejection, myelo-dysplastic syndrome, a myeloproliferative disorder (MPDs), cancer, an hematologic malignancy, leukemia, lymphoma and solid tumor. More in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Sézary syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca.

The invention also provides a method of treatment of a pathological condition or disease susceptible to amelioration by inhibition of Janus Kinases (JAK), in particular wherein the pathological condition or disease is selected from a dermatological disease, a respiratory disease, an allergic disease, an inflammatory or autoimmune-mediated disease, a function disorder, a neurological disorder, a cardiovascular disease, a viral infection, a metabolism/endocrine function disorder, a neurological disorder, pain, bone marrow and organ transplant rejection, myelo-dysplastic syndrome, a myeloproliferative disorder (MPDs), cancer, an hematologic malignancy, leukemia, lymphoma and solid tumor. More in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca.

The invention also provides a combination product comprising (i) the 2-(pyrazolopyridin-3-yl)pyrimidine derivatives of the invention as described herein; and (ii) one or more additional active substances.

DETAILED DESCRIPTION OF THE INVENTION

When describing the 2-(pyrazolopyridin-3-yl)pyrimidine derivatives, compositions, combinations and methods of the invention, the following terms have the following meanings, unless otherwise indicated.

As used herein the term $C_1$-$C_6$ alkyl embraces linear or branched radicals having 1 to 6 carbon atoms. Examples include methyl, ethyl, n-propyl, i-propyl, n-butyl, sec-butyl, t-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein the term $C_1$-$C_4$ alkyl embraces linear or branched radicals having 1 to 4 carbon atoms. Analogously, the term $C_1$-$C_3$ alkyl embraces linear or branched radicals having 1 to 3 carbon atoms and the term $C_1$-$C_2$ alkyl embraces linear or branched radicals having 1 to 2 carbon atoms.

As used herein, the term $C_1$-$C_6$ hydroxyalkyl embraces linear or branched alkyl radicals having 1 to 6 carbon atoms, any one of which may be substituted with one or more hydroxyl radicals. Examples of such radicals include hydroxymethyl, hydroxyethyl, hydroxypropyl, hydroxybutyl, hydroxypentyl and hydroxyhexyl.

As used herein, the term $C_1$-$C_3$ hydroxyalkyl embraces linear or branched alkyl radicals having 1 to 3 carbon atoms, any one of which may be substituted with one or more hydroxyl radicals. Examples of such radicals include hydroxymethyl, hydroxyethyl or hydroxypropyl.

As used herein, the term $C_1$-$C_2$ hydroxyalkyl embraces linear or branched alkyl radicals having 1 to 2 carbon atoms, any one of which may be substituted with one or more hydroxyl radicals. Examples of such radicals include hydroxymethyl or hydroxyethyl.

As used herein, the term $C_1$-$C_6$ alkoxy (or alkyloxy) embraces linear or branched oxy-containing radicals each having alkyl portions of 1 to 6 carbon atoms. Examples of $C_1$-$C_6$ alkoxy radicals include methoxy, ethoxy, n-propoxy, i-propoxy, n-butoxy, sec-butoxy, t-butoxy, n-pentoxy and n-hexoxy.

As used herein, the term $C_1$-$C_4$ alkoxy (or alkyloxy) embraces linear or branched oxy-containing radicals each having alkyl portions of 1 to 4 carbon atoms. Examples of $C_1$-$C_4$ alkoxy radicals include methoxy, ethoxy, n-propoxy, i-propoxy, n-butoxy, sec-butoxy or t-butoxy.

As used herein, the term $C_1$-$C_3$ alkoxy (or alkyloxy) embraces linear or branched oxy-containing radicals each having alkyl portions of 1 to 3 carbon atoms. Examples of $C_1$-$C_3$ alkoxy radicals include methoxy, ethoxy, n-propoxy and i-propoxy.

As used herein, the term ($C_{1-6}$alkoxy)-($C_{1-6}$alkyl) embraces linear or branched radicals having 1 to 6 carbon atoms substituted with a $C_{1-6}$ alkoxy group. Examples of ($C_{1-6}$ alkoxy)-($C_{1-6}$ alkyl) include methoxy-methyl, ethoxy-methyl, methoxy-ethyl, ethoxy-ethyl, methoxy-propyl, propoxy-methyl, ethoxy-propyl, propoxy-ethyl, propoxy-propyl, methoxy-butyl, ethoxy-butyl, methoxy-pentyl, ethoxy-pentyl and methoxy-hexyl.

As used herein, the term $C_{5-7}$ cycloalkyl embraces saturated monocyclic carbocyclic radicals having from 5 to 7 carbon atoms. Examples of monocyclic cycloalkyl groups include cyclopentyl, cyclohexyl and cycloheptyl.

As used herein, the term 5- to 6-membered heteroaryl radical embraces typically a 5- to 6-membered ring system comprising at least one heteroaromatic ring and containing at least one heteroatom selected from O, S and N.

Examples include pyridyl, pyrazinyl, pyrimidinyl, pyridazinyl, furyl, oxadiazolyl, pyrazolyl, oxazolyl, isoxazolyl, imidazolyl, thiazolyl, thiadiazolyl, thienyl or pyrrolyl.

As used herein, the term 4- to 6-membered heterocyclyl radical embraces typically a non-aromatic, saturated or unsaturated $C_{4-6}$ carbocyclic ring system in which one or more, for example 1, 2, 3 or 4 of the carbon atoms preferably 1 or 2 of the carbon atoms are replaced by a heteroatom selected from N, O and S. Examples of 4- to 6-membered heterocyclyl radicals include oxetanyl, azetidinyl, piperidyl, pyrrolidyl, pyrrolinyl, piperazinyl, morpholinyl, thiomorpholinyl, pyrrolyl, pyrazolinyl, pirazolidinyl, triazolyl, pyrazolyl, tetrazolyl, imidazolidinyl, 4,5-dihydro-oxazolyl, 1,3-dioxol-2-one, tetrahydrofuranyl, 3-aza-tetrahydrofuranyl, tetrahydrothiophenyl, tetrahydropyranyl, tetrahydrothiopyranyl or 1,4-azathianyl.

As used herein, the term 5- to 6-membered heterocyclyl radical embraces typically a non-aromatic, saturated or unsaturated $C_{5-6}$ carbocyclic ring system in which one or more, for example 1, 2, 3 or 4 of the carbon atoms preferably 1 or 2 of the carbon atoms are replaced by a heteroatom selected from N, O and S. Examples of 5- to 6-membered heterocyclyl radicals include piperidyl, pyrrolidyl, pyrrolinyl, piperazinyl, morpholinyl, thiomorpholinyl, pyrrolyl, pyrazolinyl, pirazolidinyl, triazolyl, pyrazolyl, tetrazolyl, imidazolidinyl, 4,5-dihydro-oxazolyl, 1,3-dioxol-2-one, tetrahydrofuranyl, 3-aza-tetrahydrofuranyl, tetrahydrothiophenyl, tetrahydropyranyl, tetrahydrothiopyranyl or 1,4-azathianyl.

As used herein, some of the atoms, radicals, moieties, chains and cycles present in the general structures of the invention are "unsubstituted or substituted". This means that these atoms, radicals, moieties, chains and cycles can be either unsubstituted or substituted in any position by one or more, for example 1, 2, 3 or 4, substituents, whereby the hydrogen atoms bound to the unsubstituted atoms, radicals, moieties, chains and cycles are replaced by chemically acceptable atoms, radicals, moieties, chains and cycles.

As used herein, the term halogen atom embraces chlorine, fluorine, bromine and iodine atoms. A halogen atom is typically a fluorine, chlorine or bromine atom. The term halo when used as a prefix has the same meaning.

Compounds containing one or more chiral centre may be used in enantiomerically or diastereoisomerically pure form, in the form of racemic mixtures and in the form of mixtures enriched in one or more stereoisomer. The scope of the invention as described and claimed encompasses the racemic forms of the compounds as well as the individual enantiomers, diastereomers, and stereoisomer-enriched mixtures.

Conventional techniques for the preparation/isolation of individual enantiomers include chiral synthesis from a suitable optically pure precursor or resolution of the racemate using, for example, chiral high pressure liquid chromatography (HPLC). Alternatively, the racemate (or a racemic precursor) may be reacted with a suitable optically active compound, for example, an alcohol, or, in the case where the compound contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to one skilled in the art. Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture. Stereoisomer conglomerates may be separated by conventional techniques known to those skilled in the art. See, e.g. "Stereochemistry of Organic Compounds" by Ernest L. Eliel (Wiley, New York, 1994).

As used herein, the term pharmaceutically acceptable salt refers to a salt prepared from a base or acid which is acceptable for administration to a patient, such as a mammal. Such salts can be derived from pharmaceutically-acceptable inorganic or organic bases and from pharmaceutically-acceptable inorganic or organic acids.

Pharmaceutically acceptable acids include both inorganic acids, for example hydrochloric, sulphuric, phosphoric, diphosphoric, hydrobromic, hydroiodic and nitric acid; and organic acids, for example citric, fumaric, gluconic, glutamic, lactic, maleic, malic, mandelic, mucic, ascorbic, oxalic, pantothenic, succinic, tartaric, benzoic, acetic, methanesulphonic, ethanesulphonic, benzenesulphonic, p-toluenesulphonic acid, xinafoic (1-hydroxy-2-naphthoic acid), napadisilic (1,5-naphthalenedisulfonic acid) and the like.

Salts derived from pharmaceutically-acceptable inorganic bases include aluminum, ammonium, calcium, copper, ferric, ferrous, lithium, magnesium, manganic, manganous, potassium, sodium, zinc and the like.

Salts derived from pharmaceutically-acceptable organic bases include salts of primary, secondary and tertiary amines, including alkyl amines, arylalkyl amines, heterocyclyl amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

Other salts according to the invention are quaternary ammonium compounds wherein an equivalent of an anion ($X^-$) is associated with the positive charge of the N atom. $X^-$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and p-toluenesulphonate.

As used herein, an N-oxide is formed from the tertiary basic amines or imines present in the molecule, using a convenient oxidising agent.

The 2-(pyrazolopyridin-3-yl)pyrimidine derivatives of the invention may exist in both unsolvated and solvated forms. The term solvate is used herein to describe a molecular complex comprising a compound of the invention and an amount of one or more pharmaceutically acceptable solvent molecules. The term hydrate is employed when said solvent is water. Examples of solvate forms include, but are not limited to, compounds of the invention in association with water, acetone, dichloromethane, 2-propanol, ethanol, methanol, dimethylsulfoxide (DMSO), ethyl acetate, acetic acid, ethanolamine, or mixtures thereof.

It is specifically contemplated that in the present invention one solvent molecule can be associated with one molecule of the compounds of the present invention, such as a hydrate. Furthermore, it is specifically contemplated that in the present invention, more than one solvent molecule may be associated with one molecule of the compounds of the present invention, such as a dihydrate. Additionally, it is specifically contemplated that in the present invention less than one solvent molecule may be associated with one molecule of the compounds of the present invention, such as a hemihydrate. Furthermore, solvates of the present invention are contemplated as solvates of compounds of the present invention that retain the biological effectiveness of the non-solvate form of the compounds.

The invention also includes isotopically-labeled 2-(pyrazolopyridin-3-yl)pyrimidine derivatives of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Preferred isotopically-labeled compounds include deuterated derivatives of the compounds of the invention. As used herein, the term deuterated derivative embraces compounds of the invention where in a particular position at least one hydrogen atom is replaced by deuterium. Deuterium (D or $^2$H) is a stable isotope of hydrogen which is present at a natural abundance of 0.015 molar %.

Isotopically-labeled 2-(pyrazolopyridin-3-yl)pyrimidine derivatives of the invention can generally be prepared by conventional techniques known to those skilled in the art or by processes analogous to those described herein, using an appropriate isotopically-labeled reagent in place of the non-labeled reagent otherwise employed.

Prodrugs of the 2-(pyrazolopyridin-3-yl)pyrimidine derivatives described herein are also within the scope of the invention. Thus certain derivatives of the 2-(pyrazolopyridin-3-yl)pyrimidine derivatives of the present invention, which derivatives may have little or no pharmacological activity themselves, when administered into or onto the body may be converted into compounds of the present invention having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of the present invention with certain moieties known to those skilled in the art as 'promoieties' as described, for example, in Design of Prodrugs by H. Bundgaard (Elsevier, 1985).

In the case of 2-(pyrazolopyridin-3-yl)pyrimidine derivatives that are solids, it is understood by those skilled in the art that the inventive compounds and salts may exist in different crystalline or polymorphic forms, or in an amorphous form, all of which are intended to be within the scope of the present invention.

Typically, $R^1$ represents a hydrogen atom, a fluorine atom, a chlorine atom or a methyl group, for example, a fluorine atom, a hydrogen atom or a methyl group. Preferably, $R^1$ represents a fluorine atom.

Typically, $R^2$ represents a hydrogen atom or a fluorine atom. Preferably, $R^2$ represents a hydrogen atom.

Typically, X represents a —$NR^3$— group. Alternatively, X may represent —O—.

Typically, $R^3$ represents a hydrogen atom.

Typically, Q represents Qa.

If $R^4$ is a —CO—R' group, then R' is typically not H.

Typically, $R^4$ represents a —$CO(CH_2)_{1-2}$—OH group or a —$CO(CH_2)_{1-2}$—CN group. Preferably, $R^4$ represents a —$C(O)CH_2OH$ group or a —$C(O)CH_2CN$ group.

Typically, $R^a$ represents a hydroxyl group, a linear or branched $C_{1-3}$ alkyl group, a linear or branched $C_{1-3}$ alkoxy group or an amino group.

Typically, $G^1$ represents a —O—$R^6$ group, a CN group or a monocyclic 5- to 6-membered heteroaryl group containing at least one heteroatom selected from O, S and N and being unsubstituted or substituted by one or more substituents selected from a halogen atom, a hydroxyl group, a linear or branched $C_{1-4}$ alkyl group, a linear or branched $C_{1-2}$ hydroxyalkyl group or a linear or branched $C_{1-4}$ alkoxy group. Preferably, $G^1$ represents a —O—$R^6$ group or a monocyclic 5- to 6-membered heteroaryl group containing at least one heteroatom selected from O, S and N and being unsubstituted or substituted by one or more substituents selected from a halogen atom, a linear or branched $C_{1-4}$ alkyl group or a linear or branched $C_{1-4}$ alkoxy group. For instance, $G^1$ may represent an O—$R^6$ group.

Typically, $R^6$ represents a linear or branched ($C_{1-6}$ alkoxy)-($C_{1-6}$ alkyl) group or a linear or branched $C_{1-6}$ alkyl group wherein said linear or branched $C_{1-6}$ alkyl group is unsubstituted or substituted with one or more substituents selected from a halogen atom and a hydroxyl group.

Typically, the 2-(pyrazolopyridin-3-yl)pyrimidine derivative is not:

3-{(3R)-3-[[2-(Dimethylamino)ethyl](5-fluoro-6-morpholin-4-yl-2-pyrazolo[1,5-a]pyridin-3-ylpyrimidin-4-yl)amino]piperidin-1-yl}-3-oxopropanenitrile 3-{(3R)-3-[(5-Fluoro-6-morpholin-4-yl-2-pyrazolo[1,5-a]pyridin-3-ylpyrimidin-4-yl)amino]piperidin-1-yl}-3-oxopropanenitrile (3-{(3R)-3-[(5-Fluoro-6-morpholin-4-yl-2-pyrazolo[1,5-a]pyridin-3-ylpyrimidin-4-yl)amino]piperidin-1-yl}oxetan-3-yl)acetonitrile Ethyl (3R)-3-[(5-fluoro-6-morpholin-4-yl-2-pyrazolo[1,5-a]pyridin-3-ylpyrimidin-4-yl)amino]piperidine-1-carboxylate 2-{(3R)-3-[(5-Fluoro-6-morpholin-4-yl-2-pyrazolo[1,5-a]pyridin-3-ylpyrimidin-4-yl)amino]piperidin-1-yl}-2-oxoethanol 3-[(3R)-3-({5-Fluoro-6-[4-(hydroxymethyl)piperidin-1-yl]-2-pyrazolo[1,5-a]pyridin-3-ylpyrimidin-4-yl}amino)piperidin-1-yl]-3-oxopropanenitrile 3-[(3R)-3-({5-Fluoro-6-[4-(hydroxymethyl)phenyl]-2-pyrazolo[1,5-a]pyridin-3-ylpyrimidin-4-yl}amino)piperidin-1-yl]-3-oxopropanenitrile 3-((3R)-3-{[5-Fluoro-6-(4-formylphenyl)-2-pyrazolo[1,5-a]pyridin-3-ylpyrimidin-4-yl]amino}piperidin-1-yl)-3-oxopropanenitrile 3-{(3R)-3-[(5-Fluoro-6-{3-hydroxy-4-[(methylamino)methyl]phenyl}-2-pyrazolo[1,5-a]pyridin-3-ylpyrimidin-4-yl)amino]piperidin-1-yl}-3-oxopropanenitrile
3-{(3R)-3-[(5-Fluoro-6-{4-hydroxy-3-[(methylamino)methyl]phenyl}-2-pyrazolo[1,5-a]pyridin-3-ylpyrimidin-4-yl)amino]piperidin-1-yl}-3-oxopropanenitrile or a pharmaceutically acceptable salt, or solvate, or N-oxide, or stereoisomer or deuterated derivative thereof.

Preferably, the 2-(pyrazolopyridin-3-yl)pyrimidine derivative is not:
3-{(3R)-3-[[2-(Dimethylamino)ethyl](5-fluoro-6-morpholin-4-yl-2-pyrazolo[1,5-a]pyridin-3-ylpyrimidin-4-yl)amino]piperidin-1-yl}-3-oxopropanenitrile
3-{(3R)-3-[(5-Fluoro-6-morpholin-4-yl-2-pyrazolo[1,5-a]pyridin-3-ylpyrimidin-4-yl)amino]piperidin-1-yl}-3-oxopropanenitrile
(3-{(3R)-3-[(5-Fluoro-6-morpholin-4-yl-2-pyrazolo[1,5-a]pyridin-3-ylpyrimidin-4-yl)amino]piperidin-1-yl}oxetan-3-yl)acetonitrile
Ethyl (3R)-3-[(5-fluoro-6-morpholin-4-yl-2-pyrazolo[1,5-a]pyridin-3-ylpyrimidin-4-yl)amino]piperidine-1-carboxylate
2-{(3R)-3-[(5-Fluoro-6-morpholin-4-yl-2-pyrazolo[1,5-a]pyridin-3-ylpyrimidin-4-yl)amino]piperidin-1-yl}-2-oxoethanol
3-[(3R)-3-({5-Fluoro-6-[4-(hydroxymethyl)piperidin-1-yl]-2-pyrazolo[1,5-a]pyridin-3-ylpyrimidin-4-yl}amino)piperidin-1-yl]-3-oxopropanenitrile
3-[(3R)-3-({5-Fluoro-6-[4-(hydroxymethyl)phenyl]-2-pyrazolo[1,5-a]pyridin-3-ylpyrimidin-4-yl}amino)piperidin-1-yl]-3-oxopropanenitrile
3-((3R)-3-{[5-Fluoro-6-(4-formylphenyl)-2-pyrazolo[1,5-a]pyridin-3-ylpyrimidin-4-yl]amino}piperidin-1-yl)-3-oxopropanenitrile
3-{(3R)-3-[(5-Fluoro-6-piperazin-1-yl-2-pyrazolo[1,5-a]pyridin-3-ylpyrimidin-4-yl)amino]piperidin-1-yl}-3-oxopropanenitrile
3-[(3R)-3-({6-[4-(Hydroxymethyl)phenyl]-5-methyl-2-pyrazolo[1,5-a]pyridin-3-ylpyrimidin-4-yl}amino)piperidin-1-yl]-3-oxopropanenitrile
3-((3R)-3-{[6-(4-Formylphenyl)-5-methyl-2-pyrazolo[1,5-a]pyridin-3-ylpyrimidin-4-yl]amino}piperidin-1-yl)-3-oxopropanenitrile
3-[(3R)-3-({5-Fluoro-6-[2-fluoro-4-(hydroxymethyl)phenyl]-2-pyrazolo[1,5-a]pyridin-3-ylpyrimidin-4-yl}amino)piperidin-1-yl]-3-oxopropanenitrile
3-((3R)-3-{[5-Fluoro-6-(2-fluoro-4-formylphenyl)-2-pyrazolo[1,5-a]pyridin-3-ylpyrimidin-4-yl]amino}piperidin-1-yl)-3-oxopropanenitrile
3-[(3R)-3-({5-Fluoro-6-[3-(hydroxymethyl)phenyl]-2-pyrazolo[1,5-a]pyridin-3-ylpyrimidin-4-yl}amino)piperidin-1-yl]-3-oxopropanenitrile
3-((3R)-3-{[5-Fluoro-6-(3-formylphenyl)-2-pyrazolo[1,5-a]pyridin-3-ylpyrimidin-4-yl]amino}piperidin-1-yl)-3-oxopropanenitrile
3-{(3R)-3-[(5-Fluoro-6-{3-hydroxy-4-[(methylamino)methyl]phenyl}-2-pyrazolo[1,5-a]pyridin-3-ylpyrimidin-4-yl)amino]piperidin-1-yl}-3-oxopropanenitrile
3-{(3R)-3-[(5-Fluoro-6-{4-hydroxy-3-[(methylamino)methyl]phenyl}-2-pyrazolo[1,5-a]pyridin-3-ylpyrimidin-4-yl)amino]piperidin-1-yl}-3-oxopropanenitrile
(R)-3-(3-((5-Fluoro-6-(3-hydroxy-4-(hydroxymethyl)phenyl)-2-(pyrazolo[1,5-a]pyridin-3-yl)pyrimidin-4-yl)amino)piperidin-1-yl)-3-oxopropanenitrile
(R)-3-(3-((5-Fluoro-6-(4-formyl-3-hydroxyphenyl)-2-(pyrazolo[1,5-a]pyridin-3-yl)pyrimidin-4-yl)amino)piperidin-1-yl)-3-oxopropanenitrile or a pharmaceutically acceptable salt, or solvate, or N-oxide, or stereoisomer or deuterated derivative thereof.

Preferably, the 2-(pyrazolopyridin-3-yl)pyrimidine derivative is not a compound of formula (I), wherein
X is $NR^3$;
$R^1$ is Me or F;
$R^2$ is H;
$R^3$ is H or $-CH_2CH_2N(CH_3)_2$;
$G^1$ is N-morpholino, 4-hydroxymethyl-N-piperidinyl, 4-hydroxymethyl-phenyl, 4-formyl-phenyl or phenyl substituted with hydroxyl and $-CH_2NHCH_3$;
Q is $Q^a$;
$R^4$ is $-C(O)CH_2CN$, $-C(O)CH_2OH$, $-C(O)OCH_2CH_3$, or oxetanyl substituted with $-CH_2CN$.

Preferably, the 2-(pyrazolopyridin-3-yl)pyrimidine derivative is not a compound of formula (I), wherein
X is $NR^3$;
$R^1$ is Me or F;
$R^2$ is H;
$R^3$ is H or $-CH_2CH_2N(CH_3)_2$;
$G^1$ is N-morpholino, 4-hydroxymethyl-N-piperidinyl, N-piperazinyl or phenyl, which phenyl is substituted with one or more, typically one or two, substituents independently selected from hydroxyl, fluoro, $-CH_2OH$, $-C(O)H$ and $-CH_2NHCH_3$;
Q is $Q^a$;
$R^4$ is $-C(O)CH_2CN$, $-C(O)CH_2OH$, $-C(O)OCH_2CH_3$, or oxetanyl substituted with $-CH_2CN$.

Typically, the 2-(pyrazolopyridin-3-yl)pyrimidine derivative is not a compound of formula (I), wherein
X is $NR^3$;
$R^1$ is Me or F;
$R^2$ is H;
$R^3$ is H or $-CH_2CH_2N(CH_3)_2$;
$G^1$ is N-morpholino, 4-hydroxymethyl-N-piperidinyl, 4-hydroxymethyl-phenyl, 4-formyl-phenyl or phenyl substituted with hydroxyl and $-CH_2NHCH_3$;
Q is $Q^a$;
$R^4$ is $-C(O)CH_2CN$, $-C(O)CH_2OH$, $-C(O)OCH_2CH_3$, or oxetanyl substituted with $-CH_2CN$ or a pharmaceutically acceptable salt, or solvate, or N-oxide, or stereoisomer or deuterated derivative thereof.

Typically, the 2-(pyrazolopyridin-3-yl)pyrimidine derivative is not a compound of formula (I), wherein
X is $NR^3$;
$R^1$ is Me or F;
$R^2$ is H;
$R^3$ is H or $-CH_2CH_2N(CH_3)_2$;
$G^1$ is N-morpholino, 4-hydroxymethyl-N-piperidinyl, N-piperazinyl or phenyl, which phenyl is substituted with one or more, typically one or two, substituents independently selected from hydroxyl, fluoro, $-CH_2OH$, $-C(O)H$ and $CH_2NHCH_3$;
Q is $Q^a$;
$R^4$ is $-C(O)CH_2CN$, $-C(O)CH_2OH$, $-C(O)OCH_2CH_3$, or oxetanyl substituted with $CH_2CN$;

or a pharmaceutically acceptable salt, or solvate, or N-oxide, or stereoisomer or deuterated derivative thereof.

It is particularly preferred that:
a. X represents —O—; or
b. X represents $-NR^3-$ and $R^3$ is selected from:
  i. a $-(CH_2)_{1-3}NR'R''$ group, wherein R' and R'' independently represents a linear or branched $C_{1-3}$ hydroxyalkyl group or a linear or branched $C_{1-3}$ alkoxy group; or ii. a —CH$_2$NR'R" group, wherein R' and R" independently represents a hydrogen atom, a linear or branched C$_{1-3}$ alkyl group, a linear or branched C$_{1-3}$ hydroxyalkyl group, a linear or branched C$_{1-3}$ alkoxy group; or iii. a CH$_2$-pyrollidine group; or c. R$^1$ is a linear or branched C$_{1-4}$ alkoxy group or a —CN group; or d. R$^2$ is a halogen atom or a —CN group; or e. G$^1$ is selected from the group consisting of CN group, —CO—R$^a$ group, a O—R$^6$ group, and a —(CHR$^7$)$_m$—NR'R" group; or f. G$^1$ is selected from a phenyl group, a monocyclic C$_{5-7}$ cycloalkyl group, a monocyclic 5- to 6-membered heteroaryl group containing at least one heteroatom selected from O, S and N and a monocyclic 5- to 6-membered heterocyclyl group containing at least one heteroatom selected from O, S and N, wherein the phenyl, cycloalkyl, heteroaryl and heterocyclyl groups are substituted by one or more substituents selected from a linear or branched C$_{3-6}$-hydroxyalkyl group, —(CH$_2$)$_{0-2}$CN group and —CO—R$^a$ group, wherein R$^a$ represents a hydroxyl group, a linear or branched C$_{1-3}$ alkyl group, a linear or branched C$_{1-3}$ alkoxy group or an amino group; or g. Q is Q$_a$ and R$^4$ is selected from the group consisting of a cyanothiazole group, and a monocyclic 5- to 6-membered heteroaryl group containing at least one heteroatom selected from O, S and N, wherein the heteroaryl group is unsubstituted or substituted with one or more substituents selected from (CH$_2$)$_m$—CN group and a C$_{1-2}$ hydroxyalkyl group; or h. Q is Q$_c$ and R' is a linear or branched C$_{1-3}$ hydroxyalkyl group or a linear or branched C$_{1-3}$ alkoxy group.

In a preferred embodiment,

R$^1$ represents a hydrogen atom, a fluorine atom, a chlorine atom or a methyl group, for example, a fluorine atom, a hydrogen atom or a methyl group, preferably a fluorine atom;

R$^2$ represents a hydrogen atom or a fluorine atom, preferably a hydrogen atom;

X represents a —O— or —NR$^3$— group, preferably a NR$^3$— group;

R$^3$ represents a hydrogen atom;

Q represents Qa;

R$^4$ represents a —CO(CH$_2$)$_{1-2}$—OH group or a —CO(CH$_2$)$_{1-2}$—CN group; preferably R$^4$ represents a —C(O)CH$_2$OH group or a —C(O)CH$_2$CN group;

G$^1$ represents a —O—R$^6$ group, a CN group or a monocyclic 5- to 6-membered heteroaryl group containing at least one heteroatom selected from O, S and N and being unsubstituted or substituted by one or more substituents selected from a halogen atom, a hydroxyl group, a linear or branched C$_{1-4}$ alkyl group, a linear or branched C$_{1-2}$ hydroxyalkyl group or a linear or branched C$_{1-4}$ alkoxy group, preferably G$^1$ represents a —O—R$^6$ group or a monocyclic 5- to 6-membered heteroaryl group containing at least one heteroatom selected from O, S and N and being unsubstituted or substituted by one or more substituents selected from a halogen atom, a linear or branched C$_{1-4}$ alkyl group or a linear or branched C$_{1-4}$ alkoxy group; and R$^6$ represents a linear or branched (C$_{1-6}$ alkoxy)-(C$_{1-6}$ alkyl) group or a linear or branched C$_{1-6}$ alkyl group wherein said linear or branched C$_{1-6}$ alkyl group is unsubstituted or substituted with one or more substituents selected from a halogen atom and a hydroxyl group.

In a more preferred embodiment,

X represents —O— or —NR$^3$— group,

R$^1$ and R$^2$ are independently selected from the group consisting of a hydrogen atom, a fluorine atom and a methyl group;

R$^3$ is selected from the group consisting of a hydrogen atom and a methyl group;

G$^1$ is selected from the group consisting of —CN group, a —CONH$_2$ group, a —CO$_2$Et group, a —CO$_2$'Pr group, a —O—R$^6$ group, a —NHCH$_2$CH$_2$OH group, a phenyl group, a pyridinyl group, a pyrazolyl group, a piperidinyl group, a piperazinyl group, a morpholinyl group, wherein the phenyl, pyridinyl, pyrazolyl, piperidinyl, piperazinyl and morpholinyl groups are unsubstituted or substituted by one or more substituents selected from a hydroxyl group, a methyl group, a —CH$_2$OH group, a —CH$_2$—C(OH)(CH$_3$)$_2$ group, a methoxy group, an amino group, a —N(CH$_3$)$_2$ group, a —COOH group and a —CO$_2$Et group;

R$^4$ is selected from the group consisting of a —CO(CH$_2$)—OH group; —CO(CH$_2$)—CN group, a pyrazinyl group and a pyrimidinyl group, wherein the pyrazinyl and pyrimidinyl groups independently are unsubstituted or substituted with a CN group or a —CH$_2$OH group;

R$^5$ represents a —CH$_2$—CN group;

G$_2$ represents a pyrimidine group or a pyridine group, wherein the pyrimidine and pyridine groups are unsubstituted or substituted by a fluorine atom; and R$^6$ is selected from the group consisting of a hydrogen atom, a —CH$_2$CO$_2$CH$_2$Ph group, a —(CH$_2$)$_2$OCH$_3$ group, a —(CH$_2$)$_2$OCH$_2$CH$_3$ group, a —CH(CH$_3$)CH$_2$OCH$_3$ group, a methyl group, an ethyl group, a butyl group, a —CH$_2$CF$_3$ group, a —CH$_2$CHF$_2$ group, a CH(CH$_3$)$_2$ group, a —(CH$_2$)$_{2-3}$—OH group, a —(CH$_2$)$_{2-3}$N(CH$_3$)$_2$ group, a —CH(CH$_3$)—CH$_2$OH group, a —CH$_2$CH(OH)CH$_2$OH group.

Particular individual compounds of the invention include:

(Trans-4-{[5-fluoro-6-(4-hydroxypiperidin-1-yl)-2-pyrazolo[1,5-a]pyridin-3-ylpyrimidin-4-yl]amino}cyclohexyl)acetonitrile;

(Trans-4-{[6-(4-aminopiperidin-1-yl)-5-fluoro-2-pyrazolo[1,5-a]pyridin-3-ylpyrimidin-4-yl]amino}cyclohexyl)acetonitrile;

{Trans-4-[(5-fluoro-6-piperazin-1-yl-2-pyrazolo[1,5-a]pyridin-3-ylpyrimidin-4-yl)amino]cyclohexyl}acetonitrile;

[Trans-4-({6-[4-(dimethylamino)piperidin-1-yl]-5-fluoro-2-pyrazolo[1,5-a]pyridin-3-ylpyrimidin-4-yl}amino)cyclohexyl]acetonitrile;

(Trans-4-{[5-fluoro-6-(2-hydroxyethoxy)-2-pyrazolo[1,5-a]pyridin-3-ylpyrimidin-4-yl]amino}cyclohexyl)acetonitrile;

{Trans-4-[(6-{[(2S)-2,3-dihydroxypropyl]oxy}-5-fluoro-2-pyrazolo[1,5-a]pyridin-3-ylpyrimidin-4-yl)amino]cyclohexyl}acetonitrile;

{Trans-4-[(6-{[(2R)-2,3-dihydroxypropyl]oxy}-5-fluoro-2-pyrazolo[1,5-a]pyridin-3-ylpyrimidin-4-yl)amino]cyclohexyl}acetonitrile;

[Trans-4-({5-fluoro-6-[(2-hydroxyethyl)amino]-2-pyrazolo[1,5-a]pyridin-3-ylpyrimidin-4-yl}amino)cyclohexyl]acetonitrile;

[trans-4-({6-[2-(dimethylamino)ethoxy]-5-fluoro-2-pyrazolo[1,5-a]pyridin-3-ylpyrimidin-4-yl}amino)cyclohexyl]acetonitrile;

[Trans-4-({6-[2-(dimethylamino)ethoxy]-5-fluoro-2-pyrazolo[1,5-a]pyridin-3-ylpyrimidin-4-yl}amino)cyclohexyl]acetonitrile;

6-(4-Aminopiperidin-1-yl)-5-fluoro-N-[(1S)-1-(5-fluoropyridin-2-yl)ethyl]-2-pyrazolo[1,5-a]pyridin-3-ylpyrimidin-4-amine;

2-[(5-Fluoro-6-{[(1S)-1-(5-fluoropyrimidin-2-yl)ethyl]amino}-2-pyrazolo[1,5-a]pyridin-3-ylpyrimidin-4-yl)oxy]etanol;

(2S)-3-[(5-fluoro-6-{[(1S)-1-(5-fluoropyrimidin-2-yl)ethyl]amino}-2-pyrazolo[1,5-a]pyridin-3-ylpyrimidin-4-yl)oxy]propane-1,2-diol;

3-((3R)-3-{[5-fluoro-6-(2-hydroxyethoxy)-2-pyrazolo[1,5-a]pyridin-3-ylpyrimidin-4-yl]amino}piperidin-1-yl)-3-oxopropanenitrile;

3-{(3R)-3-[(6-butoxy-5-fluoro-2-pyrazolo[1,5-a]pyridin-3-ylpyrimidin-4-yl)amino]piperidin-1-yl}-3-oxopropanenitrile;

3-((3R)-3-{[6-(2-ethoxyethoxy)-5-fluoro-2-pyrazolo[1,5-a]pyridin-3-ylpyrimidin-4-yl]amino}piperidin-1-yl)-3-oxopropanenitrile;

3-[(3R)-3-({5-Fluoro-6-[4-(hydroxymethyl)phenyl]-2-pyrazolo[1,5-a]pyridin-3-ylpyrimidin-4-yl}amino)piperidin-1-yl]-3-oxopropanenitril;

3-((3R)-3-{[6-(6-Aminopyridin-3-yl)-5-fluoro-2-pyrazolo[1,5-a]pyridin-3-ylpyrimidin-4-yl]amino}piperidin-1-yl)-3-oxopropanenitrile;

3-((3R)-3-{[5-fluoro-6-(6-methoxypyridin-3-yl)-2-pyrazolo[1,5-a]pyridin-3-ylpyrimidin-4-yl]amino}piperidin-1-yl)-3-oxopropanenitrile;

3-((3R)-3-{[5-fluoro-6-(2-methylpyridin-4-yl)-2-pyrazolo[1,5-a]pyridin-3-ylpyrimidin-4-yl]amino}piperidin-1-yl)-3-oxopropanenitrile;

3-{(3R)-3-[[5-fluoro-6-(2-methylpyridin-4-yl)-2-pyrazolo[1,5-a]pyridin-3-ylpyrimidin-4-yl](methyl)amino]piperidin-1-yl}-3-oxopropanenitrile;

1-(5-Fluoro-6-{[(3R)-1-glycoloylpiperid in-3-yl]amino}-2-pyrazolo[1,5-a]pyridin-3-ylpyrimidin-4-yl)piperidin-4-ol;

2-[(3R)-3-({5-Fluoro-6-[4-(hydroxymethyl)piperidin-1-yl]-2-pyrazolo[1,5-a]pyridin-3-ylpyrimidin-4-yl}amino)piperidin-1-yl]-2-oxoethanol;

2-[(3R)-3-({5-Fluoro-6-[(2-hydroxyethypamino]-2-pyrazolo[1,5-a]pyridin-3-ylpyrimidin-4-yl}amino)piperidin-1-yl]-2-oxoethanol;

2-((3R)-3-{[5-fluoro-6-(4-methylpiperazin-1-yl)-2-pyrazolo[1,5-a]pyridin-3-ylpyrimidin-4-yl]amino}piperidin-1-yl)-2-oxoethanol;

2-{(3R)-3-[(5-Methyl-6-morpholin-4-yl-2-pyrazolo[1,5-a]pyridin-3-ylpyrimidin-4-yl)amino]piperidin-1-yl}-2-oxoethanol;

2-((3R)-3-{[6-(2-Methoxyethoxy)-5-methyl-2-pyrazolo[1,5-a]pyridin-3-ylpyrimidin-4-yl]amino}piperidin-1-yl)-2-oxoethanol;

Ethyl 1-(5-fluoro-6-{[(3R)-1-glycoloylpiperidin-3-yl]amino}-2-pyrazolo[1,5-a]pyridin-3-ylpyrimidin-4-yl)-4-methylpiperidine-4-carboxylate;

2-((3R)-3-{[5-Fluoro-2-(5-methylpyrazolo[1,5-a]pyridin-3-yl)-6-morpholin-4-ylpyrimidin-4-yl]amino}piperidin-1-yl)-2-oxoethanol;

Ethyl 1-(6-{[(3R)-1-(cyanoacetyl)piperidin-3-yl]amino}-5-fluoro-2-pyrazolo[1,5-a]pyridin-3-ylpyrimidin-4-yl)piperidine-4-carboxylate;

1-(6-{[(3R)-1-(Cyanoacetyl)piperidin-3-yl]amino}-5-fluoro-2-pyrazolo[1,5-a]pyridin-3-ylpyrimidin-4-yl)piperidine-4-carboxylic acid;

2-((3R)-3-{[5-Fluoro-2-pyrazolo[1,5-a]pyridin-3-yl-6-(1H-pyrazol-4-yl)pyrimidin-4-yl]amino}piperidin-1-yl)-2-oxoethanol;

1-[4-(5-Fluoro-6-{[(3R)-1-glycoloylpiperidin-3-yl]amino}-2-pyrazolo[1,5-a]pyridin-3-ylpyrimidin-4-yl)-1H-pyrazol-1-yl]-2-methylpropan-2-ol;

2-((3R)-3-{[5-Fluoro-6-(2-methylpyridin-4-yl)-2-pyrazolo[1,5-a]pyridin-3-ylpyrimidin-4-yl]amino}piperidin-1-yl)-2-oxoethanol;

2-((3R)-3-{[5-Fluoro-6-(6-methoxypyridin-3-yl)-2-pyrazolo[1,5-a]pyridin-3-ylpyrimidin-4-yl]amino}piperidin-1-yl)-2-oxoethanol;

2-((3R)-3-{[5-Fluoro-6-(6-methylpyridin-3-yl)-2-pyrazolo[1,5-a]pyridin-3-ylpyrimidin-4-yl]amino}piperidin-1-yl)-2-oxoethanol;

2-[(3R)-3-({5-Fluoro-6-[2-(hydroxymethyl)pyridin-4-yl]-2-pyrazolo[1,5-a]pyridin-3-ylpyrimidin-4-yl}amino)piperidin-1-yl]-2-oxoethanol;

Ethyl 5-(5-fluoro-6-{[(3R)-1-glycoloylpiperidin-3-yl]amino}-2-pyrazolo[1,5-a]pyridin-3-ylpyrimidin-4-yl)pyridine-2-carboxylate;

2-((3R)-3-{[5-Fluoro-6-(2-methoxyethoxy)-2-pyrazolo[1,5-a]pyridin-3-ylpyrimidin-4-yl]amino}piperidin-1-yl)-2-oxoethanol;

2-((3R)-3-{[5-Fluoro-6-(2-hydroxyethoxy)-2-pyrazolo[1,5-a]pyridin-3-ylpyrimidin-4-yl]amino}piperidin-1-yl)-2-oxoethanol;

3-[(5-Fluoro-6-{[(3R)-1-glycoloylpiperidin-3-yl]amino}-2-pyrazolo[1,5-a]pyridin-3-ylpyrimidin-4-yl)oxy]propan-1-ol;

2-{(3R)-3-[(5-Fluoro-6-methoxy-2-pyrazolo[1,5-a]pyridin-3-ylpyrimidin-4-yl)amino]piperidin-1-yl}-2-oxoethanol;

5-Fluoro-6-{[(3R)-1-glycoloylpiperidin-3-yl]amino}-2-pyrazolo[1,5-a]pyridin-3-ylpyrimidin-4-ol;

Benzyl [(5-fluoro-6-{[(3R)-1-glycoloylpiperidin-3-yl]amino}-2-pyrazolo[1,5-a]pyridin-3-ylpyrimidin-4-yl)oxy]acetate;

2-{(3R)-3-[(6-Ethoxy-5-fluoro-2-pyrazolo[1,5-a]pyridin-3-ylpyrimidin-4-yl)amino]piperidin-1-yl}-2-oxoethanol;

Ethyl 5-fluoro-6-{[(3R)-1-glycoloylpiperidin-3-yl]amino}-2-pyrazolo[1,5-a]pyridin-3-ylpyrimidine-4-carboxylate;

5-Fluoro-6-{[(3R)-1-glycoloylpiperidin-3-yl]amino}-2-pyrazolo[1,5-a]pyridin-3-ylpyrimidine-4-carbonitrile;

5-Fluoro-6-{[(3R)-1-glycoloylpiperidin-3-yl]amino}-2-pyrazolo[1,5-a]pyridin-3-ylpyrimidine-4-carboxamide;

2-((3R)-3-{[5-Fluoro-2-pyrazolo[1,5-a]pyridin-3-yl-6-(2,2,2-trifluoroethoxy)pyrimidin-4-yl]amino}piperidin-1-yl)-2-oxoethanol;

2-((3R)-3-{[6-(2,2-Difluoroethoxy)-5-fluoro-2-pyrazolo[1,5-a]pyridin-3-ylpyrimidin-4-yl]amino}piperidin-1-yl)-2-oxoethanol;

2-{(3R)-3-[(5-Fluoro-6-isopropoxy-2-pyrazolo[1,5-a]pyridin-3-ylpyrimidin-4-yl)amino]piperidin-1-yl}-2-oxoethanol;

2-{(3R)-3-[(5-Fluoro-6-morpholin-4-yl-2-pyrazolo[1,5-a]pyridin-3-ylpyrimidin-4-yl)oxy]piperidin-1-yl}-2-oxoethanol;

3-{(3R)-3-[(5-fluoro-6-morpholin-4-yl-2-pyrazolo[1,5-a]pyridin-3-ylpyrimidin-4-yl)oxy]piperidin-1-yl}-3-oxopropanenitrile;

5-((3R)-3-{[5-fluoro-6-(2-hydroxyethoxy)-2-pyrazolo[1,5-a]pyridin-3-ylpyrimidin-4-yl]amino}piperidin-1-yl)pyrazine-2-carbonitrile;

(5-{(3R)-3-[(5-fluoro-6-methoxy-2-pyrazolo[1,5-a]pyridin-3-ylpyrimidin-4-yl)amino]piperidin-1-yl}pyrazin-2-yl)methanol;

5-{(3R)-3-[(5-fluoro-6-methoxy-2-pyrazolo[1,5-a]pyridin-3-ylpyrimidin-4-yl)amino]piperidin-1-yl}pyrazine-2-carbonitrile;

2-((3R)-3-{[5-fluoro-6-(2-hydroxyethoxy)-2-pyrazolo[1,5-a]pyridin-3-ylpyrimidin-4-yl]amino}piperidin-1-yl)pyrimidine-5-carbonitrile;

2-[(3R)-3-({5-Fluoro-6-[(1S)-2-methoxy-1-methylethoxy]-2-pyrazolo[1,5-a]pyridin-3-ylpyrimidin-4-yl}amino)piperidin-1-yl]-2-oxoethanol;

(2S)-2-[(5-Fluoro-6-{[(3R)-1-glycoloylpiperidin-3-yl]amino}-2-pyrazolo[1,5-a]pyridin-3-ylpyrimidin-4-yl)oxy]propan-1-ol;

2-[(3R)-3-({5-Fluoro-6-[(1R)-2-methoxy-1-methylethoxy]-2-pyrazolo[1,5-a]pyridin-3-ylpyrimidin-4-yl}amino)piperidin-1-yl]-2-oxoethanol;

(2R)-2-[(5-Fluoro-6-{[(3R)-1-glycoloylpiperidin-3-yl]amino}-2-pyrazolo[1,5-a]pyridin-3-ylpyrimidin-4-yl)oxy]propan-1-ol;

2-{(3R)-3-[(5-Fluoro-2-pyrazolo[1,5-a]pyridin-3-yl-6-pyridin-3-ylpyrimidin-4-yl)amino]piperidin-1-yl}-2-oxoethanol;

2-{(3R)-3-[(5-Fluoro-6-methoxy-2-pyrazolo[1,5-a]pyridin-3-ylpyrimidin-4-yl)oxy]piperidin-1-yl}-2-oxoethanol;

3-{(3R)-3-[(5-Fluoro-6-methoxy-2-pyrazolo[1,5-a]pyridin-3-ylpyrimidin-4-yl)oxy]piperidin-1-yl}-3-oxopropanenitrile;

2-((3R)-3-{[5-Fluoro-6-(2-hydroxyethoxy)-2-pyrazolo[1,5-a]pyridin-3-ylpyrimidin-4-yl]oxy}piperidin-1-yl)-2-oxoethanol;

3-((3R)-3-{[5-Fluoro-6-(2-hydroxyethoxy)-2-pyrazolo[1,5-a]pyridin-3-ylpyrimidin-4-yl]oxy}piperidin-1-yl)-3-oxopropanenitrile;

2-((3R)-3-{[5-Fluoro-6-(4-methylpiperazin-1-yl)-2-pyrazolo[1,5-a]pyridin-3-ylpyrimidin-4-yl]oxy}piperidin-1-yl)-2-oxoethanol;

3-((3R)-3-{[5-Fluoro-6-(4-methylpiperazin-1-yl)-2-pyrazolo[1,5-a]pyridin-3-ylpyrimidin-4-yl]oxy}piperidin-1-yl)-3-oxopropanenitrile;

2-[(3R)-3-({5-Fluoro-6-[(2-hydroxyethyl)amino]-2-pyrazolo[1,5-a]pyridin-3-ylpyrimidin-4-yl}oxy)piperidin-1-yl]-2-oxoethanol;

3-[(3R)-3-({5-Fluoro-6-[(2-hydroxyethyl)amino]-2-pyrazolo[1,5-a]pyridin-3-ylpyrimidin-4-yl}oxy)piperidin-1-yl]-3-oxopropanenitrile;

2-((3R)-3-{[5-Fluoro-6-(2-methylpyridin-4-yl)-2-pyrazolo[1,5-a]pyridin-3-ylpyrimidin-4-yl]oxy}piperidin-1-yl)-2-oxoethanol;

3-((3R)-3-{[5-Fluoro-6-(2-methylpyridin-4-yl)-2-pyrazolo[1,5-a]pyridin-3-ylpyrimidin-4-yl]oxy}piperidin-1-yl)-3-oxopropanenitrile;

3-[(3R)-3-({5-Fluoro-6-[2-(hydroxymethyl)pyridin-4-yl]-2-pyrazolo[1,5-a]pyridin-3-ylpyrimidin-4-yl}oxy)piperidin-1-yl]-3-oxopropanenitrile;

2-[(3R)-3-({5-Fluoro-6-[2-(hydroxymethyl)pyridin-4-yl]-2-pyrazolo[1,5-a]pyridin-3-ylpyrimidin-4-yl}oxy)piperidin-1-yl]-2-oxoethanol;

1-(5-Fluoro-6-{[(3R)-1-glycoloylpiperidin-3-yl]oxy}-2-pyrazolo[1,5-a]pyridin-3-ylpyrimidin-4-yl)piperidin-4-ol;

3-((3R)-3-{[5-Fluoro-6-(4-hydroxypiperidin-1-yl)-2-pyrazolo[1,5-a]pyridin-3-ylpyrimidin-4-yl]oxy}piperidin-1-yl)-3-oxopropanenitrile;

2-((3R)-3-{[5-Fluoro-6-(2-methylpyridin-4-yl)-2-pyrazolo[1,5-a]pyridin-3-ylpyrimidin-4-yl][(methyl)amino]piperidin-1-yl}-2-oxoethanol;

3-[(3R)-3-({5-Fluoro-6-[2-(hydroxymethyl)pyridin-4-yl]-2-pyrazolo[1,5-a]pyridin-3-ylpyrimidin-4-yl}amino)piperidin-1-yl]-3-oxopropanenitrile;

5-(5-Fluoro-6-{[(3R)-1-glycoloylpiperidin-3-yl]amino}-2-pyrazolo[1,5-a]pyridin-3-ylpyrimidin-4-yl)pyridine-2-carboxylic acid;

2-{(3R)-3-[(5-Fluoro-2-pyrazolo[1,5-a]pyridin-3-yl-6-pyridin-4-ylpyrimidin-4-yl)amino]piperidin-1-yl}-2-oxoethanol;

2-[(3R)-3-({6-[6-(Dimethylamino)pyridin-3-yl]-5-fluoro-2-pyrazolo[1,5-a]pyridin-3-ylpyrimidin-4-yl}amino)piperidin-1-yl]-2-oxoethanol;

2-{(3R)-3-[(5-Fluoro-2'-methyl-2-pyrazolo[1,5-a]pyridin-3-yl-4,5'-bipyrimidin-6-yl)amino]piperidin-1-yl}-2-oxoethanol;

2-((3R)-3-{[6-(2-Ethoxyethoxy)-5-fluoro-2-pyrazolo[1,5-a]pyridin-3-ylpyrimidin-4-yl]amino}piperidin-1-yl)-2-oxoethanol;

2-[(3R)-3-({5-Fluoro-6-[6-(hydroxymethyl)pyridin-3-yl]-2-pyrazolo[1,5-a]pyridin-3-ylpyrimidin-4-yl}amino)piperidin-1-yl]-2-oxoethanol;

3-[(3R)-3-({5-Fluoro-6-[6-(hydroxymethyl)pyridin-3-yl]-2-pyrazolo[1,5-a]pyridin-3-ylpyrimidin-4-yl}amino)piperidin-1-yl]-3-oxopropanenitrile;

2-((3R)-3-{[6-(2,6-Dimethylpyridin-4-yl)-5-fluoro-2-pyrazolo[1,5-a]pyridin-3-ylpyrimidin-4-yl]amino}piperidin-1-yl)-2-oxoethanol;

3-((3R)-3-{[6-(2,6-Dimethylpyridin-4-yl)-5-fluoro-2-pyrazolo[1,5-a]pyridin-3-ylpyrimidin-4-yl]amino}piperidin-1-yl)-3-oxopropanenitrile;

2-[(3R)-3-({5-Fluoro-6-[5-(hydroxymethyl)pyridin-3-yl]-2-pyrazolo[1,5-a]pyridin-3-ylpyrimidin-4-yl}amino)piperidin-1-yl]-2-oxoethanol;

3-[(3R)-3-({5-Fluoro-6-[5-(hydroxymethyl)pyridin-3-yl]-2-pyrazolo[1,5-a]pyridin-3-ylpyrimidin-4-yl}amino)piperidin-1-yl]-3-oxopropanenitrile;

(2S)-1-[(5-Fluoro-6-{[(3R)-1-glycoloylpiperidin-3-yl]oxy}-2-pyrazolo[1,5-a]pyridin-3-ylpyrimidin-4-yl)oxy]propan-2-ol;

5-[(3R)-3-({5-Fluoro-6-[(1R)-2-methoxy-1-methylethoxy]-2-pyrazolo[1,5-a]pyridin-3-ylpyrimidin-4-yl}amino)piperidin-1-yl]pyrazine-2-carbonitrile;

Isopropyl 5-fluoro-6-{[(3R)-1-glycoloylpiperidin-3-yl]amino}-2-pyrazolo[1,5-a]pyridin-3-ylpyrimidine-4-carboxylate;

2-{(3R)-3-[(6-Methoxy-5-methyl-2-pyrazolo[1,5-a]pyridin-3-ylpyrimidin-4-yl)amino]piperidin-1-yl}-2-oxoethanol;

2-{(3R)-3-[(6-Methoxy-2-pyrazolo[1,5-a]pyridin-3-ylpyrimidin-4-yl)amino]piperidin-1-yl}-2-oxoethanol;

3-{(3R)-3-[(6-Methoxy-2-pyrazolo[1,5-a]pyridin-3-ylpyrimidin-4-yl)amino]piperidin-1-yl}-3-oxopropanenitrile;

2-((3R)-3-{[6-(2-Methoxyethoxy)-2-pyrazolo[1,5-a]pyridin-3-ylpyrimidin-4-yl]amino}piperidin-1-yl)-2-oxoethanol;

3-((3R)-3-{[6-(2-Methoxyethoxy)-2-pyrazolo[1,5-a]pyridin-3-ylpyrimidin-4-yl]amino}piperidin-1-yl)-3-oxopropanenitrile;

2-((3R)-3-{[6-(2-Methoxypyridin-4-yl)-2-pyrazolo[1,5-a]pyridin-3-ylpyrimidin-4-yl]amino}piperidin-1-yl)-2-oxoethanol;

2-((3R)-3-{[6-(6-Methylpyridin-3-yl)-2-pyrazolo[1,5-a]pyridin-3-ylpyrimidin-4-yl]amino}piperidin-1-yl)-2-oxoethanol;

3-((3R)-3-{[6-(6-Methylpyridin-3-yl)-2-pyrazolo[1,5-a]pyridin-3-ylpyrimidin-4-yl]amino}piperidin-1-yl)-3-oxopropanenitrile;

2-((3R)-3-{[6-(2,6-Dimethylpyridin-4-yl)-2-pyrazolo[1,5-a]pyridin-3-ylpyrimidin-4-yl]amino}piperidin-1-yl)-2-oxoethanol;

3-((3R)-3-{[6-(2,6-Dimethylpyridin-4-yl)-2-pyrazolo[1,5-a]pyridin-3-ylpyrimidin-4-yl]amino}piperidin-1-yl)-3-oxopropanenitrile;

3-((3R)-3-{[6-(2-Hydroxyethoxy)-2-pyrazolo[1,5-a]pyridin-3-ylpyrimidin-4-yl]amino}piperidin-1-yl)-3-oxopropanenitrile;

5-((3R)-3-{[6-(2-Hydroxyethoxy)-2-pyrazolo[1,5-a]pyridin-3-ylpyrimidin-4-yl]amino}piperidin-1-yl)pyrazine-2-carbonitrile;

5-(6-{[(3R)-1-Glycoloylpiperidin-3-yl]amino}-2-pyrazolo[1,5-a]pyridin-3-ylpyrimidin-4-yl)pyridin-3-ol;

3-((3R)-3-{[6-(5-Hydroxypyridin-3-yl)-2-pyrazolo[1,5-a]pyridin-3-ylpyrimidin-4-yl]amino}piperidin-1-yl)-3-oxopropanenitrile;

2-{(3R)-3-[(5-Fluoro-6-morpholin-4-yl-2-pyrazolo[1,5-a]pyridin-3-ylpyrimidin-4-yl)(methyl)amino]piperidin-1-yl}-2-oxoethanol; or a pharmaceutically acceptable salt, N-oxide, solvate, stereoisomer or deuterated derivative thereof.

Of outstanding interest are:

3-((3R)-3-{[5-fluoro-6-(2-hydroxyethoxy)-2-pyrazolo[1,5-a]pyridin-3-ylpyrimidin-4-yl]amino}piperidin-1-yl)-3-oxopropanenitrile;

3-((3R)-3-{[6-(2-ethoxyethoxy)-5-fluoro-2-pyrazolo[1,5-a]pyridin-3-ylpyrimidin-4-yl]amino}piperidin-1-yl)-3-oxopropanenitrile;

2-((3R)-3-{[5-Fluoro-6-(2-methylpyridin-4-yl)-2-pyrazolo[1,5-a]pyridin-3-ylpyrimidin-4-yl]amino}piperidin-1-yl)-2-oxoethanol;

2-((3R)-3-{[5-Fluoro-6-(6-methylpyridin-3-yl)-2-pyrazolo[1,5-a]pyridin-3-ylpyrimidin-4-yl]amino}piperidin-1-yl)-2-oxoethanol;

2-((3R)-3-{[5-Fluoro-6-(2-methoxyethoxy)-2-pyrazolo[1,5-a]pyridin-3-ylpyrimidin-4-yl]amino}piperidin-1-yl)-2-oxoethanol;

2-((3R)-3-{[5-Fluoro-6-(2-hydroxyethoxy)-2-pyrazolo[1,5-a]pyridin-3-ylpyrimidin-4-yl]amino}piperidin-1-yl)-2-oxoethanol;

3-[(5-Fluoro-6-{[(3R)-1-glycoloylpiperidin-3-yl]amino}-2-pyrazolo[1,5-a]pyridin-3-ylpyrimidin-4-yl)oxy]propan-1-ol;

2-{(3R)-3-[(5-Fluoro-6-methoxy-2-pyrazolo[1,5-a]pyridin-3-ylpyrimidin-4-yl)amino]piperidin-1-yl}-2-oxoethanol;

2-{(3R)-3-[(6-Ethoxy-5-fluoro-2-pyrazolo[1,5-a]pyridin-3-ylpyrimidin-4-yl)amino]piperidin-1-yl}-2-oxoethanol;

5-Fluoro-6-{[(3R)-1-glycoloylpiperidin-3-yl]amino}-2-pyrazolo[1,5-a]pyridin-3-ylpyrimidine-4-carbonitrile;

2-((3R)-3-{[6-(2,2-Difluoroethoxy)-5-fluoro-2-pyrazolo[1,5-a]pyridin-3-ylpyrimidin-4-yl]amino}piperidin-1-yl)-2-oxoethanol;

2-{(3R)-3-[(5-fluoro-6-methoxy-2-pyrazolo[1,5-a]pyridin-3-ylpyrimidin-4-yl)oxy]piperidin-1-yl}-2-oxoethanol;

3-[(3R)-3-({5-Fluoro-6-[2-(hydroxymethyl)pyridin-4-yl]-2-pyrazolo[1,5-a]pyridin-3-ylpyrimidin-4-yl}amino)piperidin-1-yl]-3-oxopropanenitrile;

2-{(3R)-3-[(6-Methoxy-5-methyl-2-pyrazolo[1,5-a]pyridin-3-ylpyrimidin-4-yl)amino]piperidin-1-yl}-2-oxoethanol;

2-{(3R)-3-[(6-Methoxy-2-pyrazolo[1,5-a]pyridin-3-ylpyrimidin-4-yl)amino]piperidin-1-yl}-2-oxoethanol;

3-{(3R)-3-[(6-Methoxy-2-pyrazolo[1,5-a]pyridin-3-ylpyrimidin-4-yl)amino]piperidin-1-yl}-3-oxopropanenitrile;

2-((3R)-3-{[6-(2-Methoxyethoxy)-2-pyrazolo[1,5-a]pyridin-3-ylpyrimidin-4-yl]amino}piperidin-1-yl)-2-oxoethanol;

3-((3R)-3-{[6-(2-Methoxyethoxy)-2-pyrazolo[1,5-a]pyridin-3-ylpyrimidin-4-yl]amino}piperidin-1-yl)-3-oxopropanenitrile;

2-((3R)-3-{[6-(2-Methoxypyridin-4-yl)-2-pyrazolo[1,5-a]pyridin-3-ylpyrimidin-4-yl]amino}piperidin-1-yl)-2-oxoethanol;

2-((3R)-3-{[6-(6-Methylpyridin-3-yl)-2-pyrazolo[1,5-a]pyridin-3-ylpyrimidin-4-yl]amino}piperidin-1-yl)-2-oxoethanol;

3-((3R)-3-{[6-(6-Methylpyridin-3-yl)-2-pyrazolo[1,5-a]pyridin-3-ylpyrimidin-4-yl]amino}piperidin-1-yl)-3-oxopropanenitrile;

3-((3R)-3-{[6-(2-Hydroxyethoxy)-2-pyrazolo[1,5-a]pyridin-3-ylpyrimidin-4-yl]amino}piperidin-1-yl)-3-oxopropanenitrile;

5-(6-{[(3R)-1-Glycoloylpiperidin-3-yl]amino}-2-pyrazolo[1,5-a]pyridin-3-ylpyrimidin-4-yl)pyridin-3-ol;

3-((3R)-3-{[6-(5-Hydroxypyridin-3-yl)-2-pyrazolo[1,5-a]pyridin-3-ylpyrimidin-4-yl]amino}piperidin-1-yl)-3-oxopropanenitrile; or a pharmaceutically acceptable salt, N-oxide, solvate, stereoisomer, or deuterated derivative thereof.

General Synthetic Procedures

The 2-(pyrazolopyridin-3-yl)pyrimidine derivatives of the invention can be prepared using the methods and procedures described herein, or using similar methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. The choice of a suitable protecting group for a particular functional group, as well as suitable conditions for protection and deprotection, are well known in the art. For example, numerous protecting groups, and their introduction and removal are described in T. W. Greene and G. M. Wuts, Protecting Groups in Organic Synthesis, Third Edition, Wiley, New York, 1999, and references cited therein.

Processes for preparing compounds of the invention are provided as further embodiments of the invention and are illustrated by the procedures below.

According to one embodiment of the present invention, compounds of general formula (I) may be prepared by the following synthetic route as illustrated in Scheme 1:

Scheme 1

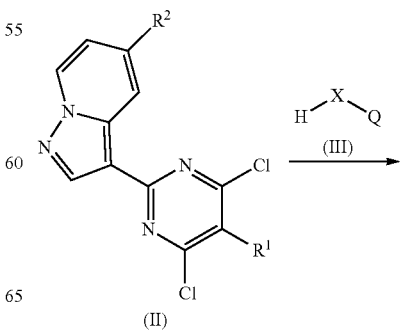

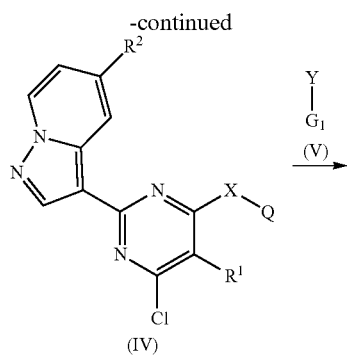

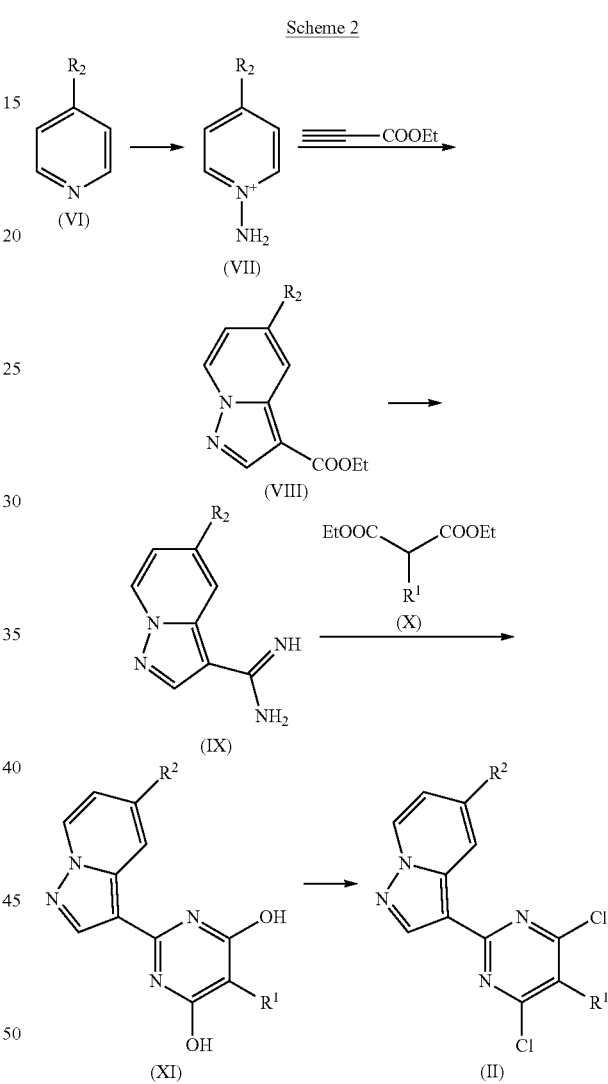

Treatment of dichloropyrimidines of formula (II) with amines or alcohols of formula (III) in the presence of a base such as triethylamine or sodium hydrogencarbonate in a solvent such as methanol or ethanol at temperatures ranging from ambient temperature to reflux gives rise to compounds of formula (IV).

In the particular case where $G_1$ is an aryl or heteroaryl ring, compounds of formula (I) may be obtained from chloropyrimidines of formula (IV) by reaction with compounds of formula (V), where Y is a boronic acid or a boronate ester, under Suzuki-Miyaura reaction conditions (Miyaura, N.; Suzuki, A. Chem. Rev. 1995, 95, 2457). Such reactions may be catalysed by a suitable palladium catalyst such as [1,1-bis(diphenylphosphino)ferrocene]palladium(II) dichloride dichloromethane complex or tetrakis(triphenylphosphine)palladium(O) in a solvent such as toluene, 1,4-dioxane or 1,2-dimethoxyethane in the presence of a base such as cesium carbonate or sodium carbonate at temperatures ranging from 80° C. to 110° C. with or without the use of microwave irradiation.

Boronic acids or boronates of formula (V) where $G_1$ is an aryl or heteroaryl ring and Y is a boronic acid or boronate ester may be commercially available or may be prepared from the corresponding haloderivatives of formula (V), where Y is a bromine atom or a chlorine atom, by treatment with an appropriate boron reagent such as 4,4,4',4',5,5,5',5'-octamethyl-2,2'-bi(1,3,2-dioxaborolane) with a palladium catalyst such as bis(diphenylphosphino)ferrocene]palladium (II) dichloride dichloromethane complex or bis(dibenzylideneacetone)palladium(0), in a solvent such as 1,4-dioxane or 1,2-dimethoxyethane, with or without the presence of a ligand such as tricyclohexylphosphine, in the presence of a base such as potassium acetate at temperatures ranging from 80-150° C. with or without the use of microwave irradiation.

In another particular case where G1 is an heterocyclyl group attached to the pyrimidine ring through a nitrogen atom, a —CN group, a (CHR$_7$)m-NR'R", or a —O—R$^6$ group, compounds of formula (I) may be prepared by reaction of chloroderivatives of formula (IV) with heterocyclic or linear amines, alcohols or cyanides of formula (V), where Y is an hydrogen or metal atom, in the presence of a base such as sodium hydrogencarbonate or N-ethyl-N-isopropylpropan-2-amine without the use of a solvent or in a solvent such as N,N'-dimethylacetamide or 1-methylpyrrolidin-2-one at temperatures ranging from 80-130° C. with or without the use of microwave irradiation.

Compounds of formula (II) may be prepared as illustrated in Scheme 2:

Reaction of ethyl propiolate with N-aminopyridinium salts of formula (VII) in the presence of a base, for example potassium carbonate, in a solvent such as N,N'-dimethylformamide at temperatures ranging from 0° C. to ambient temperature, furnishes esters of formula (VIII). N-Aminopyridinium salts of formula (VII) may be commercially available or may be prepared by reaction of the corresponding pyridines of formula (VI) with O-(mesitylsulfonyl)hydroxylamine in a suitable solvent such as dichloromethane at temperatures ranging from 0° C. to ambient temperature. Treatment of esters of formula (VIII) with a mixture of trimethylaluminum and ammonium chloride in a solvent such as toluene at 80° C. provides amidine intermediates of formula (IX). Amidines of formula (IX) may be reacted with malonate esters of formula (X) to give dihydroxypirimidines of formula (XI). Such reactions may be carried out in the presence of a suitable base such as sodium methoxide in a solvent such as methanol at temperatures ranging from 0° C. to ambient temperature. Dihydroxypirimidines of formula (XI) may be converted to dichloropyrimidines of formula (II) by treatment with a suitable chlorinating agent, for example phosphorus(V) oxychloride, at temperatures ranging from 25° C. to reflux.

In the particular case where G1 is an aryl or heteroaryl ring, compounds of general formula (I) may also be prepared by an alternative synthetic approach as shown in Scheme 3:

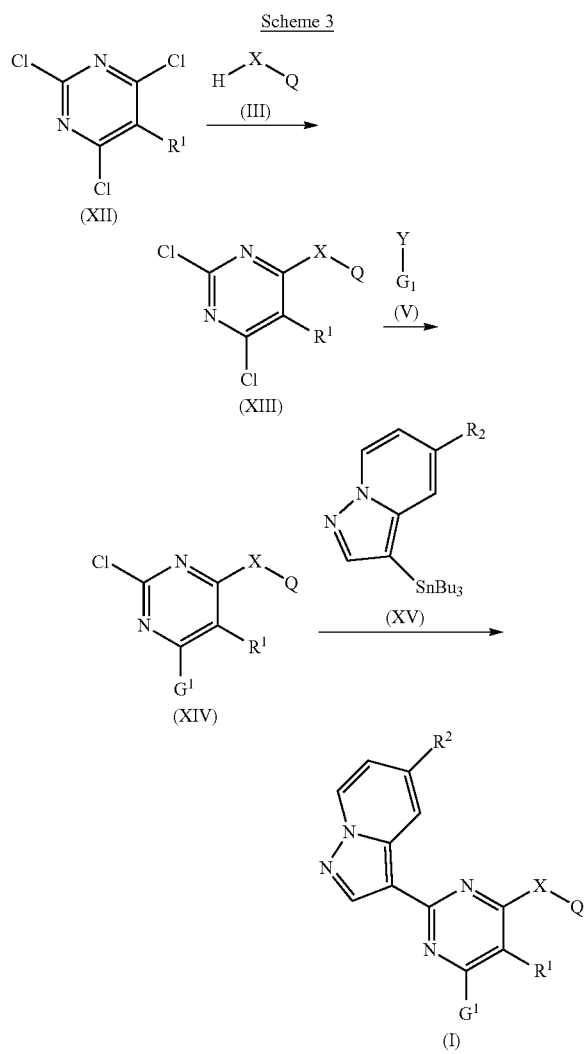

Treatment of trichloropyrimidines of formula (XII) with amines of formula (III) in the presence of a base such as triethylamine or sodium hydrogencarbonate in a solvent such as ethanol at −20° C. gives rise to compounds of formula (XIII).

In the particular case where $G_1$ is an aryl or heteroaryl ring, compounds of formula (XIV) may be obtained from dichloropyrimidines of formula (XIII) by reaction with compounds of formula (V), where Y is a boronic acid or a boronate ester, under Suzuki-Miyaura reaction conditions. Such reactions may be catalysed by a suitable palladium catalyst such as tetrakis(triphenylphosphine)palladium(0) in a solvent such as 1,2-dimethoxyethane in the presence of a base such as sodium carbonate at 80° C. Reaction of chloropyrimidines of formula (XIV) with stannanes of formula (XV) in the presence of a palladium catalyst such as tetrakis (triphenylphosphine)palladium(0) in a solvent such as 1,4-dioxane at 100° C. provides compounds of formula (I).

In yet another particular case, compounds of formula (I), in which the residue at $G_1$, or Q contains an alcohol, phenol or carboxylic acid moiety functionalized with an appropriate protecting group such as benzyl (Bn) or methoxy (OMe), may be deprotected at the alcohol, phenol or carboxylic acid moiety under standard conditions (*Greene's Protective Groups in Organic Synthesis*, ISBN: 0471697540). In the particular case of primary alcohols, the free alcohol moiety may then be oxidized under standard conditions to give the corresponding aldehyde.

In yet another particular case, compounds of formula (I), in which the residue at $G_1$, or Q contains an amine moiety functionalized with an appropriate protecting group such as tert-butoxycarbonyl (BOC) or benzyloxycarbonyl (CBZ), may be deprotected at the amine moiety under standard conditions (*Greene's Protective Groups in Organic Synthesis*, ISBN: 0471697540). The corresponding free amine may then be further functionalized under standard conditions to give the corresponding amides, carbamates and N-alkylated and N-arylated amines.

Starting compounds are commercially available or may be obtained following the conventional synthetic methods already known in the art.

The synthesis of the compounds of the invention and of the intermediates for use therein are illustrated by the following Examples (1-63) (including Preparations 1-8) and are given in order to provide a person skilled in the art with a sufficiently clear and complete explanation of the present invention, but should not be considered as limiting of the essential aspects of its subject, as set out in the preceding portions of this description.

PREPARATIONS

Preparation 1

Pyrazolo[1,5-a]pyridine-3-carboximidamide a) Ethyl pyrazolo[1,5-a]pyridine-3-carboxylate Potassium carbonate (6.10 g, 44.14 mmol) was added to a stirred solution of 1-aminopyridinium iodide (6.57 g, 29.59 mmol) in anhydrous N,N-dimethylformamide (44 mL) at 0° C. Ethyl propiolate (3 mL, 29.7 mmol) was then added dropwise and the resulting mixture was stirred overnight at room temperature. The reaction mixture was partitioned between water and chloroform. The organic phase was separated, washed with water and brine, dried over sodium sulfate and the solvent was evaporated to dryness to yield the title compound (5.51 g, 96%) as a red oil.

LRMS (m/z): 191 (M+1)$^+$.

b) Pyrazolo[1,5-a]pyridine-3-carboximidamide

A 2.0 M solution of trimethylaluminum in toluene (58.9 mL, 118.29 mmol) was added dropwise to a stirred suspension of ammonium chloride (5.90 g, 118.29 mmol) in toluene (100 mL) at 0° C. The reaction mixture was stirred at room temperature for 1 hour. A solution of ethyl pyrazolo[1,5-a]pyridine-3-carboxylate (Preparation 1a, 7.50 g, 39.43 mmol) in toluene (20 mL) was then added and the resulting mixture was stirred overnight at 80° C. Additional 2.0 M solution of trimethylaluminum in toluene (58.9 mL, 118.29 mmol) and ammonium chloride (5.90 g, 118.29 mmol) in toluene (100 mL) were added and the reaction mixture was stirred at 80° C. for further 24 h. After cooling to 0° C. in an ice bath, methanol (40 mL) was added dropwise. The solid formed was filtered and washed with methanol and the filtrate was evaporated to dryness. Purification of the residue by flash chromatography (dichloromethane to 7:3 dichloromethane/ethanol) gave the title compound (4.72 g, 74%) as a yellow solid.

LRMS (m/z): 161 (M+1)$^+$.

c) 5-Fluoro-2-pyrazolo[1,5-a]pyridin-3-ylpyrimidine-4,6-diol

Pyrazolo[1,5-a]pyridine-3-carboximidamide (Preparation 1b, 4.75 g, 29.47 mmol) was added portionwise to a stirred solution of sodium (1.63 g, 71.02 mmol) in methanol (120 mL) at 0° C. Diethyl 2-fluoromalonate (7.0 mL, 44.20 mmol) was then added and the reaction mixture was stirred from 0° C. to room temperature overnight. The solvent was evaporated to dryness to yield the title compound (7.25 g, 99%) as a solid that was used in the next synthetic step without further purification.

LRMS (m/z): 247 (M+1)$^+$.
$^1$H-NMR δ (300 MHz, DMSO-d$_6$): 7.23 (t, 1H), 7.50-7.73 (m, 1H), 8.71 (d, 1H), 8.85-8.94 (m, 2H), 11.83 (bs, 1H), 12.70 (br.s., 1H).

d) 3-(4,6-Dichloro-5-fluoropyrimidin-2-yl)pyrazolo[1,5-a]pyridine

A mixture of 5-fluoro-2-pyrazolo[1,5-a]pyridin-3-ylpyrimidine-4,6-diol (Preparation 1c, 7.00 g, 28.43 mmol) and phosphorus(V) oxychloride (55 mL, 589 mmol) was stirred at 110° C. for 24 hours. The solvent was then removed under reduced pressure and the residue was partitioned between dichloromethane and water. The organic layer was separated, washed with brine, dried over magnesium sulfate and the solvent was evaporated in vacuo. The crude product was purified by flash chromatography (hexanes to dichloromethane) to yield the title compound (5.3 g, 65%) as a yellow solid.

LRMS (m/z): 283 (M+1)$^+$.
$^1$H-NMR δ (300 MHz, CDCl$_3$): 7.00 (td, 1H), 7.44 (ddd, 1H), 8.62 (ddt, 2H), 8.74 (s, 1H).

Preparation 2

{Trans-4-[(6-chloro-5-fluoro-2-pyrazolo[1,5-a]pyridin-3-ylpyrimidin-4-yl)amino]cyclohexyl}acetonitrile A mixture of 3-(4,6-dichloro-5-fluoropyrimidin-2-yl)pyrazolo[1,5-a]pyridine (Preparation 1d, 0.30 g, 1.06 mmol), (trans-4-aminocyclohexyl)acetonitrile hydrochloride* (0.22 g, 1.27 mmol) and sodium hydrogencarbonate (0.39 g, 4.63 mmol) in ethanol (6 mL) was heated at reflux overnight. The solvent was evaporated and the residue was partitioned between water and ethyl acetate. The aqueous layer was extracted with ethyl acetate, the combined organic layers were washed with brine, dried over magnesium sulfate and the solvent was evaporated in vacuo. The resulting crude was purified by flash chromatography (gradient from hexanes to ethyl acetate) to yield the title compound (0.30 g, 72%) as a solid.

Prepared following the experimental procedure described in WO2011157397,

Preparation 50

LRMS (m/z): 385 (M+1)$^+$.

Preparation 3

(S)-6-Chloro-5-fluoro-N-(1-(5-fluoropyridin-2-yl)ethyl)-2-(pyrazolo[1,5-a]pyridin-3-yl)pyrimidin-4-amine A mixture of 3-(4,6-dichloro-5-fluoropyrimidin-2-yl)pyrazolo[1,5-a]pyridine (Preparation 1d, 1.00 g, 3.53 mmol), (1S)-1-(5-fluoropyridin-2-yl)ethanamine dihydrochloride (0.85 g, 6.06 mmol) and sodium hydrogencarbonate (1.40 g, 16.66 mmol) in ethanol (20 mL) was heated at reflux overnight. The solvent was evaporated and the residue was crystallized from methanol to yield the title compound (1.25 g, 82%) as a solid.

LRMS (m/z): 387 (M+1)$^+$.

Preparation 4

6-Chloro-5-fluoro-N-[(1S)-1-(5-fluoropyrimidin-2-yl)ethyl]-2-pyrazolo[1,5-a]pyridin-3-ylpyrimidin-4-amine Obtained as a solid (70%) from 3-(4,6-dichloro-5-fluoropyrimidin-2-yl)pyrazolo[1,5-a]pyridine (Preparation 1d) and (1S)-1-(5-fluoropyrimidin-2-yl)ethanamine following the experimental procedure as described in Preparation 3, followed by purification of the crude product by flash chromatography (gradient from dichloromethane to dichloromethane/methanol 95:5).

LRMS (m/z): 388 (M+1)$^+$.
$^1$H-NMR δ (300 MHz, CDCl$_3$): 1.72 (d, 3H), 5.63 (m, 1H), 6.32 (m, 1H), 6.94 (t, 1H), 7.43 (m, 1H), 8.52 (m, 2H), 8.64 (d, 2H).

Preparation 5

Tert-butyl (3R)-3-[(6-chloro-5-fluoro-2-pyrazolo[1,5-a]pyridin-3-ylpyrimidin-4-yl)amino]piperidine-1-carboxylate (R)-Tert-butyl 3-aminopiperidine-1-carboxylate (2.97 g, 14.83 mmol) was added to a solution of 3-(4,6-dichloro-5-fluoropyrimidin-2-yl)pyrazolo[1,5-a]pyridine (Preparation 1d, 3.50 g, 12.36 mmol) and triethylamine (2.0 mL, 15.08 mmol) in ethanol (80 mL) and the resulting mixture was stirred at 80° C. for 48 hours. After cooling to room temperature, the solvent was evaporated under reduced pressure and water was added. The precipitate was filtered and dried in vacuo to give the title compound (5.60 g, 100%) as a white solid.

LRMS (m/z): 447 (M+1)$^+$.

¹H-NMR δ (300 MHz, CDCl₃): 1.6 (s, 9H), 1.7-1.9 (m, 3H), 2.0-2.1 (m, 1H), 3.5 (bs, 4H), 4.3 (d, 1H), 5.2 (s, 1H), 6.9 (t, 1H), 7.3-7.4 (m, 1H), 8.5 (t, 2H), 8.3 (s, 1H).

Preparation 6

3-{(3R)-3-[(6-chloro-5-fluoro-2-pyrazolo[1,5-a]pyridin-3-ylpyrimidin-4-yl)amino]piperidin-1-yl}-3-oxopropanenitrile a) 6-Chloro-5-fluoro-N-[(3R)-piperidin-3-yl]-2-pyrazolo[1,5-a]pyridin-3-ylpyrimidin-4-amine 4.0 M Hydrogen chloride solution in 1,4-dioxane (31.4 mL, 125.6 mmol) was added to a solution of tert-butyl (3R)-3-[(6-chloro-5-fluoro-2-pyrazolo[1,5-a]pyridin-3-ylpyrimidin-4-yl)amino]piperidine-1-carboxylate (Preparation 5, 5.61 g, 12.55 mmol) in 1,4-dioxane (150 mL) and the resulting mixture was stirred overnight at room temperature. The precipitate formed was filtered and washed with 1,4-dioxane and diethyl ether and dried in vacuo to give the hydrochloride salt of the title compound (5.50 g, 100%) as a white solid.

LRMS (m/z): 347 (M+1)⁺.
¹H-NMR δ (300 MHz, CD₃OD): 1.73-2.24 (m, 5H), 2.93-3.15 (m, 2H), 3.43 (t, 1H), 3.61-3.73 (m, 1H), 4.44-4.75 (m, 1H), 7.10 (td, 1H), 7.50 (ddd, 1H), 8.53 (d, 1H), 8.61 (dd, 2H).

b) 3-{(3R)-3-[(6-Chloro-5-fluoro-2-pyrazolo[1,5-a]pyridin-3-ylpyrimidin-4-yl)amino]piperidin-1-yl}-3-oxopropanenitrile 3-[(2,5-Dioxopyrrolidin-1-yl)oxy]-3-oxopropanenitrile (prepared as described in BE875054(A1), 3.58 g, 19.66 mmol) was added to a solution of 6-chloro-5-fluoro-N-[(3R)-piperidin-3-yl]-2-pyrazolo[1,5-a]pyridin-3-yl-pyrimidin-4-amine (Preparation 6a, 5.5 g, 13.10 mmol) and triethylamine (9.1 mL, 65.7 mmol) in dichloromethane (10 mL). The resulting mixture was stirred overnight at room temperature. Additional 3-[(2,5-dioxopyrrolidin-1-yl)oxy]-3-oxopropanenitrile (0.80 g, 4.39 mmol) was added and the reaction mixture was stirred at room temperature for further 5 hours. The resulting mixture was partitioned between water and ethyl acetate, the organic layer was separated and the aqueous phase was extracted twice with ethyl acetate. The combined organic layers were washed with water, brine, dried over magnesium sulfate and concentrated in vacuo. The resulting crude was purified by flash chromatography (gradient from hexanes to ethyl acetate) to yield the title compound (0.37 g, 80%) as a white solid.

LRMS (m/z): 414 (M+1)⁺.
¹H-NMR δ (300 MHz, CDCl₃): 1.71-2.02 (m, 4H), 2.20 (t, 1H), 3.34-3.51 (m, 2H), 3.62-3.71 (m, 1H), 3.92 (dd, 1H), 4.30 (bs, 1H), 4.60 (d, 1H), 5.03 (d, 1H), 6.91 (dt, 1H), 7.39 (ddd, 1H), 8.40-8.61 (m, 2H), 8.7 (s, 1H).

Preparation 7

(R)-1-(3-((6-Chloro-5-fluoro-2-(pyrazolo[1,5-a]pyridin-3-yl)pyrimidin-4-yl)amino)piperidin-1-yl)-2-hydroxyethanone A mixture of 6-chloro-5-fluoro-N-[(3R)-piperidin-3-yl]-2-pyrazolo[1,5-a]pyridin-3-ylpyrimidin-4-amine (Preparation 6a, 0.46 g, 1.10 mmol), 2-hydroxyacetic acid (0.10 g, 1.10 mmol), 1-[bis(dimethylamino)methylene]-1H-1,2,3-triazolo[4,5-b]pyridinium-3-oxide hexafluorophosphate (0.54 g, 1.42 mmol) and triethylamine (0.53 mL, 3.82 mmol) in N,N-dimethylformamide (2 mL) was stirred at room temperature for 18 hours. The resulting mixture was partitioned between water and ethyl acetate, the organic layer was separated and the aqueous phase was extracted twice with ethyl acetate. The combined organic layers were washed with water, brine, dried over magnesium sulfate and concentrated in vacuo. The resulting crude was purified by flash chromatography (gradient from dichloromethane to dichloromethane/methanol 95:5) to yield the title compound (0.37 g, 80%) as a white solid.

LRMS (m/z): 405 (M+1)⁺.

Preparation 8

Tert-butyl(3R)-3-[(6-chloro-5-methyl-2-pyrazolo[1,5-a]pyridin-3-ylpyrimidin-4-yl)amino]piperidine-1-carboxylate a) 5-Methyl-2-(pyrazolo[1,5-a]pyridin-3-yl)pyrimidine-4,6-diol Pyrazolo[1,5-a]pyridine-3-carboximidamide (Preparation 1b, 2.89 g, 18.05 mmol) and diethyl methylmalonate (6.44 mL, 37.45 mmol) were added portionwise to a solution of sodium (1.24 g, 53.91 mmol) in methanol (14 mL) at 0° C. and the resulting suspension was stirred at room temperature overnight. The solvent was evaporated to dryness and the residue was dissolved in water and acidified to pH=1 using a 6N hydrochloric acid solution. The precipitate was filtered, washed with water and dried under vacuum to yield the title compound (3.54 g, 81%) as a yellow solid.

LRMS (m/z): 243 (M+1)⁺.
¹H-NMR δ (400 MHz, DMSO-d₆): 1.79 (s, 3H), 7.10-7.14 (t, 1H), 7.52-7.56 (dd, 1H), 8.73-8.75 (d, 1H), 8.81-8.83 (d, 1H), 8.91 (s, 1H).

b) 3-(4,6-Dichloro-5-methylpyrimidin-2-yl)pyrazolo[1,5-a]pyridine

Obtained as a solid (30%) from 5-methyl-2-(pyrazolo[1,5-a]pyridin-3-yl)pyrimidine-4,6-diol (Preparation 8a) and phosphorus(V) oxychloride following the experimental procedure as described in Preparation 1b followed by purification of the crude product by flash chromatography (hexanes/ethyl acetate 1:4).

LRMS (m/z): 279 (M+1)⁺.
¹H-NMR δ (400 MHz, CDCl₃): 2.47 (s, 3H), 6.93-6.97 (t, 1H), 7.39-7.44 (dd, 1H), 8.53-8.56 (m, 1H), 8.71 (s, 1H).

c) (R)-Tert-butyl 3-((6-chloro-5-methyl-2-(pyrazolo[1,5-a]pyridin-3-yl)pyrimidin-4-yl)amino)piperidine-1-carboxylate A mixture of 3-(4,6-dichloro-5-methylpyrimidin-2-yl)pyrazolo[1,5-a]pyridine (Preparation 8b, 1.11 g, 3.98 mmol), (R)-tert-butyl 3-aminopiperidine-1-carboxylate (0.93 g, 4.65 mmol) and diisopropylethylamine (1.04 mL, 5.97 mmol) in ethanol (12 mL) was stirred 68 hours at 80° C. N,N'-dimethylacetamide (9 mL) was then added and the reaction mixture was stirred at 100° C. for further 68 hours. Ethanol was evaporated and excess of water was added. The precipitate was filtered, washed with water and dried to give the title compound (1.49 g, 85%).

LRMS (m/z): 443 (M+1)⁺.

Preparation 9

Tert-butyl (3R)-3-[(6-chloro-5-fluoro-2-pyrazolo[1,5-a]pyridin-3-ylpyrimidin-4-yl)oxy]piperidine-1-carboxylate To a solution of tert-butyl (3R)-3-hydroxypiperidine-1-carboxylate (853 mg, 4.24 mmol) in dioxane (50 mL) was added potassium tert-butoxide (476 mg, 4.24 mmol). The mixture was stirred at room temperature for 15 minutes and then 3-(4,6-dichloro-5-fluoropyrimidin-2-yl)pyrazolo[1,5-a]pyridine (Preparation 1d, 1.00 g, 2.53 mmol) was added. The mixture was stirred at room temperature for 3 hours and then at 50° C. for 1 hour and then the solvent was removed. The residue was partitioned between water and ethyl acetate. The organic layer was separated and the aqueous layer was extracted with ethyl acetate. The combined organic layers were washed with water and brine, dried over magnesium sulfate and evaporated to dryness. The resulting crude was purified by flash chromatography (gradient from hexane to 30% hexane/ethyl acetate) to yield the title compound (1.40 g, 89%) as a pale solid.

LRMS (m/z): 448 (M+1)$^+$.

Preparation 10

Tert-butyl (3R)-3-[(6-chloro-2-pyrazolo[1,5-a]pyridin-3-ylpyrimidin-4-yl)amino]piperidine-1-carboxylate a) 2-Pyrazolo[1,5-a]pyridin-3-ylpyrimidine-4,6-diol

To an ice-bath cooled solution of sodium methoxide (prepared from 0.77 g of metal sodium in 30 mL methanol were added pyrazolo[1,5-a]pyridine-3-carboximidamide chlorohydrate (Preparation 1 b, 1.68 g, 8.54 mmol) and diethyl malonate (3.16 mL, 20.8 mmol). The mixture was stirred at room temperature overnight. Excess sodium meythoxyde (0.200 g of sodium in 10 mL of methanol) and diethyl malonate (1 mL, 9.75 mmol) were added and the mixture was stirred for an additional 24 hours. The solvent was removed under reduced pressure and the residue was redissolved in water (50 mL). After stirring for 30 minutes the solution was using a 2N hydrochloric acid solution. The precipitate was filtered, washed with water and dried under vacuum to yield the title compound (993 mg, 51%) as a pale solid.

LRMS (m/z): 229 (M+1)$^+$.

b) 3-(4,6-Dichloropyrimidin-2-yl)pyrazolo[1,5-a]pyridine

Obtained as a solid (69%) from 2-pyrazolo[1,5-a]pyridin-3-ylpyrimidine-4,6-diol (Preparation 10a) and phosphorus (V) oxychloride following the experimental procedure as described in Preparation 1d.

LRMS (m/z): 265 (M+1)$^+$.

c) Tert-butyl (3R)-3-[(6-chloro-2-pyrazolo[1,5-a]pyridin-3-ylpyrimidin-4-yl)amino]piperidine-1-carboxylate Tert-butyl (3R)-3-aminopiperidine-1-carboxylate (716 mg, 3.58 mmol) was added to a solution of 3-(4,6-dichloropyrimidin-2-yl)pyrazolo[1,5-a]pyridine (Preparation 10b, 790 mg, 2.98 mmol) and triethylamine (623 µL, 4.46 mmol) in ethanol (20 mL) and the resulting mixture was stirred at reflux temperature for 64 hours. After cooling to room temperature, the solvent was evaporated under reduced pressure. The residue was redissolved in ethyl acetate and the solution was washed with water and brine, dried over magnesium sulfate, filtered and evaporated in vacuo. The resulting crude was purified by flash chromatography (gradient from chloroform to 5% chloroform/methanol) to yield the title compound (1.22 g, 95%) as a white solid.

LRMS (m/z): 430 (M+1)$^+$.

EXAMPLES

Example 1

(Trans-4-{[5-fluoro-6-(4-hydroxypiperidin-1-yl)-2-pyrazolo[1,5-a]pyridin-3-ylpyrimidin-4-yl]amino}cyclohexyl)acetonitrile A suspension of {trans-4-[(6-chloro-5-fluoro-2-pyrazolo[1,5-a]pyridin-3-ylpyrimidin-4-yl)amino]cyclohexyl}acetonitrile (Preparation 2, 0.060 g, 0.16 mmol) and piperidin-4-ol (0.063 g, 0.62 mmol) in N,N'-dimethylacetamide (0.3 mL) was stirred at 100° C. for 3 hours. The reaction mixture was cooled to room temperature, poured into water and extracted with ethyl acetate. The combined organic layers were washed with water, brine, dried over magnesium sulfate and concentrated in vacuo. The crude was purified by flash chromatography (gradient from dichloromethane to dichloromethane/methanol 95:5) to yield the title compound (0.045 mg, 64%) as a yellow solid.

LRMS (m/z): 450 (M+1)$^+$.

$^1$H-NMR δ (300 MHz, DMSO-d$_6$): 1.18-1.50 (m, 6H), 1.57-1.72 (m, 1H), 1.78-1.93 (m, 4H), 1.97-2.09 (m, 2H), 3.11-3.28 (m, 2H), 3.62-3.78 (m, 1H), 3.86-3.98 (m, 1H), 3.98-4.15 (m, 2H), 4.72 (d, 1H), 6.64-6.74 (m, 1H), 6.94-7.06 (m, 1H), 7.36-7.47 (m, 1H), 8.40 (d, 1H), 8.46 (s, 1H), 8.75 (d, 1H).

Example 2

(Trans-4-{[6-(4-aminopiperidin-1-yl)-5-fluoro-2-pyrazolo[1,5-a]pyridin-3-ylpyrimidin-4-yl]amino}cyclohexyl)acetonitrile a) Tert-butyl[1-(6-{[trans-4-(cyanomethyl)cyclohexyl]amino}-5-fluoro-2-pyrazolo[1,5-a]pyridin-3-ylpyrimidin-4-yl)piperidin-4-yl]carbamate A mixture of (S)-6-chloro-5-fluoro-N-(1-(5-fluoropyridin-2-yl)ethyl)-2-(pyrazolo[1,5-a]pyridin-3-yl)pyrimidin-4-amine (Preparation 2, 0.080 g, 0.21 mmol), tert-butyl piperidin-4-ylcarbamate (0.060 g, 0.30 mmol) and sodium hydrogencarbonate (0.070 g, 0.83 mmol) in N,N-dimethylacetamide (0.5 mL) was stirred overnight at 100° C. After cooling to room temperature, water was added and the solid formed was filtered and dried in vacuo to yield the title compound (0.095 g, 79%).

LRMS (m/z): 551 (M+1)$^+$.

b) (Trans-4-{[6-(4-aminopiperidin-1-yl)-5-fluoro-2-pyrazolo[1,5-a]pyridin-3-ylpyrimidin-4-yl]amino}cyclohexyl)acetonitrile 4.0 M Solution of hydrogen chloride in 1,4-dioxane (0.5 mL, 2.60 mmol) was added to a solution of tert-butyl

[1-(6-{[trans-4-(cyanomethyl)cyclohexyl]amino}-5-fluoro-2-pyrazolo[1,5-a]pyridin-3-ylpyrimidin-4-yl)piperidin-4-yl] carbamate (Example 2a, 0.095 g, 0.17 mmol) and the resulting mixture was stirred at room temperature for 5 hours. The solvent was evaporated to dryness and the residue was diluted with water. The pH was adjusted to 9 by addition of 2N aqueous sodium hydroxide solution, extracted with dichloromethane (×3), the combined organic layers were washed with brine, dried and the solvent was evaporated to dryness. The resulting crude was purified by flash chromatography (gradient from dichloromethane to dichloromethane/methanol/ammonia 100:8:1) to yield the title compound (0.029 g, 37%) as a beige solid.

LRMS (m/z): 449 (M+1)$^+$.

$^1$H-NMR δ (300 MHz, CDCl$_3$): 1.20-1.53 (m, 6H), 1.70-1.85 (m, 1H), 1.87-2.07 (m, 4H), 2.25-2.41 (m, 4H), 2.88-3.13 (m, 3H), 3.92-4.16 (m, 1H), 4.32-4.46 (m, 2H), 4.52 (dd, 1H), 6.79-6.87 (m, 1H), 7.22-7.32 (m, 1H), 8.40-8.52 (m, 2H), 8.55 (s, 1H).

Example 3

{Trans-4-[(5-fluoro-6-piperazin-1-yl-2-pyrazolo[1,5-a]pyridin-3-ylpyrimidin-4-yl)amino]cyclohexyl}acetonitrile a) Tert-butyl 4-(6-{[trans-4-(cyanomethyl)cyclohexyl]amino}-5-fluoro-2-pyrazolo[1,5-a]pyridin-3-ylpyrimidin-4-yl)piperazine-1-carboxylate Obtained as a solid (60%) from {trans-4-[(6-chloro-5-fluoro-2-pyrazolo[1,5-a]pyridin-3-ylpyrimidin-4-yl)amino]cyclohexyl}acetonitrile (Preparation 2) and tert-butyl piperazine-1-carboxylate following the experimental procedure as described in Example 2a.

LRMS (m/z): 535 (M+1)$^+$.

b) {Trans-4-[(5-fluoro-6-piperazin-1-yl-2-pyrazolo[1,5-a]pyridin-3-ylpyrimidin-4-yl)amino]cyclohexyl}acetonitrile Obtained as a solid (47%) from tert-butyl 4-(6-{[trans-4-(cyanomethyl)cyclohexyl]amino}-5-fluoro-2-pyrazolo[1,5-a]pyridin-3-ylpyrimidin-4-yl)piperazine-1-carboxylate (Example 3a) following the experimental procedure as described in Example 2b.

LRMS (m/z): 435 (M+1)$^+$.

$^1$H-NMR δ (300 MHz, CDCl$_3$): 1.17-1.49 (m, 5H), 1.92-2.08 (m, 2H), 2.25-2.39 (m, 4H), 2.94-3.11 (m, 4H), 3.65-3.77 (m, 4H), 3.95-4.12 (m, 1H), 4.53 (dd, 1H), 6.77-6.88 (m, 1H), 7.22-7.31 (m, 1H), 8.40-8.51 (m, 2H), 8.54 (s, 1H).

Example 4

[Trans-4-({6-[4-(dimethylamino)piperidin-1-yl]-5-fluoro-2-pyrazolo[1,5-a]pyridin-3-ylpyrimidin-4-yl}amino)cyclohexyl]acetonitrile Obtained as a solid (33%) from {trans-4-[(6-chloro-5-fluoro-2-pyrazolo[1,5-a]pyridin-3-ylpyrimidin-4-yl)amino]cyclohexyl}acetonitrile (Preparation 2) and N,N-dimethylpiperidin-4-amine following the experimental procedure as described in Example 2a followed by purification of the crude product by flash chromatography (gradient from dichloromethane to dichloromethane/methanol/ammonia 100:8:1).

LRMS (m/z): 477 (M+1)$^+$.

$^1$H-NMR δ (300 MHz, CDCl$_3$): 1.17-1.46 (m, 4H), 1.60-1.81 (m, 2H), 1.90-2.09 (m, 4H), 2.27-2.40 (m, 4H), 2.34 (s, 6H), 2.40-2.54 (m, 1H), 2.96 (t, 2H), 3.95-4.19 (m, 1H), 4.53 (d, 3H), 6.75-6.90 (m, 1H), 7.23-7.33 (m, 1H), 8.41-8.52 (m, 2H), 8.55 (s, 1H).

Example 5

(Trans-4-{[5-fluoro-6-(2-hydroxyethoxy)-2-pyrazolo[1,5-a]pyridin-3-ylpyrimidin-4-yl]amino}cyclohexyl)acetonitrile Ethylene glycol (0.32 mL, 5.83 mmol) was added to a suspension of potassium tert-butoxide (0.043 g, 0.38 mmol) in 1,4-dioxane (0.5 mL) and the resulting mixture was stirred at room temperature for 15 minutes. {Trans-4-[(6-chloro-5-fluoro-2-pyrazolo[1,5-a]pyridin-3-ylpyrimidin-4-yl)amino]cyclohexyl}acetonitrile (Preparation 2, 0.050 g, 0.13 mmol) was then added and the reaction mixture was stirred at 90° C. overnight. After cooling to room temperature, the reaction mixture was partitioned between water and ethyl acetate. The organic layer was separated and the aqueous layer was extracted with ethyl acetate. The combined organic layers were washed with brine, dried over magnesium sulfate and evaporated to dryness. The resulting crude was purified by flash chromatography (gradient from dichloromethane to dichloromethane/methanol 95:5) to yield the title compound (0.035 g, 65%) as a solid.

LRMS (m/z): 411 (M+1)$^+$.

$^1$H-NMR δ (300 MHz, CDCl$_3$): 1.20-1.50 (m, 4H), 1.69-1.89 (m, 1H), 1.97-2.09 (m, 2H), 2.26-2.42 (m, 4H), 3.11-3.29 (m, 1H), 3.98-4.14 (m, 3H), 4.64-4.81 (m, 3H), 6.84-6.92 (m, 1H), 7.29-7.38 (m, 1H), 8.35-8.54 (m, 2H), 8.55 (s, 1H).

Example 6

{Trans-4-[(6-{[(2S)-2,3-dihydroxypropyl]oxy}-5-fluoro-2-pyrazolo[1,5-a]pyridin-3-ylpyrimidin-4-yl)amino]cyclohexyl}acetonitrile a) {Trans-4-[(6-{[(4R)-2,2-dimethyl-1,3-dioxolan-4-yl]methoxy}-5-fluoro-2-pyrazolo[1,5-a]pyridin-3-ylpyrimidin-4-yl)amino]cyclohexyl}acetonitrile Obtained as a solid (51%) from {trans-4-[(6-chloro-5-fluoro-2-pyrazolo[1,5-a]pyridin-3-ylpyrimidin-4-yl)amino]cyclohexyl}acetonitrile (Preparation 2) and [(4R)-2,2-dimethyl-1,3-dioxolan-4-yl]methanol following the experimental procedure as described in Example 5.

LRMS (m/z): 481 (M+1)$^+$.

b) {Trans-4-[(6-{[(2S)-2,3-dihydroxypropyl]oxy}-5-fluoro-2-pyrazolo[1,5-a]pyridin-3-ylpyrimidin-4-yl)amino]cyclohexyl}acetonitrile To a solution of {trans-4-[(6-{[(4R)-2,2-dimethyl-1,3-dioxolan-4-yl]methoxy}-5-fluoro-2-pyrazolo[1,5-a]pyridin-3-ylpyrimidin-4-yl)amino]cyclohexyl}acetonitrile (Example 6a, 0.051 g, 0.11 mmol) in tetrahydrofurane (1 mL), 1M hydrochloric acid solution (1 mL, 1 mmol) and the resulting solution was stirred at room temperature for 3 hours. The solvent was evaporated to dryness, the pH of the resulting solution was adjusted to 8 by addition of saturated aqueous solution of sodium hydrogencarbonate, extracted with ethyl acetate (×3), the combined organic layers were washed with brine, dried and the solvent was evaporated in vacuo to yield the title compound (0.036 g, 76%) as a yellow solid.

LRMS (m/z): 441 (M+1)+.

¹H-NMR δ (300 MHz, CDCl₃): 1.43 (m, 3H), 1.80 (m, 1H), 2.05 (m, 2H), 2.42 (m, 4H), 3.80 (m, 2H), 4.12 (m, 2H), 4.73 (d, 2H), 4.82 (d, 1H), 6.91 (m, 1H), 7.40 (dd, 1H), 8.44 (d, 1H), 8.55 (m, 2H).

Example 7

{Trans-4-[(6-{[(2R)-2,3-dihydroxypropyl]oxy}-5-fluoro-2-pyrazolo[1,5-a]pyridin-3-ylpyrimidin-4-yl)amino]cyclohexyl}acetonitrile a) {Trans-4-[(6-{[(4S)-2,2-dimethyl-1,3-dioxolan-4-yl]methoxy}-5-fluoro-2-pyrazolo[1,5-a]pyridin-3-ylpyrimidin-4-yl)amino]cyclohexyl}acetonitrile Obtained as a solid (71%) from {trans-4-[(6-chloro-5-fluoro-2-pyrazolo[1,5-a]pyridin-3-ylpyrimidin-4-yl)amino]cyclohexyl}acetonitrile (Preparation 2) and [(4S)-2,2-dimethyl-1,3-dioxolan-4-yl]methanol following the experimental procedure as described in Example 5.

LRMS (m/z): 481 (M+1)+.

b) {Trans-4-[(6-{[(2R)-2,3-dihydroxypropyl]oxy}-5-fluoro-2-pyrazolo[1,5-a]pyridin-3-yl pyrimidin-4-yl)amino]cyclohexyl}acetonitrile Obtained as a light yellow solid (70%) from {trans-4-[(6-{[(4S)-2,2-dimethyl-1,3-dioxolan-4-yl]methoxy}-5-fluoro-2-pyrazolo[1,5-a]pyridin-3-ylpyrimidin-4-yl)amino]cyclohexyl}acetonitrile (Example 7a) following the experimental procedure as described in Example 6b.

LRMS (m/z): 441 (M+1)+.

¹H-NMR δ (400 MHz, CDCl₃): 1.35 (m, 4H), 1.78 (m, 1H), 2.02 (m, 2H), 2.31 (m, 2H), 2.36 (d, 2H), 2.48 (t, 1H), 3.75 (m, 3H), 4.07 (m, 2H), 4.63 (d, 2H), 4.75 (d, 1H), 6.87 (m, 1H), 7.33 (m, 1H), 8.41 (d, 1H), 8.51 (m, 2H).

Example 8

[Trans-4-({5-fluoro-6-[(2-hydroxyethyl)amino]-2-pyrazolo[1,5-a]pyridin-3-ylpyrimidin-4-yl}amino)cyclohexyl]acetonitrile Obtained as a light yellow solid (41%) from {trans-4-[(6-{[(4R)-2,2-dimethyl-1,3-dioxolan-4-yl]methoxy}-5-fluoro-2-pyrazolo[1,5-a]pyridin-3-ylpyrimidin-4-yl)amino]cyclohexyl}acetonitrile (Preparation 2) and 2-aminoethanol following the experimental procedure as described in Example 2a followed by purification of the crude product by flash chromatography (gradient from dichloromethane to dichloromethane/methanol 95:5).

LRMS (m/z): 410 (M+1)+.

¹H-NMR δ (300 MHz, CDCl₃): 1.16-1.51 (m, 4H), 1.72-1.88 (m, 1H), 1.96-2.12 (m, 2H), 2.25-2.44 (m, 4H), 3.66-3.83 (m, 2H), 3.86-3.95 (m, 2H), 3.99-4.13 (m, 1H), 4.26 (br. s., 1H), 4.48 (d, 1H), 5.03 (br. s., 1H), 6.86 (t, 1H), 7.33 (d, 1H), 8.41-8.54 (m, 2H), 8.56 (s, 1H).

Example 9

[trans-4-({6-[2-(dimethylamino)ethoxy]-5-fluoro-2-pyrazolo[1,5-a]pyridin-3-ylpyrimidin-4-yl}amino)cyclohexyl]acetonitrile Obtained as a light yellow solid (56%) from {trans-4-[(6-{[(4R)-2,2-dimethyl-1,3-dioxolan-4-yl]methoxy}-5-fluoro-2-pyrazolo[1,5-a]pyridin-3-ylpyrimidin-4-yl)amino]cyclohexyl}acetonitrile (Preparation 2) and 2-(dimethylamino)ethanol following the experimental procedure as described in Example 5 followed by purification of the crude product by flash chromatography (gradient from dichloromethane to dichloromethane/methanol 95:5).

LRMS (m/z): 438 (M+1)+.

¹H-NMR δ (300 MHz, CDCl₃): 1.16-1.52 (m, 3H), 1.62-1.86 (m, 5H), 1.94-2.13 (m, 2H), 2.23-2.50 (m, 7H), 2.87 (t, 2H), 3.80-4.21 (m, 1H), 4.66 (t, 2H), 6.81-6.96 (m, 1H), 7.26-7.39 (m, 2H), 8.43-8.65 (m, 2H).

Example 10

[Trans-4-({6-[2-(dimethylamino)ethoxy]-5-fluoro-2-pyrazolo[1,5-a]pyridin-3-ylpyrimidin-4-yl}amino)cyclohexyl]acetonitrile Obtained as a white solid (42%) from {trans-4-[(6-{[(4R)-2,2-dimethyl-1,3-dioxolan-4-yl]methoxy}-5-fluoro-2-pyrazolo[1,5-a]pyridin-3-ylpyrimidin-4-yl)amino]cyclohexyl}acetonitrile (Preparation 2) and 3-(dimethylamino)propan-1-ol following the experimental procedure as described in Example 5 followed by purification of the crude product by flash chromatography (gradient from dichloromethane to dichloromethane/methanol 95:5).

LRMS (m/z): 453 (M+1)+.

¹H-NMR δ (300 MHz, CDCl₃): 1.05-1.45 (m, 4H), 1.50-1.83 (m, 7H), 1.89-2.10 (m, 3H), 2.25 (s, 5H), 2.38-2.55 (m, 2H), 3.86-4.16 (m, 1H), 4.31-4.70 (m, 2H), 6.68-6.93 (m, 1H), 7.07-7.39 (m, 2H), 8.08-8.72 (m, 2H).

Example 11

6-(4-Aminopiperidin-1-yl)-5-fluoro-N-[(1S)-1-(5-fluoropyridin-2-yl)ethyl]-2-pyrazolo[1,5-a]pyridin-3-ylpyrimidin-4-amine a) Tert-butyl[1-(5-fluoro-6-{[(1S)-1-(5-fluoropyridin-2-yl)ethyl]amino}-2-pyrazolo[1,5-a]pyridine-3-ylpyrimidin-4-yl)piperidin-4-yl]carbamate Obtained as a solid (60%) from (S)-6-chloro-5-fluoro-N-(1-(5-fluoropyridin-2-yl)ethyl)-2-(pyrazolo[1,5-a]pyridin-3-yl)pyrimidin-4-amine (Preparation 4) and tert-butyl piperidin-4-ylcarbamate following the experimental procedure as described in Example 2a followed by purification of the crude product by flash chromatography (gradient from dichloromethane to dichloromethane/methanol 95:5).

LRMS (m/z): 551 (M+1)+.

b) 6-(4-Aminopiperidin-1-yl)-5-fluoro-N-[(1S)-1-(5-fluoropyridin-2-yl)ethyl]-2-pyrazolo[1,5-a]pyridin-3-ylpyrimidin-4-amine Obtained as a solid (68%) from tert-butyl [1-(5-fluoro-6-{[(1S)-1-(5-fluoropyridin-2-yl)ethyl]amino}-2-pyrazolo[1,5-a]pyridin-3-ylpyrimidin-4-yl)piperidin-4-yl]carbamate (Example 11a) following the experimental procedure as described in Example 2b.

LRMS (m/z): 451 (M+1)+.

¹H-NMR δ (300 MHz, CDCl₃): 1.33-1.54 (m, 3H), 1.65 (s, 3H), 1.85-2.10 (m, 3H), 2.88-3.26 (m, 3H), 4.41 (d, 2H), 5.36-5.51 (m, 1H), 5.60 (d, 1H), 6.81 (t, 1H), 7.17-7.26 (m, 1H), 7.31-7.47 (m, 2H), 8.28 (d, 1H), 8.43-8.55 (m, 2H).

Example 12

2-[(5-Fluoro-6-{[(1S)-1-(5-fluoropyrimidin-2-yl) ethyl]amino}-2-pyrazolo[1,5-a]pyridin-3-ylpyrimidin-4-yl)oxy]ethanol Obtained as a solid (26%) from 6-chloro-5-fluoro-N-[(1S)-1-(5-fluoropyrimidin-2-yl)ethyl]-2-pyrazolo[1,5-a]pyridin-3-ylpyrimidin-4-amine (Preparation 5) and ethylene glycol following the experimental procedure as described in Example 5.

LRMS (m/z): 414 (M+1)$^+$.

$^1$H-NMR δ (300 MHz, CDCl$_3$): 1.72 (d, 3H), 3.08-3.37 (m, 1H), 4.04 (d, 2H), 4.55-4.79 (m, 2H), 5.50-5.73 (m, 1H), 6.01 (d, 1H), 6.79-6.97 (m, 1H), 7.28-7.43 (m, 1H), 8.38-8.68 (m, 5H).

Example 13

(2S)-3-[(5-fluoro-6-{[(1S)-1-(5-fluoropyrimidin-2-yl)ethyl]amino}-2-pyrazolo[1,5-a]pyridin-3-ylpyrimidin-4-yl)oxy]propane-1,2-diol a) 6-{[(4R)-2,2-dimethyl-1,3-dioxolan-4-yl]methoxy}-5-fluoro-N-[(1S)-1-(5-fluoropyrimidin-2-yl)ethyl]-2-pyrazolo[1,5-a]pyridin-3-ylpyrimidin-4-amine Obtained as a solid (77%) from 6-chloro-5-fluoro-N-[(1S)-1-(5-fluoropyrimidin-2-yl)ethyl]-2-pyrazolo[1,5-a]pyridin-3-ylpyrimidin-4-amine (Preparation 5) and (R)-(2,2-dimethyl-1,3-dioxolan-4-yl)methanol following the experimental procedure as described in Example 5.

LRMS (m/z): 484 (M+1)$^+$.

b) (2S)-3-[(5-fluoro-6-{[(1S)-1-(5-fluoropyrimidin-2-yl)ethyl]amino}-2-pyrazolo[1,5-a]pyridin-3-ylpyrimidin-4-yl)oxy]propane-1,2-diol Obtained as a white solid (12%) from 6-{[(4R)-2,2-dimethyl-1,3-dioxolan-4-yl]methoxy}-5-fluoro-N-[(1S)-1-(5-fluoropyrimidin-2-yl)ethyl]-2-pyrazolo[1,5-a]pyridin-3-ylpyrimidin-4-amine (Example 13a) following the experimental procedure as described in Example 6b.

LRMS (m/z): 444 (M+1)$^+$.

$^1$H-NMR δ (300 MHz, CDCl$_3$): 1.72 (d, 3H), 3.56-3.92 (m, 2H), 4.15 (br. s., 1H), 4.65 (d, 2H), 5.49-5.77 (m, 1H), 6.00-6.26 (m, 1H), 6.88 (t, 1H), 7.35 (t, 1H), 8.26-8.77 (m, 5H).

Example 14

3-((3R)-3-{[5-fluoro-6-(2-hydroxyethoxy)-2-pyrazolo[1,5-a]pyridin-3-ylpyrimidin-4-yl]amino}piperidin-1-yl)-3-oxopropanenitrile a) Tert-butyl(3R)-3-{[5-fluoro-6-(2-hydroxyethoxy)-2-pyrazolo[1,5-a]pyridin-3-ylpyrimidin-4-yl]amino}piperidine-1-carboxylate Obtained as an orange solid (76%) from tert-butyl (3R)-3-[(6-chloro-5-fluoro-2-pyrazolo[1,5-a]pyridin-3-ylpyrimidin-4-yl) amino]piperidine-1-carboxylate (Preparation 5) and ethylene glycol following the experimental procedure as described in Example 5.

LRMS (m/z): 473 (M+1)$^+$.

b) 2-({5-Fluoro-6-[(3R)-piperidin-3-ylamino]-2-pyrazolo[1,5-a]pyridin-3-ylpyrimidin-4-yl}oxy)ethanol To a solution of tert-butyl (3R)-3-{[5-fluoro-6-(2-hydroxyethoxy)-2-pyrazolo[1,5-a]pyridin-3-ylpyrimidin-4-yl] amino}piperidine-1-carboxylate (Example 14a, 0.16 g, 0.34 mmol) in 1,4-dioxane (1 mL), 4.0 M solution of hydrogen chloride in 1,4-dioxane (1.30 mL, 5.2 mmol) was added. The resulting mixture was stirred at room temperature for 5 hours and evaporated in vacuo to yield the dihydrochloride salt of the title compound (0.15 g, 93%) as a yellow solid.

LRMS (m/z): 373 (M+1)$^+$.

c) 3-((3R)-3-{[5-fluoro-6-(2-hydroxyethoxy)-2-pyrazolo[1,5-a]pyridin-3-ylpyrimidin-4-yl]amino}piperidin-1-yl)-3-oxopropanenitrile Obtained as a light yellow solid (38%) from 2-({5-fluoro-6-[(3R)-piperidin-3-ylamino]-2-pyrazolo[1,5-a]pyridin-3-ylpyrimidin-4-yl}oxy)ethanol (Example 15b) following the experimental procedure as described in Preparation 7. The crude was purified by flash chromatography (gradient from dichloromethane to dichloromethane/methanol 95:5).

LRMS (m/z): 440 (M+1)$^+$.

$^1$H-NMR δ (300 MHz, CDCl$_3$): 1.71-2.08 (m, 3H), 2.15-2.32 (m, 1H), 2.67-2.85 (m, 1H), 2.97-3.15 (m, 1H), 3.26-3.52 (m, 3H), 3.55-3.74 (m, 2H), 3.78-3.99 (m, 1H), 4.00-4.13 (m, 1H), 4.19-4.36 (m, 2H), 4.59-4.73 (m, 3H), 4.76-4.91 (m, 1H), 6.80-7.01 (m, 1H), 7.33-7.48 (m, 1H), 8.29-8.66 (m, 3H).

Example 15

3-{(3R)-3-[(6-butoxy-5-fluoro-2-pyrazolo[1,5-a]pyridin-3-ylpyrimidin-4-yl)amino]piperidin-1-yl}-3-oxopropanenitrile a) Tert-butyl(3R)-3-[(6-butoxy-5-fluoro-2-pyrazolo[1,5-a]pyridin-3-ylpyrimidin-4-yl)amino]piperidine-1-carboxylate Metal sodium (0.058 g, 2.52 mmol) was added to butan-1-ol (7 mL) and the mixture was stirred at room temperature until metal sodium was consumed. Tert-butyl (3R)-3-[(6-chloro-5-fluoro-2-pyrazolo[1,5-a]pyridin-3-ylpyrimidin-4-yl)amino]piperidine-1-carboxylate (Preparation 5, 0.25 g, 0.56 mmol) was added, the reaction mixture was stirred overnight at 90° C., then cooled to room temperature and partitioned between water and ethyl acetate. The organic layer was separated and the aqueous layer was extracted twice with ethyl acetate, the combined organic layers were washed with brine, dried and concentrated in vacuo. The resulting crude was purified by flash chromatography (gradient from hexanes to dichloromethane) to yield the title compound (0.174 g, 64%) as a solid.

LRMS (m/z): 485 (M+1)$^+$.

b) 6-Butoxy-5-fluoro-N-[(3R)-piperidin-3-yl]-2-pyrazolo[1,5-a]pyridin-3-ylpyrimidin-4-amine Obtained as a yellow solid dihydrochloride salt (100%) from tert-butyl (3R)-3-[(6-butoxy-5-fluoro-2-pyrazolo[1,5- a]pyridin-3-ylpyrimidin-4-yl)amino]piperidine-1-carboxylate (Example 15a) following the experimental procedure as described in Example 14b.
LRMS (m/z): 385 (M+1)$^+$.

c) 3-{(3R)-3-[(6-butoxy-5-fluoro-2-pyrazolo[1,5-a]pyridin-3-ylpyrimidin-4-yl)amino]piperidin-1-yl}-3-oxopropanenitrile Obtained as a light yellow solid (58%) from 6-butoxy-5-fluoro-N-[(3R)-piperidin-3-yl]-2-pyrazolo[1,5-a]pyridin-3-ylpyrimidin-4-amine (Example 15b) following the experimental procedure as described in Preparation 7b. The crude was purified by flash chromatography (gradient from dichloromethane to dichloromethane/methanol 95:5).
LRMS (m/z): 452 (M+1)$^+$.
$^1$H-NMR δ (300 MHz, CDCl$_3$): 0.96-1.10 (m, 3H), 1.26 (s, 2H), 1.47-1.69 (m, 2H), 1.69-2.01 (m, 4H), 2.11-2.30 (m, 1H), 2.93 (d, 1H), 3.22-3.47 (m, 2H), 3.52-3.73 (m, 1H), 3.78-4.02 (m, 1H), 4.15-4.31 (m, 1H), 4.45-4.60 (m, 2H), 4.63-4.82 (m, 1H), 6.82-6.98 (m, 1H), 7.30-7.42 (m, 1H), 8.33-8.70 (m, 3H).

Example 16

3-((3R)-3-{[6-(2-ethoxyethoxy)-5-fluoro-2-pyrazolo[1,5-a]pyridin-3-ylpyrimidin-4-yl]amino}piperidin-1-yl)-3-oxopropanenitrile a) Tert-butyl (3R)-3)-5-fluoro-2-pyrazolo[1,5-a]pyri-{[6-(2-ethoxyethoxy din-3-ylpyrimidin-4-yl] amino}piperidine-1-carboxylate Obtained as a colourless oil (81%) from tert-butyl (3R)-3-[(6-chloro-5-fluoro-2-pyrazolo[1,5-a]pyridin-3-ylpyrimidin-4-yl) amino]piperidine-1-carboxylate (Preparation 5) and 2-ethoxyethanol following the experimental procedure as described in Example 5.
LRMS (m/z): 501 (M+1)$^+$.

b) 6-(2-Ethoxyethoxy)-5-fluoro-N-[(3R)-piperidin-3-yl]-2-pyrazolo[1,5-a]pyridin-3-ylpyrimidin-4-amine Obtained as a light yellow solid (100%) from tert-butyl (3R)-3)-5-fluoro-2-pyrazolo[1,5-a]pyri-{[6-(2-ethoxyethoxydin-3-ylpyrimidin-4-yl]amino}piperidine-1-carboxylate (Example 16a) following the experimental procedure as described in Example 15b.
LRMS (m/z): 401 (M+1)$^+$.

c) 3-((3R)-3-{[6-(2-ethoxyethoxy)-5-fluoro-2-pyrazolo[1,5-a]pyridin-3-ylpyrimidin-4-yl] amino}piperidin-1-yl)-3-oxopropanenitrile Obtained as a light yellow solid (60%) from 6-(2-ethoxyethoxy)-5-fluoro-N-[(3R)-piperidin-3-yl]-2-pyrazolo[1,5-a]pyridin-3-ylpyrimidin-4-amine (Example 16b) following the experimental procedure as described in Preparation 7b. The crude was purified by flash chromatography (gradient from dichloromethane to dichloromethane/methanol 95:5).
LRMS (m/z): 468 (M+1)$^+$.
$^1$H-NMR δ (300 MHz, CDCl$_3$): 0.73-1.01 (m, 1H), 1.14-1.36 (m, 4H), 1.69-2.08 (m, 3H), 2.13-2.30 (m, 1H), 2.93 (d, 1H), 3.19-3.47 (m, 2H), 3.54-3.74 (m, 3H), 3.77-4.02 (m, 2H), 4.12-4.32 (m, 1H), 4.59-4.87 (m, 3H), 6.79-6.98 (m, 1H), 7.29-7.43 (m, 1H), 8.33-8.68 (m, 3H).

Example 17

3-[(3R)-3-({5-Fluoro-6-[4-(hydroxymethyl)phenyl]-2-pyrazolo[1,5-a]pyridin-3-ylpyrimidin-4-yl}amino) piperidin-1-yl]-3-oxopropanenitrile A Schlenk tube was charged with from 3-{(3R)-3-[(6-chloro-5-fluoro-2-pyrazolo[1,5-a]pyridin-3-ylpyrimidin-4-yl)amino]piperidin-1-yl}-3-oxopropanenitrile (Preparation 7b, 0.35 g, 0.85 mmol), 4-hydroxymethylphenylboronic acid (0.19 g, 1.28 mmol), 2.0 M aqueous sodium carbonate solution (0.64 mL, 1.28 mmol) and 1,2-dimethoxyethane (4 mL). The Schlenk tube was subjected to three cycles of evacuation-backfilling with argon and then tetrakis(triphenylphosphine)palladium(0) (99 mg, 0.09 mmol) was added. After three further cycles of evacuation-backfilling with argon, the Schlenk tube was sealed and the mixture was stirred and heated at 80° C. overnight. The solvent was removed and the residue was purified by flash chromatography (gradient from hexanes to hexanes/ethyl acetate 1:9) to yield the title compound (0.32 g, 77%) as a white solid.
LRMS (m/z): 486 (M+1)$^+$.
$^1$H-NMR δ (300 MHz, CDCl$_3$): 1.71-1.90 (m, 2H), 2.10-2.35 (m, 2H), 3.21-3.54 (m, 4H), 3.63-3.70 (m, 1H), 3.91 (dd, 1H), 4.30 (br.s., 2H), 4.62 (dd, 1H), 4.81 (t, 2H), 5.10 (bs, 1H), 6.94 (dt, 1H), 7.33-7.45 (m, 1H), 7.53-7.62 (m, 2H), 8.10 (d, 2H), 8.54-8.26 (m, 2H), 8.70 (s, 1H).

Example 18

3-((3R)-3-{[6-(6-Aminopyridin-3-yl)-5-fluoro-2-pyrazolo[1,5-a]pyridin-3-ylpyrimidin-4-yl] amino}piperidin-1-yl)-3-oxopropanenitrile Obtained as a solid (44%) from 3-{(3R)-3-[(6-chloro-5-fluoro-2-pyrazolo[1,5-a]pyridin-3-ylpyrimidin-4-yl)amino] piperidin-1-yl}-3-oxopropanenitrile (Preparation 6b) and 5-(4,4,5,5-tetramethyl-1,3,2-dioxaborolan-2-yl)pyridin-2-amine following the experimental procedure as described in Example 18 followed by purification of the crude product by flash chromatography (gradient from dichloromethane to dichloromethane/methanol 95:5).
LRMS (m/z): 472 (M+1)$^+$.
$^1$H-NMR δ (300 MHz, CDCl$_3$): 1.70-2.07 (m, 3H), 2.16-2.30 (m, 1H), 3.33-3.54 (m, 4H), 3.84-4.04 (m, 1H), 4.23-4.41 (m, 1H), 4.74 (d, 2H), 4.96-5.15 (m, 1H), 6.57-6.69 (m, 1H), 6.78-6.96 (m, 1H), 7.32-7.44 (m, 1H), 8.26 (d, 1H), 8.48-8.59 (m, 2H), 8.65 (d, 1H), 8.93 (dd, 1H).

Example 19

3-((3R)-3-{[5-fluoro-6-(6-methoxypyridin-3-yl)-2-pyrazolo[1,5-a]pyridin-3-ylpyrimidin-4-yl] amino}piperidin-1-yl)-3-oxopropanenitrile Obtained as a solid (42%) from 3-{(3R)-3-[(6-chloro-5-fluoro-2-pyrazolo[1,5-a]pyridin-3-ylpyrimidin-4-yl)amino] piperidin-1-yl}-3-oxopropanenitrile (Preparation 6b) and (6-methoxypyridin-3-yl)boronic acid following the experimental procedure as described in Example 18 followed by purification of the crude product by flash chromatography (gradient from dichloromethane to dichloromethane/methanol 95:5).
LRMS (m/z): 487 (M+1)$^+$.

¹H-NMR δ (400 MHz, CDCl₃): 1.68-2.08 (m, 3H), 2.18-2.33 (m, 1H), 3.13-3.52 (m, 4H), 3.57-3.72 (m, 1H), 3.87-3.99 (m, 1H), 4.05 (s, 3H), 4.27-4.44 (m, 1H), 5.09 (d, 1H), 6.85-6.97 (m, 2H), 7.34-7.44 (m, 1H), 8.38 (dd, 1H), 8.49-8.60 (m, 2H), 8.67 (d, 1H), 8.98-9.06 (m, 1H).

Example 20

3-((3R)-3-{[5-fluoro-6-(2-methylpyridin-4-yl)-2-pyrazolo[1,5-a]pyridin-3-ylpyrimidin-4-yl]amino}piperidin-1-yl)-3-oxopropanenitrile a) tert-Butyl(3R)-3-{[5-fluoro-6-(2-methylpyridin-4-yl)-2-pyrazolo[1,5-a]pyridin-3-ylpyrimidin-4-yl]amino}piperidine-1-carboxylate To a solution of tert-butyl (3R)-3-[(6-chloro-5-fluoro-2-pyrazolo[1,5-a]pyridin-3-ylpyrimidin-4-yl)amino]piperidine-1-carboxylate (1.0 g, 2.24 mmol), (2-methylpyridin-4-yl)boronic acid (0.46 g, 3.36 mmol) and 0.18 g (0.22 mmol) of [1,1'-Bis(diphenylphosphino)ferrocene]dichloropalladium (II) complex with dichloromethane in dioxane (50 mL) was added a 2M aqueous solution of cesium carbonate (3.36 mL). The resulting mixture was stirred at 90° C. under nitrogen atmosphere overnight, then cooled to room temperature, filtered through Celite®, the solvent was removed and the residue was purified first by flash chromatography (dichloromethane to dichloromethane/methanol 90:10) and then by reverse phase chromatography (C-18 silica from Waters®, water/1:1 acetonitrile-methanol as eluents [0.1% v/v ammonium formate buffered] 0% to 100%) to yield the title compound (0.827 g, 73%) as a light yellow solid.

LRMS (m/z): 504 (M+1)⁺.

b) 5-Fluoro-6-(2-methylpyridin-4-yl)-N-[(3R)-piperidin-3-yl]-2-pyrazolo[1,5-a]pyridin-3-ylpyrimidin-4-amine To a solution of tert-butyl (3R)-3-{[5-fluoro-6-(2-methylpyridin-4-yl)-2-pyrazolo[1,5-a]pyridin-3-ylpyrimidin-4-yl]amino}piperidine-1-carboxylate (Example 20a, 0.087 g, 0.17 mmol) in dichloromethane (5 mL) was added trifluoroacetic acid (1.5 mL) and the resulting mixture was stirred at room temperature overnight. The volatiles were evaporated under reduced pressure and the residue was partitioned between water and dichloromethane. The aqueous layer was separated and the pH was adjusted with diluted solution of sodium hydroxide until it reached basic pH. The product was extracted with dichloromethane (×3) and the combined organic layers were washed with brine, dried over magnesium sulfate and evaporated to dryness to yield the title compound (0.064 g, 92%) as a light yellow solid.

LRMS (m/z): 404 (M+1)⁺.

c) 3-((3R)-3-{[5-Fluoro-6-(2-methylpyridin-4-yl)-2-pyrazolo[1,5-a]pyridin-3-ylpyrimidin-4-yl]amino}piperidin-1-yl)-3-oxopropanenitrile Obtained as a light yellow solid (66%) from 5-fluoro-6-(2-methylpyridin-4-yl)-N-[(3R)-piperidin-3-yl]-2-pyrazolo[1,5-a]pyridin-3-ylpyrimidin-4-amine (Example 20b) following the experimental procedure as described in Preparation 6b. The crude was purified by flash chromatography (gradient from dichloromethane to dichloromethane/methanol 90:10).

LRMS (m/z): 471 (M+1)⁺.

¹H-NMR δ (400 MHz, CDCl₃): 1.80-2.31 (m, 5H), 2.68-2.85 (m, 3H), 3.20-4.61 (m, 7H), 5.14-5.35 (m, 1H), 6.85-6.98 (m, 1H), 7.35-7.45 (m, 1H), 7.82-8.04 (m, 2H), 8.43-8.77 (m, 4H).

Example 21

3-{(3R)-3-[[5-fluoro-6-(2-methylpyridin-4-yl)-2-pyrazolo[1,5-a]pyridin-3-ylpyrimidin-4-yl](methyl)amino]piperidin-1-yl}-3-oxopropanenitrile a) Tert-butyl(3R)-3-[[5-fluoro-6-(2-methylpyridin-4-yl)-2-pyrazolo[1,5-a]pyridin-3-ylpyrimidin-4-yl]methyl)amino]piperidine-1-carboxylate To a solution of tert-butyl(3R)-3-{[5-fluoro-6-(2-methylpyridin-4-yl)-2-pyrazolo[1,5-a]pyridin-3-ylpyrimidin-4-yl]amino}piperidine-1-carboxylate (Example 20a, 0.218 g, 0.43 mmol) in N,N-dimethylformamide (2 mL) was added sodium hydride (60% dispersion in mineral oil, 0.034 g, 1.42 mmol). The resulting suspension was stirred at room temperature for 15 min. and then methyl iodide (0.040 mL, 0.64 mmol) were added. The mixture was stirred for 2 hours and then it was partitioned between water and ethyl acetate. The organic layer was separated and washed with water and brine, dried over magnesium sulfate, filtered and the solvents were removed under reduced pressure to give 196 mg (88% yield) of the title compound as a light yellow solid.

LRMS (m/z): 518 (M+1)⁺.

b) 5-Fluoro-N-methyl-6-(2-methylpyridin-4-yl)-N-[(3R)-piperidin-3-yl]-2-pyrazolo[1,5-a]pyridin-3-ylpyrimidin-4-amine Obtained as a light yellow solid (94%) from tert-butyl (3R)-3-[[5-fluoro-6-(2-methylpyridin-4-yl)-2-pyrazolo[1,5-a]pyridin-3-ylpyrimidin-4-yl](methyl)amino]piperidine-1-carboxylate (Example 21a) following the experimental procedure as described in Example 20b.

LRMS (m/z): 418 (M+1)⁺.

c) 3-{(3R)-3-[[5-Fluoro-6-(2-methylpyridin-4-yl)-2-pyrazolo[1,5-a]pyridin-3-ylpyrimidin-4-yl]methyl)amino]piperidin-1-yl}-3-oxopropanenitrile Obtained as a pale white solid (56%) from 5-fluoro-N-methyl-6-(2-methylpyridin-4-yl)-N-[(3R)-piperidin-3-yl]-2-pyrazolo[1,5-a]pyridin-3-ylpyrimidin-4-amine (Example 21b) following the experimental procedure as described in Example 20c. The crude was purified by reverse phase chromatography (C-18 silica from Waters®, water/1:1 acetonitrile-methanol as eluents [0.1% v/v ammonium formate buffered] 0% to 100%).

LRMS (m/z): 418 (M+1)⁺.

¹H-NMR δ (400 MHz, CDCl₃): 1.65-2.27 (m, 6H), 2.79-3.06 (m, 4H), 3.10-3.65 (m, 6H), 3.73-3.91 (m, 1H), 4.46-4.92 (m, 2H), 6.86-7.04 (m, 1H), 7.30-7.51 (m, 1H), 7.98-8.26 (m, 2H), 8.40 (d, 1H), 8.50-8.75 (m, 3H).

Example 22

1-(5-Fluoro-6-{[(3R)-1-glycoloylpiperidin-3-yl]amino}-2-pyrazolo[1,5-a]pyridin-3-ylpyrimidin-4-yl)piperidin-4-ol A suspension of 2-{(3R)-3-[(6-chloro-5-fluoro-2-pyrazolo[1,5-a]pyridin-3-ylpyrimidin-4-yl)amino]piperidin-1- yl}-2-oxoethanol (Preparation 7, 0.060 g, 0.15 mmol) and piperidin-4-ol (0.060 g, 0.59 mmol) in N,N'-dimethylacetamide (0.3 mL) was stirred at 110° C. for 2 hours. The reaction mixture was cooled to room temperature, poured into water and extracted with ethyl acetate. The combined organic layers were washed with water, brine, dried over magnesium sulfate and concentrated in vacuo. The crude was purified by flash chromatography (gradient from dichloromethane to dichloromethane/methanol 95:5) to yield the title compound (0.046 mg, 62%) as a yellow solid.

LRMS (m/z): 470 (M+1)$^+$.

$^1$H-NMR δ (300 MHz, CDCl$_3$): 1.66-1.95 (m, 4H), 1.97-2.09 (m, 2H), 2.11-2.28 (m, 1H), 2.98-3.35 (m, 3H), 3.41-3.59 (m, 2H), 3.64-3.81 (m, 1H), 3.84-4.06 (m, 3H), 4.16-4.32 (m, 5H), 4.54-4.71 (m, 1H), 6.75-6.93 (m, 1H), 7.17-7.37 (m, 1H), 8.39 (d, 2H), 8.44-8.53 (m, 1H), 8.58 (d, 1H).

Example 23

2-[(3R)-3-({5-Fluoro-6-[4-(hydroxymethyl)piperidin-1-yl]-2-pyrazolo[1,5-a]pyridin-3-ylpyrimidin-4-yl}amino)piperidin-1-yl]-2-oxoethanol Obtained as a yellow solid (54%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and piperidin-4-ylmethanol following the experimental procedure as described in Example 22.

LRMS (m/z): 484 (M+1)$^+$.

$^1$H-NMR δ (300 MHz, CDCl$_3$): 1.30-1.51 (m, 3H), 1.68-1.95 (m, 6H), 2.05-2.24 (m, 1H), 2.93-3.29 (m, 4H), 3.36-3.61 (m, 4H), 3.62-3.80 (m, 1H), 3.83-4.07 (m, 1H), 4.14-4.29 (m, 2H), 4.51 (d, 2H), 4.58-4.71 (m, 1H), 6.75-6.95 (m, 1H), 7.20-7.33 (m, 1H), 8.37-8.52 (m, 2H), 8.53-8.64 (m, 1H).

Example 24

2-[(3R)-3-({5-Fluoro-6-[(2-hydroxyethyl)amino]-2-pyrazolo[1,5-a]pyridin-3-ylpyrimidin-4-yl}amino)piperidin-1-yl]-2-oxoethanol Obtained as a solid (28%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and 2-amino ethanol following the experimental procedure as described in Example 22.

LRMS (m/z): 431 (M+1)$^+$.

$^1$H-NMR δ (300 MHz, CDCl$_3$): 1.67-1.80 (m, 2H), 1.78-1.93 (m, 1H), 2.08-2.26 (m, 1H), 2.99-3.31 (m, 1H), 3.34-3.58 (m, 2H), 3.59-3.83 (m, 3H), 3.84-4.06 (m, 3H), 4.09-4.32 (m, 3H), 4.47-4.72 (m, 2H), 4.97-5.17 (m, 1H), 6.77-6.94 (m, 1H), 7.28-7.36 (m, 1H), 8.29-8.62 (m, 3H).

Example 25

2-((3R)-3-{[5-fluoro-6-(4-methylpiperazin-1-yl)-2-pyrazolo[1,5-a]pyridin-3-ylpyrimidin-4-yl]amino}piperidin-1-yl)-2-oxoethanol Obtained as a beige solid (61%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and 1-methylpiperazine following the experimental procedure as described in Example 22.

LRMS (m/z): 469 (M+1)$^+$.

$^1$H-NMR δ (300 MHz, CDCl$_3$): 1.26-1.38 (m, 1H), 1.71-1.96 (m, 3H), 2.10-2.24 (m, 1H), 2.36 (s, 3H), 2.48-2.58 (m, 3H), 2.93-3.31 (m, 2H), 3.35-3.55 (m, 1H), 3.62-3.84 (m, 5H), 3.86-4.06 (m, 2H), 4.13-4.29 (m, 2H), 4.53-4.71 (m, 1H), 6.76-6.90 (m, 1H), 7.22-7.35 (m, 1H), 8.30-8.64 (m, 3H).

Example 26

2-{(3R)-3-[(5-Methyl-6-morpholin-4-yl-2-pyrazolo[1,5-a]pyridin-3-ylpyrimidin-4-yl)amino]piperidin-1-yl}-2-oxoethanol a) Tert-butyl(3R)-3-[(5-methyl-6-morpholin-4-yl-2-pyrazolo[1,5-a]pyridin-3-ylpyrimidin-4-yl)amino]piperidine-1-carboxylate A mixture of tert-butyl(3R)-3-[(6-chloro-5-methyl-2-pyrazolo[1,5-a]pyridin-3-ylpyrimidin-4-yl)amino]piperidine-1-carboxylate (Preparation 8c) and morfoline was heated for 48 hours at 100° C. The reaction mixture was cooled to room temperature and poured into water. The resulting precipitate was filtered off, washed with water and dried under vacuum to yield the title compound (0.13 g, 59%) as a yellow solid.

LRMS (m/z): 494 (M+1)$^+$.

b) 5-Methyl-6-morpholin-4-yl-N-[(3R)-piperidin-3-yl]-2-pyrazolo[1,5-a]pyridin-3-ylpyrimidin-4-amine Obtained as a yellow solid dihydrochloride salt (100%) from tert-butyl(3R)-3-[(5-methyl-6-morpholin-4-yl-2-pyrazolo[1,5-a]pyridin-3-ylpyrimidin-4-yl)amino]piperidine-1-carboxylate (Example 26a) following the experimental procedure as described in Example 14b.

LRMS (m/z): 394 (M+1)$^+$.

c) 2-{(3R)-3-[(5-Methyl-6-morpholin-4-yl-2-pyrazolo[1,5-a]pyridin-3-ylpyrimidin-4-yl)amino]piperidin-1-yl}-2-oxoethanol Obtained as a solid (43%) from 5-methyl-6-morpholin-4-yl-N-[(3R)-piperidin-3-yl]-2-pyrazolo[1,5-a]pyridin-3-ylpyrimidin-4-amine (Example 26b) following the experimental procedure as described in Preparation 7. The crude was purified by flash chromatography (gradient from dichloromethane to dichloromethane/methanol 95:5).

LRMS (m/z): 452 (M+1)$^+$.

$^1$H-NMR δ (300 MHz, CDCl$_3$): 1.67-1.93 (m, 4H), 2.00 (s, 3H), 2.09-2.30 (m, 1H), 3.08-3.44 (m, 5H), 3.44-4.02 (m, 7H), 4.11-4.61 (m, 4H), 6.70-6.98 (m, 1H), 7.15-7.42 (m, 1H), 8.33-8.78 (m, 3H).

Example 27

2-((3R)-3-{[6-(2-Methoxyethoxy)-5-methyl-2-pyrazolo[1,5-a]pyridin-3-ylpyrimidin-4-yl]amino}piperidin-1-yl)-2-oxoethanol a) Tert-butyl (3R)-3-{[6-(2-methoxyethoxy)-5-methyl-2-pyrazolo[1,5-a]pyridin-3-ylpyrimidin-4-yl]amino}piperidine-1-carboxylate Obtained as a colourless oil (65%) from (3R)-3-[(6-chloro-5-methyl-2-pyrazolo[1,5-a]pyridin-3-ylpyrimidin-4- yl)amino]piperidine-1-carboxylate (Preparation 9c) and 2-methoxyethanol following the experimental procedure as described in Example 5.

LRMS (m/z): 483 (M+1)$^+$.

b) Methoxyethoxy)-5-methyl-N-[(3R)-piperidin-3-yl]-2-pyrazolo[1,5-a]pyridin-3-ylpyrimidin-4-amine Obtained as a yellowish solid dihydrochloride salt (98%) from tert-butyl (3R)-3-{[6-(2-methoxyethoxy)-5-methyl-2-pyrazolo[1,5-a]pyridin-3-ylpyrimidin-4-yl]amino}piperidine-1-carboxylate (Example 27a) following the experimental procedure as described in Example 15b.

LRMS (m/z): 383 (M+1)$^+$.

c) 2-((3R)-3-{[6-(2-Methoxyethoxy)-5-methyl-2-pyrazolo[1,5-a]pyridin-3-ylpyrimidin-4-yl]amino}piperidin-1-yl)-2-oxoethanol Obtained as a white solid (23%) from methoxyethoxy)-5-methyl-N-[(3R)-piperidin-3-yl]-2-pyrazolo[1,5-a]pyridin-3-ylpyrimidin-4-amine (Example 27b) following the experimental procedure as described in Preparation 7. The crude was purified by flash chromatography (gradient from dichloromethane to dichloromethane/methanol 95:5).

LRMS (m/z): 441 (M+1)$^+$.

$^1$H-NMR δ (300 MHz, CDCl$_3$): 0.78-1.21 (m, 2H), 1.68-1.89 (m, 3H), 1.96 (s, 3H), 2.09-2.27 (m, 1H), 3.06-3.28 (m, 1H), 3.34-3.58 (m, 4H), 3.63-4.01 (m, 4H), 4.09-4.44 (m, 3H), 4.53-4.71 (m, 2H), 6.75-6.96 (m, 1H), 7.21-7.35 (m, 1H), 8.40-8.77 (m, 3H).

Example 28

Ethyl 1-(5-fluoro-6-{[(3R)-1-glycoloylpiperidin-3-yl]amino}-2-pyrazolo[1,5-a]pyridin-3-ylpyrimidin-4-yl)-4-methylpiperidine-4-carboxylate Obtained as a deep yellow solid (58%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and ethyl 4-methylpiperidine-4-carboxylate following the experimental procedure as described in Example 2a followed by purification of the crude product by flash chromatography (gradient from dichloromethane to dichloromethane/methanol 95:5).

LRMS (m/z): 540 (M+1)$^+$.

$^1$H-NMR δ (300 MHz, CDCl$_3$): 1.14-1.39 (m, 5H), 1.49-1.67 (m, 6H), 1.68-1.98 (m, 4H), 2.13-2.38 (m, 2H), 3.06-3.63 (m, 3H), 3.62-4.08 (m, 3H), 4.08-4.36 (m, 4H), 4.50-4.80 (m, 1H), 6.77-6.95 (m, 1H), 6.78-6.97 (m, 1H), 7.26-7.38 (m, 1H), 8.28-8.60 (m, 3H).

Example 29

2-((3R)-3-{[5-Fluoro-2-(5-methylpyrazolo[1,5-a]pyridin-3-yl)-6-morpholin-4-ylpyrimidin-4-yl]amino}piperidin-1-yl)-2-oxoethanol a) 1-Amino-4-methylpyridin-1-ium 2,4,6-trimethylbenzenesulfonate

A solution of O-(mesitylsulfonyl)hydroxylamine (23.11 g, 107.4 mmol) in dichloromethane (272 mL) was added dropwise to a cooled (0° C.) solution of 4-methylpyridine (10.0 g, 107.4 mmol) in dichloromethane (136 mL) and the resulting mixture was stirred for 2 hours at room temperature. The solvent was partially evaporated and diethyl ether was added to precipitate an oil. The reaction mixture was cooled to 0° C. and the solvents were decanted. The oil was dried under vacuum to yield the title compound (33.11 g, 99%).

LRMS (m/z): 109 (M)$^+$.

$^1$H-NMR δ (300 MHz, CDCl$_3$): 2.22 (s, 3H), 2.42 (s, 3H), 2.61 (s, 6H), 6.80 (s, 2H), 7.26-7.39 (d, 2H), 8.84-8.86 (d, 2H).

b) Ethyl 5-methylpyrazolo[1,5-a]pyridine-3-carboxylate

Obtained as a solid (54%) from 1-amino-4-methylpyridin-1-ium 2,4,6-trimethylbenzene sulfonate (Example 29a) and ethyl propiolate following the experimental procedure as described in Preparation 1a followed by purification of the crude product by flash chromatography (hexanes/ethyl acetate).

LRMS (m/z): 205 (M+1)$^+$.

$^1$H-NMR δ (300 MHz, CDCl$_3$): 1.38-1.42 (t, 3H), 2.46 (s, 3H), 4.34-4.40 (q, 2H), 6.75-6.77 (d, 1H), 7.92 (s, 1H), 8.33 (s, 1H), 8.37-8.39 (d, 1H).

c) 5-Methylpyrazolo[1,5-a]pyridine-3-carboximidamide 2.0 M Trimethylaluminium solution in toluene (62 mL, 124 mmol) was added dropwise to a cooled (0° C.) suspension of ammonium chloride (6.18 g, 115.6 mmol) in toluene (133 mL) and the resulting mixture was stirred until no more gas was formed. A solution of ethyl 5-methylpyrazolo[1,5-a]pyridine-3-carboxylate (Example 29b, 7.87 g, 38.53 mmol) in toluene (25 mL) was then added dropwise and the reaction mixture was stirred overnight at 80° C. Additional ammonium chloride (6.18 g, 115.6 mmol) and 2.0 M trimethylaluminium solution in toluene (62 mL, 124 mmol) were added and the suspension was stirred overnight at 80° C. and a weekend at room temperature. The reaction mixture was cooled at 0° C. and methanol (30 mL) was added dropwise. The suspension was filtered over diatomaceous earth (Celite®) and the solid was washed with methanol. The organic phases were combined, solvents were partially evaporated (up to 100 mL of solution) and dichloromethane (100 mL) was added. The solid formed was filtered and the solvents were evaporated to dryness. Purification of the residue by flash chromatography (dichloromethane/methanol) gave the title compound (6.7 g, 98%).

LRMS (m/z): 175 (M+1)$^+$.

$^1$H-NMR δ (300 MHz, DMSO-d6): 2.50 (s, 3H), 7.08-7.10 (d, 1H), 7.88 (s, 1H), 8.65 (s, 1H), 8.81-8.83 (d, 1H), 8.97 (bs, 3H).

d) 5-Fluoro-2-(5-methylpyrazolo[1,5-a]pyridin-3-yl)pyrimidine-4,6-diol

Obtained as a yellow solid (80%) from 5-methylpyrazolo[1,5-a]pyridine-3-carboximidamide (Example 29c) and diethyl 2-fluoromalonate following the experimental procedure as described in Preparation 4a.

LRMS (m/z): 261 (M+1)$^+$.

$^1$H-NMR δ (400 MHz, DMSO-d$_6$): 2.50 (s, 3H), 6.99-7.01 (d, 1H), 8.47 (s, 1H), 8.71-8.73 (d, 1H), 8.82 (s, 1H), 12.59 (bs, 1H).

e) 3-(4,6-Dichloro-5-fluoropyrimidin-2-yl)-5-methylpyrazolo[1,5-a]pyridine

A mixture of 5-fluoro-2-(5-methylpyrazolo[1,5-a]pyridin-3-yl)pyrimidine-4,6-diol (Example 29d, 1.19 g, 4.57 mmol) and phosphorus(V) oxychloride (9.3 mL, 99.6 mmol) was stirred at 110° C. for 75 minutes. The solvent was removed under reduced pressure and water was added. The precipitate was filtered, washed with water and dried under vacuum to yield the title compound (1.08 g, 79%) as a yellow solid.

LRMS (m/z): 297 (M+1)$^+$.

$^1$H-NMR δ (400 MHz, CDCl$_3$): 2.51 (s, 3H), 6.78-6.80 (d, 1H), 8.23 (s, 1H), 8.41-8.43 (d, 1H), 8.62 (s, 1H).

f) Tert-butyl(3R)-3-{[6-chloro-5-fluoro-2-(5-methyl-pyrazolo[1,5-a]pyridin-3-yl)pyrimidin-4-yl] amino}piperidine-1-carboxylate Obtained as a pink solid (93%) from 3-(4,6-dichloro-5-fluoropyrimidin-2-yl)-5-methylpyrazolo[1,5-a]pyridine (Example 29e) and (R)-tert-butyl 3-aminopiperidine-1-carboxylate following the experimental procedure described in Preparation 5.

LRMS (m/z): 460 (M+1)$^+$.

g) Tert-butyl(3R)-3-{[5-fluoro-2-(5-methylpyrazolo [1,5-a]pyridin-3-yl)-6-morpholin-4-ylpyrimidin-4-yl]amino}piperidine-1-carboxylate Obtained as a solid (47%) from tert-butyl (3R)-3-{[6-chloro-5-fluoro-2-(5-methylpyrazolo[1,5-a]pyridin-3-yl)pyrimidin-4-yl]amino}piperidine-1-carboxylate (Example 29f) and morfoline following the experimental procedure described in Example 32a followed by purification by flash chromatography (gradient from hexanes to ethyl acetate).

LRMS (m/z): 512 (M+1)$^+$.

h) 5-Fluoro-2-(5-methylpyrazolo[1,5-a]pyridin-3-yl)-6-morpholin-4-yl-N-[(3R)-piperidin-3-yl] pyrimidin-4-amine Obtained as a solid (85%) from tert-butyl (3R)-3-{[5-fluoro-2-(5-methylpyrazolo[1,5-a]pyridin-3-yl)-6-morpholin-4-ylpyrimidin-4-yl]amino}piperidine-1-carboxylate (Example 29g) following the experimental procedure as described in Example 15b.

LRMS (m/z): 412 (M+1)$^+$.

i) 2-((3R)-3-{[5-Fluoro-2-(5-methylpyrazolo[1,5-a] pyridin-3-yl)-6-morpholin-4-ylpyrimidin-yl] amino}piperidin-1-yl)-2-oxoethanol Obtained as a deep yellow solid (40%) from 5-fluoro-2-(5-methylpyrazolo[1,5-a]pyridin-3-yl)-6-morpholin-4-yl-N-[(3R)-piperidin-3-yl]pyrimidin-4-amine (Example 29h) following the experimental procedure as described in Preparation 7. The crude was purified by flash chromatography (gradient from hexanes to ethyl acetate).

LRMS (m/z): 470 (M+1)$^+$.

$^1$H-NMR δ (300 MHz, CDCl$_3$): 1.66-1.81 (m, 2H), 1.80-1.99 (m, 1H), 2.09-2.27 (m, 1H), 2.41 (s, 3H), 3.09-3.29 (m, 2H), 3.32-3.58 (m, 1H), 3.65-3.79 (m, 5H), 3.81-3.90 (m, 4H), 3.92-4.04 (m, 1H), 4.11-4.34 (m, 2H), 4.47-4.75 (m, 1H), 6.60-6.75 (m, 1H), 8.07-8.62 (m, 3H).

Example 30

Ethyl 1-(6-{[(3R)-1-(cyanoacetyl)piperidin-3-yl] amino}-5-fluoro-2-pyrazolo[1,5-a]pyridin-3-ylpyrimidin-4-yl)piperidine-4-carboxylate Obtained as a solid (48%) from 3-{(3R)-3-[(6-chloro-5-fluoro-2-pyrazolo[1,5-a]pyridin-3-ylpyrimidin-4-yl)amino]piperidin-1-yl}-3-oxopropanenitrile (Preparation 7b) and ethyl piperidine-4-carboxylate following the experimental procedure as described in Example 2a followed by purification of the crude product by flash chromatography (gradient from dichloromethane to dichloromethane/methanol 95:5).

LRMS (m/z): 535 (M+1)$^+$.

$^1$H-NMR δ (300 MHz, CDCl$_3$): 1.29 (t, 3H), 1.66-2.12 (m, 7H), 2.10-2.28 (m, 1H), 2.50-2.72 (m, 1H), 3.01-3.27 (m, 3H), 3.31-3.69 (m, 4H), 3.75-3.92 (m, 1H), 4.07-4.29 (m, 2H), 4.33-4.46 (m, 2H), 4.47-4.77 (m, 1H), 6.75-6.95 (m, 1H), 7.32 (d, 1H), 8.25-8.59 (m, 3H).

Example 31

1-(6-{[(3R)-1-(Cyanoacetyl)piperidin-3-yl]amino}-5-fluoro-2-pyrazolo[1,5-a]pyridin-3-ylpyrimidin-4-yl)piperidine-4-carboxylic acid To a solution of ethyl 1-(6-{[(3R)-1-(cyanoacetyl)piperidin-3-yl]amino}-5-fluoro-2-pyrazolo[1,5-a]pyridin-3-ylpyrimidin-4-yl)piperidine-4-carboxylate (Example 30, 0.046 g, 0.08 mmol) in a mixture of tetrahydrofuran and water (1:1) (1.4 mL), lithium hydroxide monohydrate (0.014 g, 0.34 mmol) was added and the mixture was stirred at room temperature for 2 hours. The solvent was evaporated in vacuo, water was added and the pH of the aqueous solution was adjusted to 3 by addition of 0.5 N hydrochloric acid. The aqueous solution was extracted with dichloromethane (×3), the combined organic layers were washed with brine, dried over magnesium sulfate and evaporated to dryness to yield the title compound (0.019 g, 40%) as a brown solid.

LRMS (m/z): 507 (M+1)$^+$.

$^1$H-NMR δ (300 MHz, CDCl$_3$): 1.63-2.25 (m, 6H), 2.55-2.81 (m, 1H), 3.07-3.31 (m, 3H), 3.30-3.67 (m, 4H), 3.70-3.93 (m, 2H), 4.12-4.30 (m, 1H), 4.32-4.47 (m, 2H), 4.47-4.86 (m, 1H), 6.76-7.00 (m, 1H), 7.29-7.45 (m, 1H), 8.27-8.66 (m, 3H).

Example 32

2-((3R)-3-{[5-Fluoro-2-pyrazolo[1,5-a]pyridin-3-yl-6-(1H-pyrazol-4-yl)pyrimidin-4-yl]amino}piperidin-1-yl)-2-oxoethanol A Schlenk tube was charged with 2-{(3R)-3-[(6-chloro-5-fluoro-2-pyrazolo[1,5-a]pyridin-3-ylpyrimidin-4-yl) amino]piperidin-1-yl}-2-oxoethanol (Preparation 7, 0.047 g, 0.12 mmol), 4-(4,4,5,5-tetramethyl-1,3,2-dioxaborolan-2-yl)-1H-pyrazole (0.034 g, 0.18 mmol), 2M aqueous solution of potassium triphosphate (0.17 mL, 0.35 mmol) and 1,4-dioxane (0.5 mL). The Schlenk tube was subjected to three cycles of evacuation-backfilling with argon and then [1,1'-bis(diphenylphosphino) ferrocene]palladium(II) dichloride complex with dichloromethane (0.01 g, 0.01 mmol) was added. After three further cycles of evacuation-backfilling with argon, the Schlenk tube was sealed and the mixture was stirred overnight at 90° C. The reaction mixture was cooled to room temperature and more 4-(4,4,5,5-tetramethyl-1,3,2-dioxaborolan-2-yl)-1H-pyrazole (0.034 g, 0.18 mmol) and [1,1'-bis(diphenylphosphino) ferrocene]palladium(II) dichloride complex with dichloromethane (0.01 g, 0.01 mmol) were added. After three cycles of evacuation-backfilling, the mixture was stirred at 90° C. for 6 hours. The mixture was cooled to room temperature, filtered through Celite®, the solvent was removed and the residue was purified by flash chromatography (dichloromethane to dichloromethane/methanol 95:5) to yield the title compound (0.018 g, 35%) as a light yellow solid.

LRMS (m/z): 437 (M+1)$^+$.

$^1$H-NMR δ (300 MHz, CDCl$_3$): 1.47-1.76 (m, 2H), 2.11-2.33 (m, 1H), 3.10-3.31 (m, 1H), 3.37-3.55 (m, 1H), 3.68-3.82 (m, 4H), 3.91-4.10 (m, 1H), 4.19-4.30 (m, 2H), 4.29-4.71 (m, 1H), 4.92-5.08 (m, 1H), 6.82-6.99 (m, 1H), 7.30-7.42 (m, 1H), 8.33 (br. s., 2H), 8.49-8.62 (m, 2H), 8.69 (d, 1H).

Example 33

1-[4-(5-Fluoro-6-{[(3R)-1-glycoloylpiperidin-3-yl]amino}-2-pyrazolo[1,5-a]pyridin-3-ylpyrimidin-4-yl)-1H-pyrazol-1-yl]-2-methylpropan-2-ol a) 2-Methyl-1-[4-(4,4,5,5-tetramethyl-1,3,2-dioxaborolan-2-yl)-1H-pyrazol-1-yl]propan-2-ol A microwave reactor was charged with 4-(4,4,5,5-tetramethyl-1,3,2-dioxaborolan-2-yl)-1H-pyrazole (0.50 g, 2.58 mmol), 2,2-dimethyloxirane (0.57 mL, 6.44 mmol), cesium carbonate (1.25 g, 3.84 mmol) and acetonitrile (5 mL). The reaction mixture was subjected to microwave irradiation for 1 hour at 130° C. The solid was filtered, washed with dichloromethane and the filtrate and washings were concentrated in vacuo to yield the title compound (0.28 g, 42%) as an oil.

b) 1-[4-(5-Fluoro-6-{[(3R)-1-glycoloylpiperidin-3-yl]amino}-2-pyrazolo[1,5-a]pyridin-3-yl pyrimidin-4-yl)-1H-pyrazol-1-yl]-2-methylpropan-2-ol Obtained as a solid (57%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and 2-methyl-1-[4-(4,4,5,5-tetramethyl-1,3,2-dioxaborolan-2-yl)-1H-pyrazol-1-yl]propan-2-ol (Example 33a) following the experimental procedure as described in Example 32.

LRMS (m/z): 509 (M+1)$^+$.

$^1$H-NMR δ (300 MHz, CDCl$_3$): 1.23 (s, 6H), 1.70-1.98 (m, 3H), 2.13-2.31 (m, 1H), 3.10-3.32 (m, 1H), 3.38-3.58 (m, 1H), 3.67-3.83 (m, 2H), 3.89-4.09 (m, 2H), 4.19 (d, 2H), 4.23-4.39 (m, 2H), 4.55-4.77 (m, 1H), 4.98 (t, 1H), 6.82-6.95 (m, 1H), 7.11-7.44 (m, 1H), 7.44-7.66 (m, 1H), 8.14 (s, 1H), 8.26 (d, 1H), 8.46-8.60 (m, 1H), 8.67 (d, 1H).

Example 34

2-((3R)-3-{[5-Fluoro-6-(2-methylpyridin-4-yl)-2-pyrazolo[1,5-a]pyridin-3-ylpyrimidin-4-yl]amino}piperidin-1-yl)-2-oxoethanol A Schlenk tube was charged with 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 8, 0.080 g, 0.20 mmol), (2-methylpyridin-4-yl)boronic acid (0.041 g, 0.30 mmol), 2M aqueous solution of cesium carbonate (0.29 mL), 0.59 mmol) and 1,4-dioxane (1 mL). The Schlenk tube was subjected to three cycles of evacuation-backfilling with argon and then [1,1'-bis(diphenylphosphino) ferrocene]palladium(II) dichloride complex with dichloromethane (0.01 g, 0.01 mmol) was added. After three further cycles of evacuation-backfilling with argon, the Schlenk tube was sealed and the mixture was stirred overnight at 90° C. The mixture was cooled to room temperature, filtered through Celite®, the solvent was removed and the residue was purified by flash chromatography (dichloromethane to dichloromethane/methanol 95:5) to yield the title compound (0.036 g, 39%) as a light orange solid.

LRMS (m/z): 462 (M+1)$^+$.

$^1$H-NMR δ (300 MHz, CDCl$_3$): 1.73-2.02 (m, 3H), 2.12-2.33 (m, 1H), 2.70 (s, 3H), 3.12-3.30 (m, 1H), 3.37-3.61 (m, 2H), 3.69-3.85 (m, 1H), 3.95-4.13 (m, 1H), 4.20-4.43 (m, 2H), 4.66 (dd, 1H), 5.16 (t, 1H), 6.85-6.98 (m, 1H), 7.31-7.44 (m, 1H), 7.80 (d, 1H), 7.87 (br. s., 1H), 8.47-8.61 (m, 2H), 8.63-8.80 (m, 2H).

Example 35

2-((3R)-3-{[5-Fluoro-6-(6-methoxypyridin-3-yl)-2-pyrazolo[1,5-a]pyridin-3-ylpyrimidin-4-yl]amino}piperidin-1-yl)-2-oxoethanol Obtained as a light yellow solid (58%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and (6-methoxypyridin-3-yl)boronic acid following the experimental procedure as described in Example 17 followed by purification by flash chromatography (gradient from dichloromethane to dichloromethane/methanol 95:5).

LRMS (m/z): 478 (M+1)$^+$.

$^1$H-NMR δ (300 MHz, CDCl$_3$): 0.74-0.97 (m, 2H), 1.00-1.34 (m, 1H), 1.70-2.03 (m, 3H), 2.13-2.33 (m, 1H), 3.11-3.31 (m, 1H), 3.34-3.51 (m, 1H), 3.51-3.85 (m, 1H), 4.05 (s, 3H), 4.13-4.43 (m, 2H), 4.70 (dd, 1H), 5.07 (t, 1H), 6.74-7.07 (m, 2H), 7.29-7.56 (m, 1H), 8.28-8.83 (m, 3H), 9.01 (s, 1H).

Example 36

2-((3R)-3-{[5-Fluoro-6-(6-methylpyridin-3-yl)-2-pyrazolo[1,5-a]pyridin-3-ylpyrimidin-4-yl]amino}piperidin-1-yl)-2-oxoethanol Obtained as a light yellow solid (61%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and (6-methylpyridin-3-yl)boronic acid following the experimental procedure as described in Example 17 followed by purification by flash chromatography (gradient from dichloromethane to dichloromethane/methanol 95:5).

LRMS (m/z): 462 (M+1)$^+$.

$^1$H-NMR δ (300 MHz, CDCl$_3$): 0.70-1.37 (m, 1H), 1.55-2.07 (m, 1H), 2.10-2.32 (m, 1H), 2.49 (s, 1H), 2.67 (s, 3H), 3.03-3.32 (m, 2H), 3.37-3.56 (m, 1H), 3.90-4.13 (m, 1H), 4.19-4.40 (m, 3H), 4.68 (dd, 1H), 5.03-5.25 (m, 1H), 6.76-7.21 (m, 1H), 7.29-7.42 (m, 2H), 8.28-8.40 (m, 1H), 8.50-8.81 (m, 3H), 9.28 (s, 1H).

Example 37

2-[(3R)-3-({5-Fluoro-6-[2-(hydroxymethyl)pyridin-4-yl]-2-pyrazolo[1,5-a]pyridin-3-ylpyrimidin-4-yl}amino)piperidin-1-yl]-2-oxoethanol a) 4-Bromo-2-[(tetrahydro-2H-pyran-2-yloxy)methyl]pyridine To a solution of (4-bromopyridin-2-yl)methanol (0.30 g, 1.60 mmol) in dichloromethane (8 mL) and tetrahydrofuran (4 mL), pyridinium para-toluenesulfonate (0.080 g, 0.32 mmol) and 3,4-dihydro-2H-pyran (0.32 mL, 3.51 mmol) were added. The reaction mixture was stirred at for 3.5 hours at 50° C. and for 60 hours at room temperature. The solvent was evaporated in vacuo and the residue was purified by flash chromatography (gradient from dichloromethane to dichloromethane/methanol 95:5) to yield the title compound (0.33 g, 76%) as a colorless oil.

LRMS (m/z): 272, 274 (M+1, M+3)⁺.

¹H-NMR δ (300 MHz, CDCl₃): 1.46-1.65 (m, 2H), 1.69-1.83 (m, 2H), 1.83-2.02 (m, 2H), 3.51-3.65 (m, 1H), 3.81-3.96 (m, 1H), 4.62 (d, 1H), 4.78 (t, 1H), 4.89 (d, 1H), 7.37 (d, 1H), 7.67 (s, 1H), 8.37 (d, 1H).

b) 2-[(Tetrahydro-2H-pyran-2-yloxy)methyl]-4-(4,4,5,5-tetramethyl-1,3,2-dioxaborolan-2-yl)pyridine A Schlenk tube was charged with 4-bromo-2-[(tetrahydro-2H-pyran-2-yloxy)methyl]pyridine (Example 37a, 0.32 g, 1.18 mmol), 4,4,4',4',5,5,5',5'-octamethyl-2,2'-bi-1,3,2-dioxaborolane (0.45 g, 1.76 mmol), potassium acetate (0.35 g, 3.53 mmol) and 1,4-dioxane (6 mL). The Schlenk tube was subjected to three cycles of evacuation-backfilling with argon and then [1,1'-bis (diphenylphosphino) ferrocene]palladium(II) dichloride (0.058 g, 0.07 mmol) was added. After three further cycles of evacuation-backfilling with argon, the Schlenk tube was sealed and the mixture was stirred and heated at 80° C. overnight. The mixture was cooled, filtered through diatomaceous earth (Celite®) and the solvent was concentrated to dryness to yield the title compound as a black oil (0.35 g, 93%).

LRMS (m/z): 238 (M+1)⁺.

c) 2-{(3R)-3-[(5-Fluoro-2-pyrazolo[1,5-a]pyridin-3-yl-6-{2-[(tetrahydro-2H-pyran-2-yloxy)methyl]pyridin-4-yl}pyrimidin-4-yl)amino]piperidin-1-yl}-2-oxoethanol Obtained as na Orange oil (59%) from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7) and 2-[(tetrahydro-2H-pyran-2-yloxy)methyl]-4-(4,4,5,5-tetramethyl-1,3,2-dioxaborolan-2-yl)pyridine (Example 37b) following the experimental procedure as described in Example 40.

LRMS (m/z): 562 (M+1)⁺.

d) 2-[(3R)-3-({5-Fluoro-6-[2-(hydroxymethyl)pyridin-4-yl]-2-pyrazolo[1,5-a]pyridin-3-ylpyrimidin-4-yl}amino)piperidin-1-yl]-2-oxoethanol To a solution of 2-{(3R)-3-[(5-fluoro-2-pyrazolo[1,5-a]pyridin-3-yl-6-{2-[(tetrahydro-2H-pyran-2-yloxy)methyl]pyridin-4-yl}pyrimidin-4-yl)amino]piperidin-1-yl}-2-oxoethanol (Example 37c, 0.055 g, 0.10 mmol) in tetrahydrofuran (0.3 mL), 1N hydrochloric acid (0.30 mL, 0.30 mmol) was added. The reaction mixture was stirred at room temperature for 4.5 hours, the solvent was concentrated in vacuo and saturated sodium bicarbonate aqueous solution was added until the pH was adjusted to 8. The mixture was extracted with ethyl acetate (×3), the combined organic layers were washed with brine, dried over magnesium sulfate and the solvent was evaporated to dryness. The crude was purified by preparative HPLC (gradient from water to methanol) to yield the title compound (0.022 g, 47%) as a yellow solid.

LRMS (m/z): 478 (M+1)⁺.

¹H-NMR δ (300 MHz, CDCl₃): 1.82-2.03 (m, 3H), 2.15-2.33 (m, 2H), 3.26 (dd, 2H), 3.35-3.58 (m, 1H), 3.94-4.13 (m, 1H), 4.20-4.46 (m, 2H), 4.65 (d, 1H), 4.91 (s, 2H), 5.11-5.27 (m, 1H), 6.92 (q, 1H), 7.31-7.45 (m, 1H), 7.85-8.03 (m, 2H), 8.43-8.61 (m, 2H), 8.61-8.84 (m, 2H).

Example 38

Ethyl 5-(5-fluoro-6-{[(3R)-1-glycoloylpiperidin-3-yl]amino}-2-pyrazolo[1,5-a]pyridin-3-ylpyrimidin-4-yl)pyridine-2-carboxylate a) Ethyl 5-(6-{[(3R)-1-(tert-butoxycarbonyl)piperidin-3-yl]amino}-5-fluoro-2-pyrazolo[1,5-a]pyridin-3-ylpyrimidin-4-yl)pyridine-2-carboxylate Obtained as a light yellow solid (72%) from tert-butyl 3-[(6-chloro-5-fluoro-2-pyrazolo[1,5-a]pyrimidin-4-yl)amino]piperidine-1-carboxylate (Preparation 5, 0.300 g, 0.67 mmol) and ethyl 5-(4,4,5,5-tetramethyl-1,3,2-dioxaborolan-2-yl)pyridine-2-carboxylate (0.600 g, 2.17 mmol) following the experimental procedure as described in Example 20a. The crude product was purified by flash chromatography (hexanes to hexanes/ethyl acetate 20:80).

LRMS (m/z): 562 (M+1)⁺.

b) Ethyl 5-{5-fluoro-6-[(3R)-piperidin-3-ylamino]-2-pyrazolo[1,5-a]pyridin-3-ylpyrimidin-4-yl}pyridine-2-carboxylate Obtained as a light yellow solid (89%) from ethyl 5-(6-{[(3R)-1-(tert-butoxycarbonyl)piperidin-3-yl]amino}-5-fluoro-2-pyrazolo[1,5-a]pyridin-3-ylpyrimidin-4-yl)pyridine-2-carboxylate (Example 38a) following the experimental procedure as described in Example 20b.

LRMS (m/z): 462 (M+1)⁺.

c) 5-(5-fluoro-6-{[(3R)-1-glycoloylpiperidin-3-yl]amino}-2-pyrazolo[1,5-a]pyridin-3-ylpyrimidin-4-yl)pyridine-2-carboxylate Obtained as a light yellow solid (72%) from ethyl 5-{5-fluoro-6-[(3R)-piperidin-3-ylamino]-2-pyrazolo[1,5-a]pyridin-3-ylpyrimidin-4-yl}pyridine-2-carboxylate (Example 38b) following the experimental procedure as described in Preparation 7. The crude was purified by flash chromatography (gradient from hexanes to ethyl acetate and then to ethyl acetate/ethanol 70:30).

LRMS (m/z): 520 (M+1)⁺.

¹H-NMR δ (400 MHz, CDCl₃): 1.44-1.53 (m, 3H), 1.69-2.29 (m, 4H), 3.11-3.53 (m, 3H), 3.69-4.41 (m, 5H), 4.47-4.59 (m, 2H), 5.09-5.29 (m, 1H), 6.82-6.97 (m, 1H), 7.29-7.41 (m, 1H), 8.22-8.35 (m, 1H), 8.45-8.81 (m, 4H), 9.53 (s, 1H).

Example 39

2-((3R)-3-{[5-Fluoro-6-(2-methoxyethoxy)-2-pyrazolo[1,5-a]pyridin-3-ylpyrimidin-4-yl]amino}piperidin-1-yl)-2-oxoethanol a) Tert-butyl (3R)-3-{[5-fluoro-6-(2-methoxyethoxy)-2-pyrazolo[1,5-a]pyridin-3-ylpyrimidin-4-yl]amino}piperidine-1-carboxylate 2-Methoxyethanol (0.11 mL, 1.45 mmol) was added to a suspension of sodium hydride (60% dispersion in mineral oil, 0.10 g, 1.13 mmol) in tetrahydrofurane (1.5 mL) and the mixture was stirred at room temperature for 1 hour. Tert-butyl (3R)-3-[(6-chloro-5-fluoro-2-pyrazolo[1,5-a]pyridin- 3-ylpyrimidin-4-yl)amino]piperidine-1-carboxylate (Preparation 5, 0.10 g, 0.22 mmol) was then added and the reaction mixture was stirred under reflux overnight. The reaction mixture was cooled to room temperature and partitioned between water and ethyl acetate. The organic layer was separated and the aqueous layer was extracted with ethyl acetate. The combined organic layers were washed with brine, dried over magnesium sulfate and concentrated in vacuo. The resulting crude was purified by flash chromatography (gradient from dichloromethane to dichloromethane/methanol 90:10) to yield the title compound (0.067 g, 60%) as a solid.
LRMS (m/z): 487 (M+1)+.

b) 5-Fluoro-6-(2-methoxyethoxy)-N-[(3R)-piperidin-3-yl]-2-pyrazolo[1,5-a]pyridin-3-ylpyrimidin-4-amine Obtained as a solid dihydrochloride salt (100%) from 5-fluoro-6-(2-methoxyethoxy)-N-[(3R)-piperidin-3-yl]-2-pyrazolo[1,5-a]pyridin-3-ylpyrimidin-4-amine (Example 39a) following the experimental procedure as described in Example 14b.
LRMS (m/z): 387 (M+1)+.

c) 2-((3R)-3-{[5-Fluoro-6-(2-methoxyethoxy)-2-pyrazolo[1,5-a]pyridin-3-ylpyrimidin-4-yl]amino}piperidin-1-yl)-2-oxoethanol Obtained as an off-white solid (47%) from 5-fluoro-6-(2-methoxyethoxy)-N-[(3R)-piperidin-3-yl]-2-pyrazolo[1,5-a]pyridin-3-ylpyrimidin-4-amine (Example 39b) following the experimental procedure as described in Preparation 7 followed by purification by flash chromatography (gradient from dichloromethane to dichloromethane/methanol 95:5).
LRMS (m/z): 445 (M+1)+.
$^1$H-NMR δ (300 MHz, CDCl$_3$): 1.69-2.01 (m, 4H), 2.12-2.30 (m, 1H), 2.91-3.23 (m, 1H), 3.31-3.44 (m, 1H), 3.48 (s, 3H), 3.54 (t, 1H), 3.68-3.78 (m, 1H), 3.80-3.90 (m, 2H), 3.96-4.08 (m, 1H), 4.14-4.32 (m, 2H), 4.62-4.84 (m, 3H), 6.78-6.96 (m, 1H), 7.29-7.39 (m, 1H), 8.33-8.54 (m, 2H), 8.60 (d, 1H).

Example 40

2-((3R)-3-{[5-Fluoro-6-(2-hydroxyethoxy)-2-pyrazolo[1,5-a]pyridin-3-ylpyrimidin-4-yl]amino}piperidin-1-yl)-2-oxoethanol a) Tert-butyl (3R)-3-{[5-fluoro-6-(2-hydroxyethoxy)-2-pyrazolo[1,5-a]pyridin-3-ylpyrimidin-4-yl]amino}piperidine-1-carboxylate Ethylene glycol (0.5 mL, 8.94 mmol) was added to a suspension of potassium tert-butoxide (0.08 g, 0.67 mmol) in 1,4-dioxane (0.7 mL) and the resulting mixture was stirred at room temperature for 15 minutes. Tert-butyl (3R)-3-[(6-chloro-5-fluoro-2-pyrazolo[1,5-a]pyridin-3-ylpyrimidin-4-yl)amino]piperidine-1-carboxylate (Preparation 5, 0.10 g, 0.22 mmol) was then added and the reaction mixture was stirred at 90° C. overnight. After cooling to room temperature, the reaction mixture was partitioned between water and ethyl acetate. The organic layer was separated and the aqueous layer was extracted with ethyl acetate. The combined organic layers were washed with brine, dried over magnesium sulfate and evaporated to dryness. The resulting crude was purified by flash chromatography (gradient from dichloromethane to dichloromethane/methanol 95:5) to yield the title compound (0.081 g, 77%) as a solid.
LRMS (m/z): 473 (M+1)+.

b) Tert-butyl (3R)-3-{[5-fluoro-6-(2-hydroxyethoxy)-2-pyrazolo[1,5-a]pyridin-3-ylpyrimidin-4-yl]amino}piperidine-1-carboxylate Obtained as a solid dihydrochloride salt (100%) from tert-butyl (3R)-3-{[5-fluoro-6-(2-hydroxyethoxy)-2-pyrazolo[1,5-a]pyridin-3-ylpyrimidin-4-yl]amino}piperidine-1-carboxylate (Example 40a) following the experimental procedure as described in Example 14b.
LRMS (m/z): 373 (M+1)+.

c) 2-((3R)-3-{[5-Fluoro-6-(2-hydroxyethoxy)-2-pyrazolo[1,5-a]pyridin-3-ylpyrimidin-4-yl]amino}piperidin-1-yl)-2-oxoethanol Obtained as a solid (46%) from tert-butyl (3R)-3-{[5-fluoro-6-(2-hydroxyethoxy)-2-pyrazolo[1,5-a]pyridin-3-ylpyrimidin-4-yl]amino}piperidine-1-carboxylate (Example 40b) following the experimental procedure described in Preparation 7 followed by purification by flash chromatography (gradient from dichloromethane to dichloromethane/methanol 95:5).
LRMS (m/z): 431 (M+1)+.
$^1$H-NMR δ (300 MHz, CDCl$_3$): 1.67-1.81 (m, 1H), 1.82-1.99 (m, 1H), 2.09-2.29 (m, 1H), 2.97-3.26 (m, 2H), 3.33-3.58 (m, 2H), 3.66-3.81 (m, 1H), 3.92-4.10 (m, 3H), 4.13-4.35 (m, 3H), 4.61-4.87 (m, 4H), 6.83-6.95 (m, 1H), 7.30-7.38 (m, 1H), 8.41 (dd, 1H), 8.51 (d, 1H), 8.59 (d, 1H).

Example 41

3-[(5-Fluoro-6-{[(3R)-1-glycoloylpiperidin-3-yl]amino}-2-pyrazolo[1,5-a]pyridin-3-ylpyrimidin-4-yl)oxy]propan-1-ol a) Tert-butyl(3R)-3-{[5-fluoro-6-(3-hydroxypropoxy)-2-pyrazolo[1,5-a]pyridin-3-ylpyrimidin-4-yl]amino}piperidine-1-carboxylate Obtained as an orange oil (78%) from tert-butyl (3R)-3-[(6-chloro-5-fluoro-2-pyrazolo[1,5-a]pyridin-3-ylpyrimidin-4-yl)amino]piperidine-1-carboxylate (Preparation 5) and propane-1,3-diol following the experimental procedure as described in Example 5.
LRMS (m/z): 487 (M+1)+.

b) 3-({5-Fluoro-6-[(3R)-piperidin-3-ylamino]-2-pyrazolo[1,5-a]pyridin-3-ylpyrimidin-4-yl}oxy)propan-1-ol Obtained as a yellow solid dihydrochloride salt (97%) from tert-butyl (3R)-3-{[5-fluoro-6-(3-hydroxypropoxy)-2-pyrazolo[1,5-a]pyridin-3-ylpyrimidin-4-yl]amino}piperidine-1-carboxylate (Example 41a) following the experimental procedure as described in Example 14b.
LRMS (m/z): 387 (M+1)+.

c) 3-[(5-Fluoro-6-{[(3R)-1-glycoloylpiperidin-3-yl]amino}-2-pyrazolo[1,5-a]pyridin-3-ylpyrimidin-4-yl)oxy]propan-1-ol Obtained as a white solid (52%) from 3-({5-fluoro-6-[(3R)-piperidin-3-ylamino]-2-pyrazolo[1,5-a]pyridin-3- ylpyrimidin-4-yl}oxy)propan-1-ol (Example 41b) following the experimental procedure as described in Preparation 7 followed by purification by flash chromatography (gradient from dichloromethane to dichloromethane/methanol 95:5).

LRMS (m/z): 445 (M+1)$^+$.

$^1$H-NMR δ (300 MHz, CDCl$_3$): 1.64-1.79 (m, 2H), 1.78-1.94 (m, 1H), 1.95-2.59 (m, 3H), 2.87-3.26 (m, 2H), 3.29-3.57 (m, 2H), 3.59-3.89 (m, 2H), 3.88-4.06 (m, 1H), 4.08-4.32 (m, 2H), 4.54-4.87 (m, 3H), 6.73-6.95 (m, 1H), 7.27-7.40 (m, 1H), 8.22-8.73 (m, 4H).

Example 42

2-{(3R)-3-[(5-Fluoro-6-methoxy-2-pyrazolo[1,5-a]pyridin-3-ylpyrimidin-4-yl)amino]piperidin-1-yl}-2-oxoethanol a) Tert-butyl(3R)-3-[(5-fluoro-6-methoxy-2-pyrazolo[1,5-a]pyridin-3-ylpyrimidin-4-yl)amino]piperidine-1-carboxylate Metal sodium (0.039 g, 1.69 mmol) was added to methanol (5 mL) and the mixture was stirred at room temperature until metal sodium was consumed. Tert-butyl (3R)-3-[(6-chloro-5-fluoro-2-pyrazolo[1,5-a]pyridin-3-ylpyrimidin-4-yl)amino]piperidine-1-carboxylate (Preparation 5, 0.300 g, 0.67 mmol) was added, the reaction mixture was stirred overnight at reflux under nitrogen atmosphere, then cooled to room temperature, the solvent was removed under reduced pressure and the residue was partitioned between water and ethyl acetate. The organic layer was separated and washed with brine, dried and concentrated in vacuo to yield 0.297 g (100% yield) of the title compound, which was used without further purification in the next synthetic step.

LRMS (m/z): 443 (M+1)$^+$.

b) 5-Fluoro-6-methoxy-N-[(3R)-piperidin-3-yl]-2-pyrazolo[1,5-a]pyridin-3-ylpyrimidin-4-amine Obtained as a pale white solid (100%) from tert-butyl (3R)-3-[(5-fluoro-6-methoxy-2-pyrazolo[1,5-a]pyridin-3-ylpyrimidin-4-yl)amino]piperidine-1-carboxylate (Example 42a) following the experimental procedure as described in Example 20b.

LRMS (m/z): 343 (M+1)$^+$.

c) 2-{(3R)-3-[(5-Fluoro-6-methoxy-2-pyrazolo[1,5-a]pyridin-3-ylpyrimidin-4-yl)amino]piperidin-1-yl}-2-oxoethanol Obtained as a white solid (80%) from 5-fluoro-6-methoxy-N-[(3R)-piperidin-3-yl]-2-pyrazolo[1,5-a]pyridin-3-ylpyrimidin-4-amine (Example 42b) following the experimental procedure as described in Preparation 7. The crude was purified by flash chromatography (gradient from dichloromethane to dichloromethane/methanol 93:7).

LRMS (m/z): 401 (M+1)$^+$.

$^1$H-NMR δ (400 MHz, CDCl$_3$): 1.64-2.28 (m, 4H), 2.93-3.79 (m, 5H), 3.90-4.31 (m, 5H), 4.59-4.79 (m, 1H), 6.80-6.93 (m, 1H), 7.27-7.36 (m, 1H), 8.33-8.74 (m, 3H).

Example 43

5-Fluoro-6-{[(3R)-1-glycoloylpiperidin-3-yl]amino}-2-pyrazolo[1,5-a]pyridin-3-ylpyrimidin-4-ol a) 5-Fluoro-6-[(3R)-piperidin-3-ylamino]-2-pyrazolo[1,5-a]pyridin-3-ylpyrimidin-4-ol A suspension of 2-{(3R)-3-[(5-fluoro-6-methoxy-2-pyrazolo[1,5-a]pyridin-3-ylpyrimidin-4-yl)amino]piperidin-1-yl}-2-oxoethanol (Example 42c, 0.086 g, 0.21 mmol) in a 4M solution of hydrochloric acid in dioxane (6 mL) was heated at 80° C. in a sealed tube overnight. Then the mixture was allowed to cool to room temperature and the volatiles were removed under reduced pressure to give 0.078 g (100% yield) of the title compound as its hydrochloric salt.

LRMS (m/z): 329 (M+1)$^+$.

b) 5-Fluoro-6-{[(3R)-1-glycoloylpiperidin-3-yl]amino}-2-pyrazolo[1,5-a]pyridin-3-ylpyrimidin-4-ol Obtained as a white solid (100%) from 5-fluoro-6-[(3R)-piperidin-3-ylamino]-2-pyrazolo[1,5-a]pyridin-3-ylpyrimidin-4-ol (Example 43a) following the experimental procedure as described in Preparation 7. The crude was purified by reverse phase chromatography (C-18 silica from Waters®, water/1:1 acetonitrile-methanol as eluents [0.1% v/v ammonium formate buffered] 0% to 100%).

LRMS (m/z): 387 (M+1)$^+$.

Example 44

Benzyl[(5-fluoro-6-{[(3R)-1-glycoloylpiperidin-3-yl]amino}-2-pyrazolo[1,5-a]pyridin-3-ylpyrimidin-4-yl)oxy]acetate To a solution of 5-fluoro-6-{[(3R)-1-glycoloylpiperidin-3-yl]amino}-2-pyrazolo[1,5-a]pyridin-3-ylpyrimidin-4-ol (Example 43b, 0.062 g, 0.16 mmol) in N,N-dimethylformamide (5 mL) was added silver (I) carbonate (0.530 g, 1.92 mmol) and benzyl 2-bromoacetate (0.220 g, 0.96 mmol) and the mixture was stirred at room temperature for 24 hours. Then it was diluted with water and the resulting suspension was extracted with ethyl acetate. The organic layer was washed with water and brine, dried over magnesium sulfate, filtered and the solvents were evaporated in vacuo. The crude product was purified first by flash chromatography (gradient from dichloromethane to dichloromethane/methanol 90:10) and then by reverse phase chromatography (C-18 silica from Waters®, water/1:1 acetonitrile-methanol as eluents [0.1% v/v ammonium formate buffered] 0% to 100%) to give 0.045 g (53% yield) of the title compound as a white solid.

LRMS (m/z): 535 (M+1)$^+$.

$^1$H-NMR δ (400 MHz, CDCl$_3$): 1.67-1.81 (m, 2H), 1.82-1.97 (m, 1H), 2.12-2.27 (m, 1H), 2.95-4.31 (m, 8H), 4.68-4.88 (m, 2H), 5.05 (s, 2H), 5.22 (s, 2H), 6.76-6.88 (m, 1H), 7.11-7.36 (m, 5H), 8.19-8.37 (m, 1H), 8.42-8.59 (m, 2H).

Example 45

2-{(3R)-3-[(6-Ethoxy-5-fluoro-2-pyrazolo[1,5-a]pyridin-3-ylpyrimidin-4-yl)amino]piperidin-1-yl}-2-oxoethanol a) Tert-butyl(3R)-3-[(6-ethoxy-5-fluoro-2-pyrazolo[1,5-a]pyridin-3-ylpyrimidin-4-yl)amino]piperidine-1-carboxylate Obtained as an oil (63%) from tert-butyl (3R)-3-[(6-chloro-5-fluoro-2-pyrazolo[1,5-a]pyridin-3-ylpyrimidin-4-yl)amino]piperidine-1-carboxylate (Preparation 5) and ethanol following the experimental procedure as described in Example 15a.

LRMS (m/z): 457 (M+1)$^+$.

b) 6-Ethoxy-5-fluoro-N-[(3R)-piperidin-3-yl]-2-pyrazolo[1,5-a]pyridin-3-ylpyrimidin-4-amine Obtained as a solid dihydrochloride salt (100%) from tert-butyl (3R)-3-[(6-ethoxy-5-fluoro-2-pyrazolo[1,5-a]pyridin-3-ylpyrimidin-4-yl)amino]piperidine-1-carboxylate (Example 45a) following the experimental procedure as described in Example 14b.
LRMS (m/z): 357 (M+1)$^+$.

c) 2-{(3R)-3-[(6-Ethoxy-5-fluoro-2-pyrazolo[1,5-a]pyridin-3-ylpyrimidin-4-yl)amino]piperidin-1-yl}-2-oxoethanol Obtained as a white solid (42%) from 6-ethoxy-5-fluoro-N-[(3R)-piperidin-3-yl]-2-pyrazolo[1,5-a]pyridin-3-ylpyrimidin-4-amine (Example 45b) following the experimental procedure described in Preparation 7 followed by purification by flash chromatography (gradient from dichloromethane to dichloromethane/methanol 95:5).
LRMS (m/z): 415 (M+1)$^+$.
$^1$H-NMR δ (300 MHz, CDCl$_3$): 1.43-1.56 (m, 3H), 1.75 (br. s., 2H), 1.90 (br. s., 1H), 2.21 (br. s., 1H), 2.91-3.28 (m, 2H), 3.31-3.64 (m, 2H), 3.73 (d, 1H), 4.02 (d, 1H), 4.15-4.36 (m, 2H), 4.50-4.86 (m, 3H), 6.89 (q, 1H), 7.33 (br. s., 1H), 8.34-8.61 (m, 3H).

Example 46

Ethyl 5-fluoro-6-{[(3R)-1-glycoloylpiperidin-3-yl]amino}-2-pyrazolo[1,5-a]pyridin-3-ylpyrimidine-4-carboxylate a) Tert-butyl(3R)-3-[(6-cyano-5-fluoro-2-pyrazolo[1,5-a]pyridin-3-ylpyrimidin-4-yl)amino]piperidine-1-carboxylate A solution of tert-butyl (3R)-3-[(6-chloro-5-fluoro-2-pyrazolo[1,5-a]pyridin-3-ylpyrimidin-4-yl)amino]piperidine-1-carboxylate (Preparation 5, 0.892 g, 2.00 mmol), tributylstannanecarbonitrile (1.26 g, 3.99 mmol), tetrakis(triphenylphosphine)palladium (0) (0.923 g, 0.80 mmol) and bis(tri-tert-butylphosphine)palladium (0) (0.408 g, 0.80 mmol) in dioxane (20 mL) was heated in a sealed tube under nitrogen atmosphere overnight. Then the reaction mixture was allowed to cool to room temperature, diluted with dichloromethane and filtered through Celite®. The filtered solution was washed with water and brine, dried over magnesium sulfate, filtered and the solvents were removed under reduced pressure. The crude product was purified by flash chromatography (hexanes/ethyl acetate from 0% to 100%) to yield 1.04 g of a semisolid that contained mostly the title compound.
LRMS (m/z): 438 (M+1)$^+$.

b) 6-{[(3R)-1-(Tert-butoxycarbonyl)piperidin-3-yl]amino}-5-fluoro-2-pyrazolo[1,5-a]pyridin-3-ylpyrimidine-4-carboxylic acid The product obtained in Example 46a was dissolved in 2-propanol (4 mL) an 2M aqueous solution of sodium hydroxide (15 mL) and heated for 35 minutes at 80° C. under microwave irradiation. Then the reaction mixture was partitioned between dichloromethane and water and the layers were separated. The aqueous layer was acidified with hydrochloric acid 2M and extracted with dichloromethane/methanol (98:2) several times. The combined organic solution was dried over magnesium sulfate, filtered and the solvents were removed. The crude product was purified by reverse phase chromatography (C-18 silica from Waters®, water/1:1 acetonitrile-methanol as eluents [0.1% v/v ammonia in both eluent systems] 0% to 100%) to give 0.193 g (21% yield in two steps) of the title compound as a white solid.
LRMS (m/z): 456 (M+1)$^+$.

c) Ethyl-5-fluoro-6-[(3R)-piperidin-3-ylamino]-2-pyrazolo[1,5-a]pyridin-3-ylpyrimidine-4-carboxylate A solution of 6-{[(3R)-1-(tert-butoxycarbonyl)piperidin-3-yl]amino}-5-fluoro-2-pyrazolo[1,5-a]pyridin-3-ylpyrimidine-4-carboxylic acid (Example 46b, 0.299 g, 0.66 mmol) and concentrated sulfuric acid (0.174 mL, 3.3 mmol) in ethanol (8 mL) was heated to 100° C. overnight. Then the volatiles were removed under reduced pressure and the residue was partitioned between water and dichloromethane. The aqueous layer was separated and the pH was adjusted to 8 by slow addition of a diluted solution of sodium hydroxide and it was extracted with dichloromethane. The organic solution was washed with brine, dried over magnesium sulfate, filtered and the solvent was removed under reduced pressure to give 0.101 g of the title compound (30% yield).
LRMS (m/z): 385 (M+1)$^+$.

d) Ethyl-5-fluoro-6-{[(3R)-1-glycoloylpiperidin-3-yl]amino}-2-pyrazolo[1,5-a]pyridin-3-ylpyrimidine-4-carboxylate Obtained as a light yellow solid (24%) from 5-fluoro-6-[(3R)-piperidin-3-ylamino]-2-pyrazolo[1,5-a]pyridin-3-ylpyrimidin-4-ol (Example 46c) following the experimental procedure as described in Preparation 7. The crude was purified first by flash chromatography (dichloromethane/methanol from 0% to 15%) and then by reverse phase chromatography (C-18 silica from Waters®, water/1:1 acetonitrile-methanol as eluents [0.1% v/v ammonium formate buffered] 0% to 100%).
LRMS (m/z): 443 (M+1)$^+$.
$^1$H-NMR δ (400 MHz, CDCl$_3$): 1.37-1.53 (m, 3H), 1.62-1.96 (m, 4H), 3.07-3.83 (m, 3H), 3.97-4.10 (m, 1H), 4.17-4.73 (m, 5H), 5.20 (d, J=7.6 Hz, 1H), 6.82-6.95 (m, 1H), 7.29-7.42 (m, 1H), 8.47-8.76 (m, 3H).

Example 47

5-Fluoro-6-{[(3R)-1-glycoloylpiperidin-3-yl]amino}-2-pyrazolo[1,5-a]pyridin-3-ylpyrimidine-4-carbonitrile a) 5-Fluoro-6-[(3R)-piperidin-3-ylamino]-2-pyrazolo[1,5-a]pyridin-3-ylpyrimidine-4-carbonitrile A solution of tert-butyl (3R)-3-[(6-cyano-5-fluoro-2-pyrazolo[1,5-a]pyridin-3-ylpyrimidin-4-yl)amino]piperidine-1-carboxylate (Example 46a, 0.150 g, 0.34 mmol) and concentrated sulfuric acid (0.091 mL, 1.7 mmol) in ethanol (6 mL) was heated to 100° C. overnight. Then the volatiles were removed under reduced pressure and the residue was partitioned between water and dichloromethane. The aqueous layer was separated and the pH was adjusted to 8 by slow addition of aqueous solution of sodium hydrogencarbonate and it was extracted with dichloromethane. The organic solution was washed with brine, dried over magnesium sulfate, filtered and the solvent was removed under reduced pressure to give 0.083 g of the title compound as a deep yellow solid (63% yield).

LRMS (m/z): 338 (M+1)$^+$.

b) 5-Fluoro-6-{[(3R)-1-glycoloylpiperidin-3-yl]amino}-2-pyrazolo[1,5-a]pyridin-3-ylpyrimidine-4-carbonitrile Obtained as a yellow solid (38%) from 5-fluoro-6-[(3R)-piperidin-3-ylamino]-2-pyrazolo[1,5-a]pyridin-3-ylpyrimidine-4-carbonitrile (Example 47a) following the experimental procedure as described in Preparation 7. The crude was purified by reverse phase chromatography (C-18 silica from Waters®, water/1:1 acetonitrile-methanol as eluents [0.1% v/v ammonium formate buffered] 0% to 100%).

LRMS (m/z): 396 (M+1)$^+$.

$^1$H-NMR δ (400 MHz, DMSO-d$_6$): 1.44-1.90 (m, 3H), 1.93-2.12 (m, 1H), 2.56-3.09 (m, 3H), 3.58-3.87 (m, 1H), 3.91-4.29 (m, 3H), 4.50-4.75 (m, 1H), 7.07 (s, 1H), 7.40-7.58 (m, 1H), 8.19-8.40 (m, 2H), 8.58-8.69 (m, 1H), 8.79 (s, 1H).

Example 48

5-Fluoro-6-{[(3R)-1-glycoloylpiperidin-3-yl]amino}-2-pyrazolo[1,5-a]pyridin-3-ylpyrimidine-4-carboxamide To a solution of ethyl 5-fluoro-6-{[(3R)-1-glycoloylpiperidin-3-yl]amino}-2-pyrazolo[1,5-a]pyridin-3-ylpyrimidine-4-carboxylate (Example 46d, 23 mg, 0.052 mmol) in a mixture of tetrahydrofurane (2 mL) and water (0.5 mL) were added a few drops of concentrated ammonia. The resulting solution was stirred overnight at room temperature and then partitioned between water and dichloromethane. The organic layer was separated and washed with water and brine, dried over magnesium sulfate, filtered and the solvent was removed to give 0.008 g (37% yield) of the title compound as a pale solid.

LRMS (m/z): 414 (M+1)$^+$.

Example 49

2-((3R)-3-{[5-Fluoro-2-pyrazolo[1,5-a]pyridin-3-yl-6-(2,2,2-trifluoroethoxy)pyrimidin-4-yl]amino}piperidin-1-yl)-2-oxoethanol a) Tert-butyl(3R)-3-{[5-fluoro-2-pyrazolo[1,5-a]pyridin-3-yl-6-(2,2,2-trifluoroethoxy)pyrimidin-4-yl]amino}piperidine-1-carboxylate Obtained as an white solid (92%) from tert-butyl (3R)-3-[(6-chloro-5-fluoro-2-pyrazolo[1,5-a]pyridin-3-ylpyrimidin-4-yl)amino]piperidine-1-carboxylate (Preparation 5) and 2,2,2-trifluoroethanol following the experimental procedure described in Example 5.

LRMS (m/z): 511 (M+1)$^+$.

b) 5-Fluoro-N-[(3R)-piperidin-3-yl]-2-pyrazolo[1,5-a]pyridin-3-yl-6-(2,2,2-trifluoroethoxy)pyrimidin-4-amine Obtained as a solid dihydrochloride salt (100%) from tert-butyl (3R)-3-{[5-fluoro-2-pyrazolo[1,5-a]pyridin-3-yl-6-(2,2,2-trifluoroethoxy)pyrimidin-4-yl]amino}piperidine-1-carboxylate (Example 49a) following the experimental procedure described in Example 14b.

LRMS (m/z): 411 (M+1)$^+$.

c) 2-((3R)-3-{[5-Fluoro-2-pyrazolo[1,5-a]pyridin-3-yl-6-(2,2,2-trifluoroethoxy)pyrimidin-4-yl]amino}piperidin-1-yl)-2-oxoethanol Obtained as a white solid (32%) from 5-fluoro-N-[(3R)-piperidin-3-yl]-2-pyrazolo[1,5-a]pyridin-3-yl-6-(2,2,2-trifluoroethoxy)pyrimidin-4-amine (Example 49b) following the experimental procedure described in Preparation 7 followed by purification by flash chromatography (gradient from dichloromethane to dichloromethane/methanol 95:5).

LRMS (m/z): 469 (M+1)$^+$.

$^1$H-NMR δ (300 MHz, CDCl$_3$): 1.69-1.85 (m, 2H), 1.86-2.04 (m, 1H), 2.12-2.38 (m, 1H), 2.92-3.26 (m, 2H), 3.28-3.65 (m, 2H), 3.68-3.83 (m, 1H), 3.95-4.15 (m, 1H), 4.15-4.36 (m, 2H), 4.69-5.08 (m, 3H), 6.85-7.00 (m, 1H), 7.32-7.45 (m, 1H), 8.33 (d, 1H), 8.43 (d, 1H), 8.49-8.61 (m, 1H).

Example 50

2-((3R)-3-{[6-(2,2-Difluoroethoxy)-5-fluoro-2-pyrazolo[1,5-a]pyridin-3-ylpyrimidin-4-yl]amino}piperidin-1-yl)-2-oxoethanol a) Tert-butyl-(3R)-3-{[6-(2,2-difluoroethoxy)-5-fluoro-2-pyrazolo[1,5-a]pyridin-3-ylpyrimidin-4-yl]amino}piperidine-1-carboxylate Obtained as a beige solid (99%) from tert-butyl (3R)-3-[(6-chloro-5-fluoro-2-pyrazolo[1,5-a]pyridin-3-ylpyrimidin-4-yl)amino]piperidine-1-carboxylate (Preparation 5) and 2,2-difluoroethanol following the experimental procedure described in Example 5.

LRMS (m/z): 493 (M+1)$^+$.

b) 6-(2,2-Difluoroethoxy)-5-fluoro-N-[(3R)-piperidin-3-yl]-2-pyrazolo[1,5-a]pyridin-3-ylpyrimidin-4-amine Obtained as a solid dihydrochloride salt (100%) from tert-butyl (3R)-3-{[6-(2,2-difluoroethoxy)-5-fluoro-2-pyrazolo[1,5-a]pyridin-3-ylpyrimidin-4-yl]amino}piperidine-1-carboxylate (Example 50a) following the experimental procedure as described in Example 14b.

LRMS (m/z): 393 (M+1)$^+$.

c) 2-((3R)-3-{[6-(2,2-Difluoroethoxy)-5-fluoro-2-pyrazolo[1,5-a]pyridin-3-ylpyrimidin-4-yl]amino}piperidin-1-yl)-2-oxoethanol Obtained as a white solid (40%) from 6-(2,2-difluoroethoxy)-5-fluoro-N-[(3R)-piperidin-3-yl]-2-pyrazolo[1,5-a]pyridin-3-ylpyrimidin-4-amine (Example 50b) following the experimental procedure described in Preparation 7 followed by purification by flash chromatography (gradient from dichloromethane to dichloromethane/methanol 95:5).

LRMS (m/z): 451 (M+1)$^+$.

1H-NMR δ (300 MHz, CDCl$_3$): 1.64-1.85 (m, 2H), 1.84-2.05 (m, 1H), 2.12-2.35 (m, 1H), 2.94-3.29 (m, 2H), 3.29-3.61 (m, 2H), 3.66-3.79 (m, 1H), 3.93-4.10 (m, 1H), 4.16-

4.37 (m, 2H), 4.58-4.96 (m, 3H), 6.24 (t, 1H), 6.84-7.00 (m, 1H), 7.32-7.45 (m, 1H), 8.35 (d, 1H), 8.44 (d, 1H), 8.50-8.61 (m, 1H).

Example 51

2-{(3R)-3-[(5-Fluoro-6-isopropoxy-2-pyrazolo[1,5-a]pyridin-3-ylpyrimidin-4-yl)amino]piperidin-1-yl}-2-oxoethanol a) Tert-butyl-(3R)-3-[(5-fluoro-6-isopropoxy-2-pyrazolo[1,5-a]pyridin-3-ylpyrimidin-4-yl)amino]piperidine-1-carboxylate Obtained as an orange oil (92%) from tert-butyl (3R)-3-[(6-chloro-5-fluoro-2-pyrazolo[1,5-a]pyridin-3-ylpyrimidin-4-yl)amino]piperidine-1-carboxylate (Preparation 5) and isopropanol following the experimental procedure described in Example 15a.
LRMS (m/z): 471 (M+1)$^+$.

b) 5-Fluoro-6-isopropoxy-N-[(3R)-piperidin-3-yl]-2-pyrazolo[1,5-a]pyridin-3-ylpyrimidin-4-amine Obtained as a solid dihydrochloride salt (86%) from tert-butyl (3R)-3-[(5-fluoro-6-isopropoxy-2-pyrazolo[1,5-a]pyridin-3-ylpyrimidin-4-yl)amino]piperidine-1-carboxylate (Example 51a) following the experimental procedure described in Example 14b.
LRMS (m/z): 371 (M+1)$^+$.

c) 2-{(3R)-3-[(5-Fluoro-6-isopropoxy-2-pyrazolo[1,5-a]pyridin-3-ylpyrimidin-4-yl)amino]piperidin-1-yl}-2-oxoethanol Obtained as a light yellow solid (29%) from 5-fluoro-6-isopropoxy-N-[(3R)-piperidin-3-yl]-2-pyrazolo[1,5-a]pyridin-3-ylpyrimidin-4-amine (Example 51b) following the experimental procedure described in Preparation 7 followed by purification by flash chromatography (gradient from dichloromethane to methanol 95:5).
LRMS (m/z): 429 (M+1)$^+$.
$^1$H-NMR δ (300 MHz, CDCl$_3$): 1.47 (d, 6H), 1.65-1.80 (m, 2H), 1.82-1.94 (m, 1H), 2.09-2.28 (m, 1H), 2.87-3.25 (m, 2H), 3.25-3.57 (m, 2H), 3.67-3.79 (m, 1H), 3.93-4.08 (m, 1H), 4.11-4.30 (m, 2H), 4.61-4.85 (m, 1H), 5.42-5.64 (m, 1H), 6.74-6.95 (m, 1H), 7.28-7.33 (m, 1H), 8.28-8.58 (m, 3H).

Example 52

2-{(3R)-3-[(5-Fluoro-6-morpholin-4-yl-2-pyrazolo[1,5-a]pyridin-3-ylpyrimidin-4-yl)oxy]piperidin-1-yl}-2-oxoethanol a) 3-(4-Chloro-5-fluoro-6-morpholin-4-ylpyrimidin-2-yl)pyrazolo[1,5-a]pyridine To a solution of 3-(4,6-dichloro-5-fluoropyrimidin-2-yl)pyrazolo[1,5-a]pyridine (Preparation 1d, 0.500 g, 1.77 mmol) in a mixture of ethanol (20 mL) and tetrahydrofurane (10 mL) were added morpholine (0.183 mL, 2.11 mmol) and triethylamine (0.295 mL, 2.12 mmol). The resulting mixture was stirred for 3 hours and then the volatiles were removed under reduced pressure. The residue was partitioned between water and dichloromethane, the organic layer was separated and washed with water, diluted hydrochloric acid and brine, dried over magnesium sulfate, filtered and the solvent was removed to give 0.575 g (98% yield) of the title compound as a pale solid.
LRMS (m/z): 334 (M+1)$^+$.

b) Tert-butyl-(3R)-3-[(5-fluoro-6-morpholin-4-yl-2-pyrazolo[1,5-a]pyridin-3-ylpyrimidin-4-yl)oxy]piperidine-1-carboxylate To a solution of tert-butyl (3R)-3-hydroxypiperidine-1-carboxylate (0.975 g, 4.84 mmol) in dioxane (10 mL) was added potassium tert-butoxide (0.370 g, 3.30 mmol). It was stirred at room temperature for 15 minutes and then 3-(4-chloro-5-fluoro-6-morpholin-4-ylpyrimidin-2-yl)pyrazolo[1,5-a]pyridine (Example 52a, 0.275 g, 0.82 mmol) were added. The resulting mixture was heated to 90° C. overnight and then it was allowed to cool to room temperature and diluted with ethyl acetate, washed with water (×3) and brine, dried over magnesium sulfate, filtered and the solvents were removed. The crude product was purified first by flash chromatography (dichloromethane to dichloromethane/methanol 94:6) and then by reverse phase chromatography (C-18 silica from Waters®, water/1:1 acetonitrile-methanol as eluents [0.1% v/v ammonium formate buffered] 0% to 100%) to yield the title compound (0.362 g, 88% yield) as a white solid.
LRMS (m/z): 499 (M+1)$^+$.

c) 3-{5-Fluoro-4-morpholin-4-yl-6-[(3R)-piperidin-3-yloxy]pyrimidin-2-yl}pyrazolo[1,5-a]pyridine Obtained as a pale white solid (95%) from tert-butyl (3R)-3-[(5-fluoro-6-morpholin-4-yl-2-pyrazolo[1,5-a]pyridin-3-ylpyrimidin-4-yl)oxy]piperidine-1-carboxylate (Example 52b) following the experimental procedure as described in Example 20b.
LRMS (m/z): 399 (M+1)$^+$.

d) 2-{(3R)-3-[(5-Fluoro-6-morpholin-4-yl-2-pyrazolo[1,5-a]pyridin-3-ylpyrimidin-4-yl)oxy]piperidin-1-yl}-2-oxoethanol Obtained as a white solid (74%) from 3-{5-fluoro-4-morpholin-4-yl-6-[(3R)-piperidin-3-yloxy]pyrimidin-2-yl}pyrazolo[1,5-a]pyridine (Example 52c) following the experimental procedure as described in Preparation 7. The crude was purified by reverse phase chromatography (C-18 silica from Waters®, water/1:1 acetonitrile-methanol as eluents [0.1% v/v ammonium formate buffered] 0% to 100%).
LRMS (m/z): 457 (M+1)$^+$.
$^1$H-NMR δ (400 MHz, CDCl$_3$): 1.70-2.27 (m, 4H), 3.18-3.76 (m, 4H), 3.76-3.92 (m, 7H), 3.94-4.33 (m, 2H), 5.20-5.35 (m, 1H), 6.81-6.93 (m, 1H), 7.27-7.36 (m, 1H), 8.26-8.40 (m, 1H), 8.47-8.63 (m, 2H).

Example 53

3-{(3R)-3-[(5-fluoro-6-morpholin-4-yl-2-pyrazolo[1,5-a]pyridin-3-ylpyrimidin-4-yl)oxy]piperidin-1-yl}-3-oxopropanenitrile Obtained as a white solid (80%) from 3-{5-fluoro-4-morpholin-4-yl-6-[(3R)-piperidin-3-yloxy]pyrimidin-2-yl}pyrazolo[1,5-a]pyridine (Example 52c, 0.135 mg, 0.34 mmol) following the experimental procedure as described in Preparation 6b. The crude was purified by reverse phase chromatography (C-18 silica from Waters®, water/1:1 acetonitrile-methanol as eluents [0.1% v/v ammonium formate buffered] 0% to 100%).

LRMS (m/z): 466 (M+1)$^+$.

$^1$H-NMR δ (400 MHz, CDCl$_3$): 1.63-2.33 (m, 4H), 3.12-3.29 (m, 1H), 3.41-3.71 (m, 4H), 3.82 (m, 8H), 4.02-4.25 (m, 1H), 5.25-5.40 (m, 1H), 6.82-6.94 (m, 1H), 7.29-7.38 (m, 1H), 8.27-8.39 (m, 1H), 8.46-8.60 (m, 2H).

Example 54

5-((3R)-3-{[5-fluoro-6-(2-hydroxyethoxy)-2-pyrazolo[1,5-a]pyridin-3-ylpyrimidin-4-yl]amino}piperidin-1-yl)pyrazine-2-carbonitrile A mixture of (R)-2-((5-fluoro-6-(piperidin-3-ylamino)-2-(pyrazolo[1,5-a]pyridin-3-yl)pyrimidin-4-yl)oxy)ethanol dihydrochloride (Example 40b, 0.050 g, 0.13 mmol), 2-chloro-5-cyanopyrazine (0.025 g, 0.18 mmol) and triethylamine (0.056 mL, 0.4 mmol) in N,N-dimethylformamide (1.0 mL) was heated in a microwave at 120° C. for 2 hours. The reaction mixture was cooled to ambient temperature and ethyl acetate (10 mL) was added. The solution was washed with water (10 mL) and brine (20 mL). The organic layer was separated, dried over anhydrous magnesium sulfate, filtered, and concentrated under reduced pressure. The residue was taken up in dichloromethane (5 mL), the suspension was filtered and dried in vacuo to give the title compound (0.012 g, 19%) as a solid.

LRMS (m/z): 476 (M+1)$^+$.

$^1$H-NMR δ (300 MHz, DMSO-d$_6$): 1.50-1.98 (m, 4H), 2.00-2.17 (m, 1H), 3.02 (dd, 2H), 3.68-3.87 (m, 2H), 4.14 (br. s., 1H), 4.42 (d, 1H), 4.50 (d, 2H), 4.75 (br. s., 1H), 4.93 (d, 1H), 6.94-7.10 (m, 1H), 7.30 (dd, 2H), 8.32 (d, 1H), 8.46 (d, 1H), 8.58 (s, 1H), 8.80 (d, 1H).

Example 55

(5-{(3R)-3-[(5-fluoro-6-methoxy-2-pyrazolo[1,5-a]pyridin-3-ylpyrimidin-4-yl)amino]piperidin-1-yl}pyrazin-2-yl)methanol A mixture of (R)-5-fluoro-6-methoxy-N-(piperidin-3-yl)-2-(pyrazolo[1,5-a]pyridin-3-yl)pyrimidin-4-amine dihydrochloride (Example 42b, 0.040 g, 0.12 mmol), (5-chloropyrazin-2-yl)methanol (0.017 g, 0.12 mmol) and diethylisopropylamine (0.061 mL, 0.35 mmol) in N-Methyl-2-pyrrolidone (1.0 mL) was heated in a microwave at 120° C. for 19 hours. The reaction mixture was cooled to ambient temperature and ethyl acetate (10 mL) was added. The solution was washed with water (10 mL) and brine (20 mL). The organic layer was separated, dried over anhydrous magnesium sulfate, filtered, and concentrated under reduced pressure. Purification of the residue by flash chromatography (dichloromethane to 95:5 dichloromethane/ethanol) gave the title compound (0.007 mg, 13%) as a solid.

LRMS (m/z): 446 (M+1)$^+$.

$^1$H-NMR δ (300 MHz, CDCl$_3$): 1.52-2.02 (m, 3H), 2.12-2.27 (m, 1H), 3.16-3.51 (m, 2H), 4.01 (dd, 1H), 4.15 (s, 3H), 4.25-4.40 (m, 1H), 4.45 (dd, 1H), 4.70 (s, 2H), 4.95 (d, 1H), 6.75-6.95 (m, 1H), 7.13-7.26 (m, 1H), 8.12 (s, 1H), 8.21 (s, 1H), 8.39-8.56 (m, 2H), 8.64 (s, 1H).

Example 56

5-{(3R)-3-[(5-fluoro-6-methoxy-2-pyrazolo[1,5-a]pyridin-3-ylpyrimidin-4-yl)amino]piperidin-1-yl}pyrazine-2-carbonitrile A mixture of (R)-5-fluoro-6-methoxy-N-(piperidin-3-yl)-2-(pyrazolo[1,5-a]pyridin-3-yl)pyrimidin-4-amine dihydrochloride (Example 42b, 0.054 g, 0.13 mmol), 2-chloro-5-cyanopyrazine (0.054 g, 0.38 mmol) and potassium carbonate (0.090 g, 0.65 mmol) in N,N-dimethylformamide (1.0 mL) was heated in a microwave at 120° C. for 1 hours. The reaction mixture was cooled to ambient temperature and ethyl acetate (10 mL) was added. The solution was washed with water (10 mL) and brine (20 mL). The organic layer was separated, dried over anhydrous magnesium sulfate, filtered, and concentrated under reduced pressure. The residue was taken up in dichloromethane (5 mL), the suspension was filtered and dried in vacuo to give the title compound (0.012 g, 19%) as a pale yellow solid.

LRMS (m/z): 446 (M+1)$^+$.

$^1$H-NMR δ (300 MHz, DMSO-d6): 1.61-1.96 (m, 4H), 2.02-2.16 (m, 1H), 2.98-3.22 (m, 2H), 4.07 (s, 3H), 4.10-4.24 (m, 1H), 4.42 (d, 1H), 4.74 (br. s., 1H), 7.04 (d, 1H), 7.30 (dd, 2H), 8.37 (d, 1H), 8.47 (d, 1H), 8.60 (s, 1H), 8.81 (d, 1H).

Example 57

2-((3R)-3-{[5-fluoro-6-(2-hydroxyethoxy)-2-pyrazolo[1,5-a]pyridin-3-ylpyrimidin-4-yl]amino}piperidin-1-yl)pyrimidine-5-carbonitrile A mixture of (R)-2-((5-fluoro-6-(piperidin-3-ylamino)-2-(pyrazolo[1,5-a]pyridin-3-yl)pyrimidin-4-yl)oxy)ethanol dihydrochloride (Example 40b, 0.060 g, 0.16 mmol), 2-chloropyrimidine-5-carbonitrile (0.033 g, 0.24 mmol) and triethylamine (0.070 mL, 0.50 mmol) in N,N-dimethylformamide (1.0 mL) was heated in a microwave at 120° C. for 2 hours. The reaction mixture was cooled to ambient temperature and ethyl acetate (10 mL) was added. The solution was washed with water (10 mL) and brine (20 mL). The organic layer was separated, dried over anhydrous magnesium sulfate, filtered, and concentrated under reduced pressure. The residue was taken up in dichloromethane (7 mL), the suspension was filtered and dried in vacuo to give the title compound (0.025 g, 33%) as a solid.

LRMS (m/z): 476 (M+1)$^+$.

1H-NMR δ (300 MHz, DMSO-d$_6$): 1.44-1.96 (m, 4H), 2.00-2.22 (m, 1H), 2.84-3.15 (m, 2H), 3.67-3.85 (m, 2H), 4.06 (d, 1H), 4.50 (d, 2H), 4.68 (d, 1H), 4.93 (d, 1H) 5.07 (dd, 1H), 6.94-7.09 (m, 1H), 7.22-7.38 (m, 2H), 8.33 (d, 1H), 8.63 (s, 1H), 8.80 (d, 2H).

Example 58

2-[(3R)-3-({5-Fluoro-6-[(1S)-2-methoxy-1-methylethoxy]-2-pyrazolo[1,5-a]pyridin-3-ylpyrimidin-4-yl}amino)piperidin-1-yl]-2-oxoethanol a) Tert-butyl (3R)-3-({5-fluoro-6-[(1S)-2-methoxy-1-methylethoxy]-2-pyrazolo[1,5-a]pyridin-3-ylpyrimidin-4-yl}amino)piperidine-1-carboxylate Obtained as an oil (72%) from tert-butyl (3R)-3-[(6-chloro-5-fluoro-2-pyrazolo[1,5-a]pyridin-3-ylpyrimidin-4- yl)amino]piperidine-1-carboxylate (Preparation 5) and (2S)-1-methoxypropan-2-ol following the experimental procedure described in Example 15a.

LRMS (m/z): 501 (M+1)$^+$.

b) 5-Fluoro-6-[(1S)-2-methoxy-1-methylethoxy]-N-[(3R)-piperidin-3-yl]-2-pyrazolo[1,5-a]pyridin-3-ylpyrimidin-4-amine Obtained as a solid dihydrochloride salt (98%) from tert-butyl (3R)-3-({5-fluoro-6-[(1S)-2-methoxy-1-methylethoxy]-2-pyrazolo[1,5-a]pyridin-3-ylpyrimidin-4-yl}amino)piperidine-1-carboxylate (Example 58a) following the experimental procedure described in Example 14b.

LRMS (m/z): 401 (M+1)$^+$.

c) 2-[(3R)-3-({5-Fluoro-6-[(1S)-2-methoxy-1-methylethoxy]-2-pyrazolo[1,5-a]pyridin-3-ylpyrimidin-4-yl}amino)piperidin-1-yl]-2-oxoethanol Obtained as a white solid (24%) from 5-fluoro-6-[(1S)-2-methoxy-1-methylethoxy]-N-[(3R)-piperidin-3-yl]-2-pyrazolo[1,5-a]pyridin-3-ylpyrimidin-4-amine dihydrochloride salt (Example 58b) following the experimental procedure described in Preparation 7 followed by purification by flash chromatography (gradient from dichloromethane to dichloromethane/methanol 95:5).

LRMS (m/z): 459 (M+1)$^+$.

$^1$H NMR (300 MHz, CDCl$_3$): δ 1.24-1.33 (m, 3H), 1.45-1.52 (m, 3H), 1.69-1.81 (m, 2H), 1.90 (s, 1H), 2.15-2.28 (m, 1H), 2.92-3.23 (m, 2H), 3.26-3.40 (m, 1H), 3.46 (s, 3H), 3.52-3.81 (m, 2H), 3.96-4.12 (m, 1H), 4.18-4.31 (m, 1H), 4.65-4.83 (m, 1H), 5.52-5.67 (m, 1H), 6.81-6.98 (m, 1H), 7.30-7.37 (m, 1H), 8.30-8.70 (m, 3H).

Example 59

(2S)-2-[(5-Fluoro-6-{[(3R)-1-glycoloylpiperidin-3-yl]amino}-2-pyrazolo[1,5-a]pyridin-3-ylpyrimidin-4-yl)oxy]propan-1-ol To a 0° C. cooled solution of 2-[(3R)-3-({5-fluoro-6-[(1S)-2-methoxy-1-methylethoxy]-2-pyrazolo[1,5-a]pyridin-3-ylpyrimidin-4-yl}amino)piperidin-1-yl]-2-oxoethanol (Example 58c, 0.053 g, 0.12 mmol) in dichloromethane (1 mL), a 1M solution of boron tribromide in dichloromethane (0.24 mL, 0.24 mmol) was added. The mixture was stirred at 0° C. for 1.5 hours and concentrated to dryness. A mixture of methanol and 7N ammonia in methanol (1:1) (2 mL) was added and the resulting suspension was concentrated to dryness. The crude was purified by preparative HPLC (gradient from water to methanol) to yield the pure title compound (0.021 g, 41%) as a white solid.

LRMS (m/z): 445 (M+1)$^+$.

$^1$H NMR (300 MHz, CDCl$_3$): δ 1.23-1.33 (m, 2H), 1.42-1.51 (m, 3H), 1.70-2.30 (m, 4H), 2.95-3.24 (m, 2H), 3.30-4.12 (m, 4H), 4.23 (d, 1H), 4.77 (m, 1H), 5.48 (m, 1H), 6.89 (m, 1H), 7.27-7.41 (m, 3H), 8.26-8.68 (m, 3H).

Example 60

2-[(3R)-3-({5-Fluoro-6-[(1R)-2-methoxy-1-methylethoxy]-2-pyrazolo[1,5-a]pyridin-3-ylpyrimidin-4-yl}amino)piperidin-1-yl]-2-oxoethanol a) Tert-butyl (3R)-3-({5-fluoro-6-[(1R)-2-methoxy-1-methylethoxy]-2-pyrazolo[1,5-a]pyridin-3-ylpyrimidin-4-yl}amino)piperidine-1-carboxylate Obtained as a colorless oil (72%) from tert-butyl (3R)-3-[(6-chloro-5-fluoro-2-pyrazolo[1,5-a]pyridin-3-ylpyrimidin-4-yl)amino]piperidine-1-carboxylate (Preparation 5) and (2R)-1-methoxypropan-2-ol following the experimental procedure described in Example 15a.

LRMS (m/z): 501 (M+1)$^+$.

b) 5-Fluoro-6-[(1R)-2-methoxy-1-methylethoxy]-N-[(3R)-piperidin-3-yl]-2-pyrazolo[1,5-a]pyridin-3-ylpyrimidin-4-amine Obtained as a yellow oil (100%) from tert-butyl (3R)-3-({5-fluoro-6-[(1R)-2-methoxy-1-methylethoxy]-2-pyrazolo[1,5-a]pyridin-3-ylpyrimidin-4-yl}amino)piperidine-1-carboxylate (Example 60a) following the experimental procedure described in Example 20b.

LRMS (m/z): 401 (M+1)$^+$.

c) 2-[(3R)-3-({5-Fluoro-6-[(1R)-2-methoxy-1-methylethoxy]-2-pyrazolo[1,5-a]pyridin-3-ylpyrimidin-4-yl}amino)piperidin-1-yl]-2-oxoethanol Obtained as a white solid (46%) from 5-fluoro-6-[(1R)-2-methoxy-1-methylethoxy]-N-[(3R)-piperidin-3-yl]-2-pyrazolo[1,5-a]pyridin-3-ylpyrimidin-4-amine (Example 60b) following the experimental procedure described in Preparation 7 followed by purification by reverse phase chromatography (C-18 silica from Waters®, water/methanol as eluents 0% to 100%).

LRMS (m/z): 459 (M+1)$^+$.

$^1$H NMR (400 MHz, CDCl$_3$): δ 1.36-1.50 (m, 3H), 1.71 (m, 2H), 1.82-1.94 (m, 1H), 2.17 (s, 1H), 2.92-3.39 (m, 3H), 3.43 (s, 3H), 3.48-3.61 (m, 2H), 3.67-3.76 (m, 2H), 3.95-4.05 (m, 1H), 4.16-4.25 (m, 2H), 4.66-4.77 (m, 1H), 5.47-5.63 (m, 1H), 6.76-6.91 (m, 1H), 7.26-7.36 (m, 1H), 8.31-8.66 (m, 3H).

Example 61

(2R)-2-[(5-Fluoro-6-{[(3R)-1-glycoloylpiperidin-3-yl]amino}-2-pyrazolo[1,5-a]pyridin-3-ylpyrimidin-4-yl)oxy]propan-1-ol Obtained as a white solid (90%) from 2-[(3R)-3-({5-fluoro-6-[(1R)-2-methoxy-1-methylethoxy]-2-pyrazolo[1,5-a]pyridin-3-ylpyrimidin-4-yl}amino)piperid in-1-yl]-2-oxoethanol (Example 60c) following the experimental procedure described in Example 59.

LRMS (m/z): 445 (M+1)$^+$.

$^1$H NMR (400 MHz, CDCl$_3$): δ 1.45 (dd, 3H), 1.68-1.79 (m, 2H), 1.85-1.92 (m, 1H), 2.16-2.24 (m, 1H), 2.83-3.22 (m, 3H), 3.35-3.56 (m, 2H), 3.66-3.76 (m, 1H), 3.83-3.89 (m, 2H), 3.99 (dd, 4.2 Hz, 1H), 4.14-4.27 (m, 2H), 4.66-4.81 (m, 1H), 5.41-5.52 (m, 1H), 6.82-6.92 (m, 1H), 7.27-7.37 (m, 1H), 8.29-8.63 (m, 3H).

Example 62

2-{(3R)-3-[(5-Fluoro-2-pyrazolo[1,5-a]pyridin-3-yl-6-pyridin-3-ylpyrimidin-4-yl)amino]piperidin-1-yl}-2-oxoethanol Obtained as a yellow solid (18%) from 3-{(3R)-3-[(6-chloro-5-fluoro-2-pyrazolo[1,5-a]pyridin-3-ylpyrimidin-4-yl)amino]piperidin-1-yl}-3-oxopropanenitrile (Preparation 7b) following the experimental procedure described in Example 17 followed by purification by flash chromatography (gradient from dichloromethane to dichloromethane/methanol 95:5).

LRMS (m/z): 448 (M+1)+.
1H NMR (400 MHz, CDCl$_3$): δ 1.69-2.01 (m, 3H), 2.21 (d, 1H), 3.13-3.51 (m, 4H), 3.77 (d, 1H), 3.92-4.08 (m, 1H), 4.19-4.40 (m, 3H), 4.66 (d, 1H), 5.13 (s, 1H), 6.80-6.95 (m, 1H), 7.29-7.41 (m, 1H), 7.41-7.56 (m, 1H), 8.38-8.82 (m, 5H), 9.37 (s, 1H).

Example 63

2-{(3R)-3-[(5-Fluoro-6-methoxy-2-pyrazolo[1,5-a]pyridin-3-ylpyrimidin-4-yl)oxy]piperidin-1-yl}-2-oxoethanol a) Tert-butyl (3R)-3-[(5-fluoro-6-methoxy-2-pyrazolo[1,5-a]pyridin-3-ylpyrimidin-4-yl)oxy]piperidine-1-carboxylate Metal sodium (0.031 g, 1.34 mmol) was added to methanol (8 mL) and the mixture was stirred at room temperature until metal sodium was consumed. Tert-butyl (3R)-3-[(6-chloro-5-fluoro-2-pyrazolo[1,5-a]pyridin-3-ylpyrimidin-4-yl)oxy]piperidine-1-carboxylate (Preparation 9, 0.300 g, 0.67 mmol) was added, the reaction mixture was stirred overnight at room temperature. The solid that had formed was filtered and the clean solution was concentrated in vacuo to yield 0.297 g (100% yield) of the title compound, which was used without further purification in the next synthetic step.
LRMS (m/z): 444 (M+1)+.

b) 3-{5-Fluoro-4-methoxy-6-[(3R)-piperidin-3-yloxy]pyrimidin-2-yl}pyrazolo[1,5-a]pyridine Obtained as a pale white solid (55%) from tert-butyl (3R)-3-[(5-fluoro-6-methoxy-2-pyrazolo[1,5-a]pyridin-3-ylpyrimidin-4-yl)oxy]piperidine-1-carboxylate (Example 63a) following the experimental procedure as described in Example 20b.
LRMS (m/z): 344 (M+1)+.

c) 2-{(3R)-3-[(5-Fluoro-6-methoxy-2-pyrazolo[1,5-a]pyridin-3-ylpyrimidin-4-yl)oxy]piperidin-1-yl}-2-oxoethanol Obtained as a white solid (38%) from 3-{5-fluoro-4-methoxy-6-[(3R)-piperidin-3-yloxy]pyrimidin-2-yl}pyrazolo[1,5-a]pyridine (Example 63b) following the experimental procedure as described in Preparation 7. The crude was purified first by flash chromatography (dichloromethane to 95:5 dichloromethane/methanol) and then by reverse phase chromatography (C-18 silica from Waters®, water/1:1 acetonitrile-methanol as eluents [0.1% v/v ammonium formate buffered] 0% to 100%).
LRMS (m/z): 402 (M+1)+.
$^1$H-NMR (400 MHz, CDCl$_3$): δ 1.89-2.33 (m, 4H), 3.16-3.69 (m, 4H), 3.77-4.44 (m, 6H), 5.29 (dt, 1H), 6.82-6.99 (m, 1H), 7.29-7.43 (m, 1H), 8.35-8.47 (m, 1H), 8.49-8.68 (m, 2H).

Example 64

3-{(3R)-3-[(5-Fluoro-6-methoxy-2-pyrazolo[1,5-a]pyridin-3-ylpyrimidin-4-yl)oxy]piperidin-1-yl}-3-oxopropanenitrile Obtained as a white solid (43%) from 3-{5-fluoro-4-methoxy-6-[(3R)-piperidin-3-yloxy]pyrimidin-2-yl}pyrazolo[1,5-a]pyridine (Example 63b) following the experimental procedure as described in Preparation 6b. The crude was purified first by flash chromatography (gradient from dichloromethane to dichloromethane/methanol 85:15) and then by reverse phase chromatography (C-18 silica from Waters®, water/1:1 acetonitrile-methanol as eluents [0.1% v/v ammonium formate buffered] 0% to 100%).
LRMS (m/z): 411 (M+1)+.
$^1$H-NMR (400 MHz, CDCl$_3$): δ 1.72-2.29 (m, 4H), 3.28-3.64 (m, 4H), 3.64-3.89 (m, 2H), 4.17 (d, 3H), 5.27-5.43 (m, 1H), 6.85-6.98 (m, 1H), 7.32-7.45 (m, 1H), 8.33-8.48 (m, 1H), 8.48-8.66 (m, 2H).

Example 65

2-((3R)-3-{[5-Fluoro-6-(2-hydroxyethoxy)-2-pyrazolo[1,5-a]pyridin-3-ylpyrimidin-4-yl]oxy}piperidin-1-yl)-2-oxoethanol a) Tert-butyl (3R)-3-{[5-fluoro-6-(2-hydroxyethoxy)-2-pyrazolo[1,5-a]pyridin-3-ylpyrimidin-4-yl]oxy}piperidine-1-carboxylate A mixture of tert-butyl (3R)-3-[(6-chloro-5-fluoro-2-pyrazolo[1,5-a]pyridin-3-ylpyrimidin-4-yl)oxy]piperidine-1-carboxylate (Preparation 9, 0.250 g, 0.56 mmol) and cesium fluoride (0.42 g, 2.77 mmol) in dimethyl sulfoxide (10 mL) was stirred at 80° C. for 2 hours. Then it was allowed to cool to room temperature and ethylene glycol (0.310 mL, 5.56 mmol) was added. The solution was stirred at 80° C. for one hour and at room temperature for 16 hours, then it was partitioned between water and ethyl acetate. The organic layer was separated and washed with water and brine, dried over magnesium sulfate, filtered and the solvents were removed in vacuo. The crude was purified by flash chromatography (gradient from dichloromethane to dichloromethane/methanol 95:5) to give the title compound (87% yield) as a white solid
LRMS (m/z): 474 (M+1)+.

b) 2-({5-Fluoro-6-[(3R)-piperidin-3-yloxy]-2-pyrazolo[1,5-a]pyridin-3-ylpyrimidin-4-yl}oxy)ethanol To a solution of tert-butyl (3R)-3-{[5-fluoro-6-(2-hydroxyethoxy)-2-pyrazolo[1,5-a]pyridin-3-ylpyrimidin-4-yl]oxy}piperidine-1-carboxylate (Example 65a, 0.229 g, 0.48 mmol) in dichloromethane (5 mL) was added trifluoroacetic acid (0.37 mL) and the resulting mixture was stirred at room temperature for 2 hours. The volatiles were evaporated under reduced pressure and the residue was treated with a saturated aqueous solution of sodium bicarbonate (30 mL) and stirred vigorously for 1 hour. Then the product was extracted with dichloromethane (×3) and the combined organic layers were washed with brine, dried over magnesium sulfate and evaporated to dryness to yield the title compound (0.174 g, 96%) as a white solid.
LRMS (m/z): 374 (M+1)+.

c) 2-((3R)-3-{[5-Fluoro-6-(2-hydroxyethoxy)-2-pyrazolo[1,5-a]pyridin-3-ylpyrimidin-4-yl]oxy}piperidin-1-yl)-2-oxoethanol A mixture of 2-({5-fluoro-6-[(3R)-piperidin-3-yloxy]-2-pyrazolo[1,5-a]pyridin-3-ylpyrimidin-4-yl}oxy)ethanol (Example 65b, 0.087 g, 0.23 mmol), 2-hydroxyacetic acid (0.021 g, 0.28 mmol), 1-[bis(dimethylamino)methylene]-1H-1,2,3-triazolo[4,5-b]pyridinium-3-oxide hexafluorophosphate (0.106 g, 1.20 mmol) and triethylamine (0.097 mL, 0.70 mmol) in N,N-dimethylformamide (2 mL) was stirred at room temperature for 64 hours. The resulting mixture was partitioned between aqueous saturated solution of sodium bicarbonate and ethyl acetate, the organic layer was separated and the aqueous phase was extracted twice with ethyl acetate. The combined organic layers were washed with water, brine, dried over magnesium sulfate and concentrated in vacuo. The resulting crude was purified by flash chromatography (gradient from dichloromethane to dichloromethane/methanol 92:8) to yield the title compound (0.048 g, 48%) as a white solid.

LRMS (m/z): 432 (M+1)$^+$.

$^1$H-NMR (400 MHz, CDCl$_3$): δ 1.92-2.33 (m, 4H), 3.17-3.75 (m, 4H), 3.81-4.40 (m, 5H), 4.61-4.73 (m, 2H), 5.23-5.37 (m, 1H), 6.84-6.97 (m, 1H), 7.29-7.42 (m, 1H), 8.35 (dd, 1H), 8.46-8.66 (m, 2H).

Example 66

3-((3R)-3-{[5-Fluoro-6-(2-hydroxyethoxy)-2-pyrazolo[1,5-a]pyridin-3-ylpyrimidin-4-yl]oxy}piperidin-1-yl)-3-oxopropanenitrile 3-[(2,5-Dioxopyrrolidin-1-yl)oxy]-3-oxopropanenitrile (prepared as described in BE875054(A1), 0.051 g, 0.28 mmol) was added to a solution of 2-({5-fluoro-6-[(3R)-piperidin-3-yloxy]-2-pyrazolo[1,5-a]pyridin-3-ylpyrimidin-4-yl}oxy)ethanol (Example 65b, 0.087 g, 0.23 mmol) and triethylamine (0.065 mL, 0.47 mmol) in dichloromethane (3 mL). The resulting mixture was stirred at room temperature for 68 hours. A saturated aqueous solution of sodium bicarbonate (20 mL) was added and the mixture was stirred vigorously for 30 minutes. Then methylene chloride was added, the organic layer was separated and the aqueous phase was extracted twice with more methylene chloride. The combined organic layers were washed with water, brine, dried over magnesium sulfate and concentrated in vacuo. The resulting crude was purified first by flash chromatography (gradient from dichloromethane to dichloromethane/methanol 92:8) and then by reverse phase chromatography (C-18 silica from Waters®, water/1:1 acetonitrile-methanol as eluents [0.1% v/v ammonium formate buffered] 0% to 100%) to yield the title compound (0.049 g, 48%) as a white solid.

LRMS (m/z): 441 (M+1)$^+$.

$^1$H-NMR (400 MHz, CDCl$_3$): δ 1.85-2.31 (m, 4H), 3.19-3.92 (m, 5H), 3.95-4.18 (m, 3H), 4.63-4.74 (m, 2H), 5.26-5.44 (m, 1H), 6.85-6.98 (m, 1H), 7.33-7.45 (m, 1H), 8.28-8.43 (m, 1H), 8.48-8.64 (m, 2H).

Example 67

2-((3R)-3-{[5-Fluoro-6-(4-methylpiperazin-1-yl)-2-pyrazolo[1,5-a]pyridin-3-ylpyrimidin-4-yl]oxy}piperidin-1-yl)-2-oxoethanol a) Tert-butyl (3R)-3-{[5-fluoro-6-(4-methylpiperazin-1-yl)-2-pyrazolo[1,5-a]pyridin-3-ylpyrimidin-4-yl]oxy}piperidine-1-carboxylate A mixture of tert-butyl (3R)-3-[(6-chloro-5-fluoro-2-pyrazolo[1,5-a]pyridin-3-ylpyrimidin-4-yl)oxy]piperidine-1-carboxylate (Preparation 9, 0.250 g, 0.56 mmol) and 1-methylpiperazine (0.224 g, 2.23 mmol) in tetrahydrofurane (2 mL) was stirred at reflux temperature overnight. Then the reaction mixture was partitioned between water and ethyl acetate, the organic layer was separated and the aqueous phase was extracted twice with ethyl acetate. The combined organic layers were washed with water, brine, dried over magnesium sulfate and concentrated in vacuo to yield the title compound (0.285 g, 100%) as an oil.

LRMS (m/z): 512 (M+1)$^+$.

b) 3-{5-Fluoro-4-(4-methylpiperazin-1-yl)-6-[(3R)-piperidin-3-yloxy]pyrimidin-2-yl}pyrazolo[1,5-a]pyridine To a solution of tert-butyl (3R)-3-{[5-fluoro-6-(4-methylpiperazin-1-yl)-2-pyrazolo[1,5-a]pyridin-3-ylpyrimidin-4-yl]oxy}piperidine-1-carboxylate (Example 67a, 0.285 g, 0.56 mmol) in dioxane (3 mL) was added a 4 M solution of hydrochloric acid (2.6 mL) and the resulting mixture was stirred at room temperature for 2 hours. The volatiles were evaporated under reduced pressure to give the title compound as a dichlorohydrate (0.270 g, 100%) as a brownish solid.

LRMS (m/z): 412 (M+1)$^+$.

c) 2-((3R)-3-{[5-Fluoro-6-(4-methylpiperazin-1-yl)-2-pyrazolo[1,5-a]pyridin-3-ylpyrimidin-4-yl]oxy}piperidin-1-yl)-2-oxoethanol A mixture of 2-hydroxyacetic acid (0.040 g, 0.53 mmol) and 1-[bis(dimethylamino)methylene]-1H-1,2,3-triazolo[4,5-b]pyridinium-3-oxide hexafluorophosphate (0.220 g, 0.58 mmol) in N,N-dimethylformamide (1.5 mL) was stirred at room temperature for 30 minutes. A solution of 3-{5-fluoro-4-(4-methylpiperazin-1-yl)-6-[(3R)-piperidin-3-yloxy]pyrimidin-2-yl}pyrazolo[1,5-a]pyridine dichlorohydrate salt (Example 67b, 0.198 g, 0.48 mmol) and triethylamine (0.335 mL, 2.4 mmol) in N,N-dimethylformamide (1.5 mL) was added and the resulting mixture was stirred at room temperature overnight. Then water was added and the product was extracted with methylene chloride (×3). The combined organic layers were washed with water, brine, dried over magnesium sulfate and concentrated in vacuo. The resulting crude was purified by reverse phase chromatography (C-18 silica from Waters®, water/1:1 acetonitrile-methanol as eluents 0% to 100%) to yield the title compound (0.062 g, 27%) as a white solid.

LRMS (m/z): 470 (M+1)$^+$.

$^1$H-NMR (400 MHz, CDCl$_3$): δ 1.90-2.26 (m, 4H), 2.27-2.52 (m, 3H), 2.66 (s, 4H), 3.12-4.38 (m, 11H), 5.28 (s, 1H), 6.81-6.96 (m, 1H), 7.28-7.38 (m, 1H), 8.34 (dd, 1H), 8.45-8.62 (m, 2H).

Example 68

3-((3R)-3-{[5-Fluoro-6-(4-methylpiperazin-1-yl)-2-pyrazolo[1,5-a]pyridin-3-ylpyrimidin-4-yl]oxy}piperidin-1-yl)-3-oxopropanenitrile 3-[(2,5-Dioxopyrrolidin-1-yl)oxy]-3-oxopropanenitrile (prepared as described in BE875054(A1), 0.175 g, 0.96 mmol) was added to a solution of 3-{5-fluoro-4-(4-methylpiperazin-1-yl)-6-[(3R)-piperidin-3-yloxy]pyrimidin-2-yl}pyrazolo[1,5-a]pyridine dichlorohydrate salt (Example 67b, 0.198 g, 0.48 mmol) and triethylamine (0.335 mL, 2.41 mmol) in dichloromethane (25 mL). The resulting mixture was stirred overnight at room temperature and then it was diluted with methylene chloride. The solution was washed with water, brine, dried over magnesium sulfate and concentrated in vacuo. The resulting crude was purified by reverse phase chromatography (C-18 silica from Waters®, water/1:1 acetonitrile-methanol as eluents 0% to 100%) to yield the title compound (0.018 g, 8%) as a white solid.

LRMS (m/z): 479 (M+1)+.

1H-NMR (400 MHz, CDCl3): δ 1.85-2.31 (m, 4H), 2.47 (d, 7H), 3.09-3.96 (m, 9H), 4.01-4.27 (m, 1H), 5.31 (s, 1H), 6.75-6.98 (m, 1H), 7.29-7.42 (m, 1H), 8.20-8.42 (m, 1H), 8.42-8.63 (m, 2H).

Example 69

2-[(3R)-3-({5-Fluoro-6-[(2-hydroxyethyl)amino]-2-pyrazolo[1,5-a]pyridin-3-ylpyrimidin-4-yl}oxy)piperidin-1-yl]-2-oxoethanol a) Tert-butyl (3R)-3-({5-fluoro-6-[(2-hydroxyethyl)amino]-2-pyrazolo[1,5-a]pyridin-3-ylpyrimidin-4-yl}oxy)piperidine-1-carboxylate A solution of tert-butyl (3R)-3-[(6-chloro-5-fluoro-2-pyrazolo[1,5-a]pyridin-3-ylpyrimidin-4-yl)oxy]piperidine-1-carboxylate (Preparation 9, 0.250 g, 0.56 mmol) and 2-aminoethanol (0.340 g, 5.58 mmol) in dioxane (2 mL) was stirred at reflux temperature overnight. Then the reaction mixture was partitioned between water and ethyl acetate, the organic layer was separated and the aqueous phase was extracted twice with ethyl acetate. The combined organic layers were washed with water, brine, dried over magnesium sulfate and concentrated in vacuo to yield the title compound (0.264 g, 100%) as an oil.

LRMS (m/z): 473 (M+1)+.

b) 2-({5-Fluoro-6-[(3R)-piperidin-3-yloxy]-2-pyrazolo[1,5-a]pyridin-3-ylpyrimidin-4-yl}amino)ethanol Prepared from tert-butyl (3R)-3-({5-fluoro-6-[(2-hydroxyethyl)amino]-2-pyrazolo[1,5-a]pyridin-3-ylpyrimidin-4-yl}oxy)piperidine-1-carboxylate (Example 69a, 0.263 g, 0.56 mmol) following the experimental procedure as described in Example 67b to give the title compound (100% yield) as the dichlorohydrate salt.

LRMS (m/z): 373 (M+1)+.

c) 2-[(3R)-3-({5-Fluoro-6-[(2-hydroxyethyl)amino]-2-pyrazolo[1,5-a]pyridin-3-ylpyrimidin-4-yl}oxy)piperidin-1-yl]-2-oxoethanol Prepared from 2-({5-fluoro-6-[(3R)-piperidin-3-yloxy]-2-pyrazolo[1,5-a]pyridin-3-ylpyrimidin-4-yl}amino)ethanol dichlorohydrate salt (Example 69b, 0.156 g, 0.42 mmol) following the experimental procedure as described in Example 67c. The crude product was purified by reverse phase chromatography (C-18 silica from Waters®, water/1:1 acetonitrile-methanol as eluents 0% to 100%) to yield the title compound (0.072 g, 39%) as a white solid.

LRMS (m/z): 431 (M+1)+.

1H-NMR (400 MHz, CDCl3): δ 1.89-2.27 (m, 4H), 3.17-4.01 (m, 9H), 4.01-4.39 (m, 2H), 5.21-5.40 (m, 2H), 6.81-6.95 (m, 1H), 7.28-7.38 (m, 1H), 8.30-8.44 (m, 1H), 8.45-8.66 (m, 2H).

Example 70

3-[(3R)-3-({5-Fluoro-6-[(2-hydroxyethyl)amino]-2-pyrazolo[1,5-a]pyridin-3-ylpyrimidin-4-yl}oxy)piperidin-1-yl]-3-oxopropanenitrile Obtained as a light yellow solid (42%) from 2-({5-fluoro-6-[(3R)-piperidin-3-yloxy]-2-pyrazolo[1,5-a]pyridin-3-ylpyrimidin-4-yl}amino)ethanol dichlorohydrate salt (Example 69b) following the experimental procedure as described in Preparation 6b. The crude product was purified by reverse phase chromatography (C-18 silica from Waters®, water/1:1 acetonitrile-methanol as eluents 0% to 100%).

LRMS (m/z): 440 (M+1)+.

1H-NMR (400 MHz, CDCl3): δ 1.86-2.34 (m, 4H), 3.14-4.23 (m, 11H), 5.20-5.47 (m, 2H), 6.77-6.98 (m, 1H), 7.26-7.43 (m, 1H), 8.27-8.46 (m, 1H), 8.46-8.65 (m, 2H).

Example 71

2-((3R)-3-{[5-Fluoro-6-(2-methylpyridin-4-yl)-2-pyrazolo[1,5-a]pyridin-3-ylpyrimidin-4-yl]oxy}piperidin-1-yl)-2-oxoethanol a) Tert-butyl (3R)-3-{[5-fluoro-6-(2-methylpyridin-4-yl)-2-pyrazolo[1,5-a]pyridin-3-ylpyrimidin-4-yl]oxy}piperidine-1-carboxylate Obtained as a light yellow solid (95%) from tert-butyl (3R)-3-[(6-chloro-5-fluoro-2-pyrazolo[1,5-a]pyridin-3-ylpyrimidin-4-yl)oxy]piperidine-1-carboxylate (Preparation 9, 0.300 g, 0.67 mmol) and (2-methylpyridin-4-yl)boronic acid following the experimental procedure as described in Example 34 followed by purification by flash chromatography (gradient from dichloromethane to dichloromethane/methanol 85:15).

LRMS (m/z): 505 (M+1)+.

b) 3-{5-Fluoro-4-(2-methylpyridin-4-yl)-6-[(3R)-piperidin-3-yloxy]pyrimidin-2-yl}pyrazolo[1,5-a]pyridine Prepared from tert-butyl (3R)-3-{[5-fluoro-6-(2-methylpyridin-4-yl)-2-pyrazolo[1,5-a]pyridin-3-ylpyrimidin-4-yl]oxy}piperidine-1-carboxylate (Example 71a, 0.326 g, 0.65 mmol) following the experimental procedure as described in Example 67b to give the title compound (100% yield) as the dichlorohydrate salt.

LRMS (m/z): 405 (M+1)+.

c) 2-((3R)-3-{[5-Fluoro-6-(2-methylpyridin-4-yl)-2-pyrazolo[1,5-a]pyridin-3-ylpyrimidin-4-yl]oxy}piperidin-1-yl)-2-oxoethanol Prepared from 3-{5-fluoro-4-(2-methylpyridin-4-yl)-6-[(3R)-piperidin-3-yloxy]pyrimidin-2-yl}pyrazolo[1,5-a]pyridine dichlorohydrate salt (Example 71b, 0.179 g, 0.44 mmol) following the experimental procedure as described in Example 67c. The crude product was purified by reverse phase chromatography (C-18 silica from Waters®, water/1:1 acetonitrile-methanol as eluents 0% to 100%) followed by stirring in a mixture of methanol (5 mL), water (1 mL) and a few drops of a 2 M solution of sodium hydroxide for 3 hours. Then the product was extracted with methylene chloride (×3) and the organic solution washed with water and brine, dried over magnesium sulfate, filtered and the solvents removed in vacuo to yield the pure title compound (0.082 g, 40%) as a white solid.

LRMS (m/z): 463 (M+1)+.

1H-NMR (400 MHz, CDCl3): δ 1.93-2.34 (m, 4H), 2.74 (s, 3H), 3.21-4.46 (m, 7H), 5.43 (s, 1H), 6.86-7.01 (m, 1H), 7.31-7.49 (m, 1H), 7.80-8.00 (m, 2H), 8.48 (t, 1H), 8.53-8.60 (m, 1H), 8.61-8.77 (m, 2H).

Example 72

3-((3R)-3-{[5-Fluoro-6-(2-methylpyridin-4-yl)-2-pyrazolo[1,5-a]pyridin-3-ylpyrimidin-4-yl]oxy}piperidin-1-yl)-3-oxopropanenitrile Obtained as a light yellow solid (49%) from 3-{5-fluoro-4-(2-methylpyridin-4-yl)-6-[(3R)-piperidin-3-yloxy]pyrimidin-2-yl}pyrazolo[1,5-a]pyridine dichlorohydrate salt (Example 71b) following the experimental procedure as described in Preparation 6b. The crude product was purified by flash chromatography (gradient from dichloromethane to dichloromethane/methanol 85:15).

LRMS (m/z): 472 (M+1)$^+$.

$^1$H-NMR (400 MHz, CDCl$_3$): δ 1.89-2.42 (m, 4H), 2.73 (s, 3H), 3.21-4.30 (m, 6H), 5.49 (s, 1H), 6.84-7.04 (m, 1H), 7.41 (s, 1H), 7.77-8.00 (m, 2H), 8.42-8.52 (m, 1H), 8.52-8.60 (m, 1H), 8.60-8.80 (m, 2H).

Example 73

3-[(3R)-3-({5-Fluoro-6-[2-(hydroxymethyl)pyridin-4-yl]-2-pyrazolo[1,5-a]pyridin-3-ylpyrimidin-4-yl}oxy)piperidin-1-yl]-3-oxopropanenitrile a) Tert-butyl (3R)-3-[(5-fluoro-2-pyrazolo[1,5-a]pyridin-3-yl-6-{2-[(tetrahydro-2H-pyran-2-yloxy)methyl]pyridin-4-yl}pyrimidin-4-yl)oxy]piperidine-1-carboxylate Obtained as a pale solid (90%) from tert-butyl (3R)-3-[(6-chloro-5-fluoro-2-pyrazolo[1,5-a]pyridin-3-ylpyrimidin-4-yl)oxy]piperidine-1-carboxylate (Preparation 9, 0.150 g, 0.34 mmol) and 2-[(tetrahydro-2H-pyran-2-yloxy)methyl]-4-(4,4,5,5-tetramethyl-1,3,2-dioxaborolan-2-yl)pyridine (Example 37b) following the experimental procedure as described in Example 20a followed by purification by flash chromatography (gradient from hexane to hexane/ethyl acetate 30:70).

LRMS (m/z): 606 (M+1)$^+$.

b) (4-{5-Fluoro-6-[(3R)-piperidin-3-yloxy]-2-pyrazolo[1,5-a]pyridin-3-ylpyrimidin-4-yl}pyridin-2-yl)methanol To a solution of tert-butyl (3R)-3-[(5-fluoro-2-pyrazolo[1,5-a]pyridin-3-yl-6-{2-[(tetrahydro-2H-pyran-2-yloxy)methyl]pyridin-4-yl}pyrimidin-4-yl)oxy]piperidine-1-carboxylate (Example 73a, 0.182 g, 0.30 mmol) in tetrahydrofurane (2 mL) was added 2 M hydrochloric acid (0.45 mL). The resulting solution was stirred at 60° C. for 5 hours and at room temperature for 16 hours. Then it was diluted with water, basified with 2 M sodium hydroxide solution and extracted with methylene chloride (×3). The combined organic layer was washed with brine, dried over magnesium sulfate, filtered and the solvent was removed to yield the title compound (0.126 g, 100%) as a pale solid.

LRMS (m/z): 421 (M+1)$^+$.

c) 3-[(3R)-3-({5-Fluoro-6-[2-(hydroxymethyl)pyridin-4-yl]-2-pyrazolo[1,5-a]pyridin-3-ylpyrimidin-4-yl}oxy)piperidin-1-yl]-3-oxopropanenitrile Obtained as a white solid (34%) from (4-{5-fluoro-6-[(3R)-piperidin-3-yloxy]-2-pyrazolo[1,5-a]pyridin-3-ylpyrimidin-4-yl}pyridin-2-yl)methanol (Example 73b) following the experimental procedure as described in Preparation 6b. The crude was purified by flash chromatography (dichloromethane to 90:10 dichloromethane/methanol).

LRMS (m/z): 488 (M+1)$^+$.

$^1$H-NMR (400 MHz, CDCl$_3$): δ 1.92-2.38 (m, 3H), 3.02-4.37 (m, 7H), 4.92 (s, 2H), 5.34-5.57 (m, 1H), 6.86-7.05 (m, 1H), 7.33-7.51 (m, 1H), 7.97 (s, 1H), 8.00 (s, 1H), 8.44-8.53 (m, 1H), 8.53-8.61 (m, 1H), 8.62-8.75 (m, 1H), 8.75-8.84 (m, 1H).

Example 74

2-[(3R)-3-({5-Fluoro-6-[2-(hydroxymethyl)pyridin-4-yl]-2-pyrazolo[1,5-a]pyridin-3-ylpyrimidin-4-yl}oxy)piperidin-1-yl]-2-oxoethanol Obtained as a light yellow solid (58%) from (4-{5-Fluoro-6-[(3R)-piperidin-3-yloxy]-2-pyrazolo[1,5-a]pyridin-3-ylpyrimidin-4-yl}pyridin-2-yl)methanol (Example 73b) following the experimental procedure as described in Preparation 7. The crude product was purified by flash chromatography (gradient from dichloromethane to dichloromethane/methanol 90:10).

LRMS (m/z): 479 (M+1)$^+$.

$^1$H-NMR (400 MHz, CDCl$_3$): δ 1.78-2.43 (m, 4H), 3.24-4.24 (m, 7H), 4.94 (s, 2H), 5.42-5.57 (m, 1H), 6.89-7.03 (m, 1H), 7.37-7.49 (m, 1H), 7.90-8.12 (m, 2H), 8.40-8.51 (m, 1H), 8.57 (t, 1H), 8.62-8.73 (m, 1H), 8.78 (t, 1H).

Example 75

1-(5-Fluoro-6-{[(3R)-1-glycoloylpiperidin-3-yl]oxy}-2-pyrazolo[1,5-a]pyridin-3-ylpyrimidin-4-yl)piperidin-4-ol a) Tert-butyl (3R)-3-{[5-fluoro-6-(4-hydroxypiperidin-1-yl)-2-pyrazolo[1,5-a]pyridin-3-ylpyrimidin-4-yl]oxy}piperidine-1-carboxylate A mixture of tert-butyl (3R)-3-[(6-chloro-5-fluoro-2-pyrazolo[1,5-a]pyridin-3-ylpyrimidin-4-yl)oxy]piperidine-1-carboxylate (Preparation 9, 0.300 g, 0.67 mmol) and piperidin-4-ol (0.271 g, 2.68 mmol) in dimethylacetamide (2 mL) was stirred at 110° C. for 1 hour. Then the reaction mixture was partitioned between water and ethyl acetate, the organic layer was separated and the aqueous phase was extracted twice with ethyl acetate. The combined organic layers were washed with water, brine, dried over magnesium sulfate and concentrated in vacuo to yield the title compound (0.332 g, 100%) as an oil.

LRMS (m/z): 513 (M+1)$^+$.

b) 1-{5-Fluoro-6-[(3R)-piperidin-3-yloxy]-2-pyrazolo[1,5-a]pyridin-3-ylpyrimidin-4-yl}piperidin-4-ol Prepared from tert-butyl (3R)-3-{[5-fluoro-6-(4-hydroxypiperidin-1-yl)-2-pyrazolo[1,5-a]pyridin-3-ylpyrimidin-4-yl]oxy}piperidine-1-carboxylate (Example 75a, 0.332 g, 0.65 mmol) following the experimental procedure as described in Example 67b to give the title compound (100% yield) as the dichlorohydrate salt.

LRMS (m/z): 413 (M+1)$^+$.

c) 1-(5-Fluoro-6-{[(3R)-1-glycoloylpiperidin-3-yl]oxy}-2-pyrazolo[1,5-a]pyridin-3-ylpyrimidin-4-yl)piperidin-4-ol Prepared from 1-{5-fluoro-6-[(3R)-piperidin-3-yloxy]-2-pyrazolo[1,5-a]pyridin-3-ylpyrimidin-4-yl}piperidin-4-ol dichlorohydrate salt (Example 75b, 0.133 g, 0.32 mmol) following the experimental procedure as described in Example 67c. The crude product was purified by flash chromatography (gradient from 100% dichloromethane to 100% methanol) to yield the pure title compound (0.106 g, 70%) as a white solid.

LRMS (m/z): 471 (M+1)$^+$.

$^1$H-NMR (400 MHz, DMSO-d6): δ 1.07-2.15 (m, 10H), 2.91-3.11 (m, 2H), 3.53-4.34 (m, 6H), 4.38-4.63 (m, 1H), 4.78 (s, 1H), 5.00-5.36 (m, 1H), 6.91-7.12 (m, 1H), 7.34-7.60 (m, 1H), 8.23-8.42 (m, 1H), 8.48-8.66 (m, 1H), 8.69-8.86 (m, 1H).

Example 76

3-((3R)-3-{[5-Fluoro-6-(4-hydroxypiperidin-1-yl)-2-pyrazolo[1,5-a]pyridin-3-ylpyrimidin-4-yl]oxy}piperidin-1-yl)-3-oxopropanenitrile Obtained as a white solid (62%) from 1-{5-Fluoro-6-[(3R)-piperidin-3-yloxy]-2-pyrazolo[1,5-a]pyridin-3-ylpyrimidin-4-yl}piperidin-4-ol dichlorohydrate (Example 75b) following the experimental procedure as described in Preparation 6b. The crude was purified first by flash chromatography (dichloromethane to 90:10 dichloromethane/methanol) and then by reverse phase chromatography (C-18 silica from Waters®, water/1:1 acetonitrile-methanol as eluents [0.1% v/v ammonium formate buffered] 0% to 100%).

LRMS (m/z): 488 (M+1)$^+$.

$^1$H-NMR (400 MHz, CDCl$_3$): δ 1.62-2.35 (m, 8H), 3.12-4.33 (m, 12H), 5.31 (s, 1H), 6.79-6.96 (m, 1H), 7.28-7.39 (m, 1H), 8.27-8.44 (m, 1H), 8.45-8.61 (m, 2H).

Example 77

2-{(3R)-3-[[5-Fluoro-6-(2-methylpyridin-4-yl)-2-pyrazolo[1,5-a]pyridin-3-ylpyrimidin-4-yl](methyl)amino]piperidin-1-yl}-2-oxoethanol A mixture of 2-hydroxyacetic acid (0.016 g, 0.21 mmol) and 1-[bis(dimethylamino)methylene]-1H-1,2,3-triazolo[4,5-b]pyridinium-3-oxide hexafluorophosphate (0.082 g, 0.22 mmol) in N,N-dimethylformamide (2 mL) was stirred at room temperature for 15 minutes. 5-fluoro-N-methyl-6-(2-methylpyridin-4-yl)-N-[(3R)-piperidin-3-yl]-2-pyrazolo[1,5-a]pyridin-3-ylpyrimidin-4-amine (Example 21b, 0.075 g, 0.18 mmol) and triethylamine (0.150 mL, 1.1 mmol) were added and the resulting mixture was stirred at room temperature for 2 hours. Then water (50 mL) and a 2 M sodium hydroxide aqueous solution (5 mL) were added and the resulting solution was stirred for 30 minutes. Then the product was extracted with ethyl acetate (×3), the combined organic layers were washed with water, brine, dried over magnesium sulfate and concentrated in vacuo. The crude product was purified by flash chromatography (dichloromethane to 92:8 dichloromethane/methanol) to yield the title compound (0.055 g, 64%) as a white solid.

LRMS (m/z): 476 (M+1)$^+$.

$^1$H-NMR (400 MHz, CDCl$_3$): δ 1.62-2.25 (m, 4H), 2.50-3.34 (m, 8H), 3.41-3.78 (m, 2H), 4.03-4.35 (m, 2H), 4.41-4.61 (m, 1H), 4.61-5.03 (m, 1H), 6.80-6.95 (m, 1H), 7.31 (q, 1H), 7.73-7.98 (m, 2H), 8.45 (d, 1H), 8.49-8.59 (m, 1H), 8.59-8.74 (m, 2H).

Example 78

3-[(3R)-3-({5-Fluoro-6-[2-(hydroxymethyl)pyridin-4-yl]-2-pyrazolo[1,5-a]pyridin-3-ylpyrimidin-4-yl}amino)piperidin-1-yl]-3-oxopropanenitrile a) Tert-butyl (3R)-3-[(5-fluoro-2-pyrazolo[1,5-a]pyridin-3-yl-6-{2-[(tetrahydro-2H-pyran-2-yloxy)methyl]pyridin-4-yl}pyrimidin-4-yl)amino]piperidine-1-carboxylate Obtained as a pale solid (90%) from tert-butyl (3R)-3-[(6-chloro-5-fluoro-2-pyrazolo[1,5-a]pyridin-3-ylpyrimidin-4-yl) amino]piperidine-1-carboxylate (Preparation 5, 0.250 g, 0.56 mmol) and 2-[(tetrahydro-2H-pyran-2-yloxy)methyl]-4-(4,4,5,5-tetramethyl-1,3,2-dioxaborolan-2-yl)pyridine (Example 37b, 0.268 g, 0.84 mmol) following the experimental procedure as described in Example 20a.

LRMS (m/z): 605 (M+1)$^+$.

b) (4-{5-Fluoro-6-[(3R)-piperidin-3-ylamino]-2-pyrazolo[1,5-a]pyridin-3-ylpyrimidin-4-yl}pyridin-2-yl)methanol Obtained as a white solid (99%) from tert-butyl (3R)-3-[(5-fluoro-2-pyrazolo[1,5-a]pyridin-3-yl-6-{2-[(tetrahydro-2H-pyran-2-yloxy)methyl]pyridin-4-yl}pyrimidin-4-yl) amino]piperidine-1-carboxylate (Example 78a) following the experimental procedure as described in Example 73b.

LRMS (m/z): 420 (M+1)$^+$.

c) 3-[(3R)-3-({5-Fluoro-6-[2-(hydroxymethyl)pyridin-4-yl]-2-pyrazolo[1,5-a]pyridin-3-ylpyrimidin-4-yl}amino)piperidin-1-yl]-3-oxopropanenitrile Obtained as a white solid (31%) from (4-{5-fluoro-6-[(3R)-piperidin-3-ylamino]-2-pyrazolo[1,5-a]pyridin-3-ylpyrimidin-4-yl}pyridin-2-yl)methanol (Example 78b) following the experimental procedure as described in Preparation 6b. The crude was purified by flash chromatography (dichloromethane to 92:8 dichloromethane/methanol).

LRMS (m/z): 487 (M+1)$^+$.

$^1$H-NMR (400 MHz, CDCl$_3$): δ 1.74-2.33 (m, 4H), 3.18-4.60 (m, 8H), 4.82-4.98 (m, 2H), 5.19 (s, 1H), 6.77-7.05 (m, 1H), 7.39 (s, 1H), 7.79-8.07 (m, 2H), 8.36-8.86 (m, 4H).

Example 79

5-(5-Fluoro-6-{[(3R)-1-glycoloylpiperidin-3-yl]amino}-2-pyrazolo[1,5-a]pyridin-3-ylpyrimidin-4-yl)pyridine-2-carboxylic acid To a solution of ethyl 5-(5-fluoro-6-{[(3R)-1-glycoloylpiperidin-3-yl]amino}-2-pyrazolo[1,5-a]pyridin-3-ylpyrimidin-4-yl)pyridine-2-carboxylate (Example 38c, 0.120 g, 0.23 mmol) in a mixture of tetrahydrofurane (3 mL) and water (3 mL) was added a 2 M aqueous solution of sodium hydroxide (0.580 mL) and the resulting solution was stirred at room temperature overnight. Then the reaction mixture was diluted with water and acidified to pH=5 and directly injected for purification by reverse phase chromatography (C-18 silica from Waters®, water/1:1 acetonitrile-methanol as eluents [0.1% v/v ammonium formate buffered] 0% to 100%) to yield the title compound (0.039 g, 34%) as a white solid.

LRMS (m/z): 492 (M+1)$^+$.

Example 80

2-{(3R)-3-[(5-Fluoro-2-pyrazolo[1,5-a]pyridin-3-yl-6-pyridin-4-ylpyrimidin-4-yl)amino]piperidin-1-yl}-2-oxoethanol Obtained as a dark yellow solid (79%) from 3-{(3R)-3-[(6-chloro-5-fluoro-2-pyrazolo[1,5-a]pyridin-3-ylpyrimidin-4-yl)amino]piperidin-1-yl}-3-oxopropanenitrile (Preparation 7b) following the experimental procedure described in Example 20a.

LRMS (m/z): 448 (M+1)+.

$^1$H-NMR (400 MHz, CDCl$_3$): δ 1.67-2.04 (m, 3H), 2.11-2.29 (m, 1H), 3.10-3.34 (m, 2H), 3.39-3.56 (m, 2H), 3.64-3.83 (m, 1H), 3.95-4.12 (m, 1H), 4.32 (d, 1H), 4.58-4.76 (m, 1H), 5.08-5.22 (m, 1H), 6.85-6.94 (m, 1H), 7.30-7.42 (m, 1H), 8.00 (d, 2H), 8.53 (dt 2H), 8.61-8.84 (m, 3H).

Example 81

2-[(3R)-3-({6-[6-(Dimethylamino)pyridin-3-yl]-5-fluoro-2-pyrazolo[1,5-a]pyridin-3-ylpyrimidin-4-yl}amino)piperidin-1-yl]-2-oxoethanol Obtained from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7, 0.098 g, 0.24 mmol) and N,N-dimethyl-5-(4,4,5,5-tetramethyl-1,3,2-dioxaborolan-2-yl)pyridin-2-amine (prepared as described in Example 37b from 5-bromo-N,N-dimethylpyridin-2-amine) following the experimental procedure as described in Example 20a. The crude product was purified first by flash chromatography (dichloromethane to dichloromethane/methanol 98:2) and then by reverse phase chromatography (C-18 silica from Waters®, water/1:1 acetonitrile-methanol as eluents [0.1% v/v ammonium formate buffered] 0% to 100%) to yield the title compound (0.040 g, 34%) as a white solid.

LRMS (m/z): 491 (M+1)+.

$^1$H-NMR (400 MHz, CDCl$_3$): δ 1.67-2.38 (m, 4H), 3.06-3.29 (m, 6H), 3.33-5.09 (m, 9H), 6.53-6.71 (m, 1H), 6.79-6.97 (m, 1H), 7.28-7.39 (m, 1H), 8.28 (d, 1H), 8.45-8.79 (m, 3H), 9.04 (s, 1H).

Example 82

2-{(3R)-3-[(5-Fluoro-2'-methyl-2-pyrazolo[1,5-a]pyridin-3-yl-4,5'-bipyrimidin-6-yl)amino]piperidin-1-yl}-2-oxoethanol Obtained from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7, 0.098 g, 0.24 mmol) and 2-methyl-5-(4,4,5,5-tetramethyl-1,3,2-dioxaborolan-2-yl)pyrimidine (prepared as described in Example 37b from 5-bromo-2-methylpyrimidine) following the experimental procedure as described in Example 20a. The crude product was purified first by flash chromatography (dichloromethane to dichloromethane/methanol 95:5) and then by reverse phase chromatography (C-18 silica from Waters®, water/1:1 acetonitrile-methanol as eluents [0.1% v/v ammonium formate buffered] 0% to 100%) to yield the title compound (0.049 g, 44%) as a white solid.

LRMS (m/z): 463 (M+1)+.

$^1$H-NMR (400 MHz, CDCl$_3$): δ 1.68-2.40 (m, 4H), 2.85 (s, 3H), 3.09-4.75 (m, 8H), 5.06-5.31 (m, 1H), 6.79-6.98 (m, 1H), 7.26-7.42 (m, 1H), 8.32-8.86 (m, 3H), 9.39 (s, 2H).

Example 83

2-((3R)-3-{[6-(2-Ethoxyethoxy)-5-fluoro-2-pyrazolo[1,5-a]pyridin-3-ylpyrimidin-4-yl]amino}piperidin-1-yl)-2-oxoethanol a) Tert-butyl (3R)-3-{[6-(2-ethoxyethoxy)-5-fluoro-2-pyrazolo[1,5-a]pyridin-3-ylpyrimidin-4-yl]oxy}piperidine-1-carboxylate Obtained as a colorless solid (63%) from tert-butyl (3R)-3-[(6-chloro-5-fluoro-2-pyrazolo[1,5-a]pyridin-3-ylpyrimidin-4-yl)amino]piperidine-1-carboxylate (Preparation 5) and 2-ethoxyethanol following the experimental procedure described in Example 15a.

LRMS (m/z): 501 (M+1)+.

b) 3-{4-(2-Ethoxyethoxy)-5-fluoro-6-[(3R)-piperidin-3-yloxy]pyrimidin-2-yl}pyrazolo[1,5-a]pyridine Obtained as an oil (100%) from tert-butyl (3R)-3-{[6-(2-ethoxyethoxy)-5-fluoro-2-pyrazolo[1,5-a]pyridin-3-ylpyrimidin-4-yl]oxy}piperidine-1-carboxylate (Example 83a) following the experimental procedure described in Example 20b.

LRMS (m/z): 401 (M+1)+.

c) 2-((3R)-3-{[6-(2-Ethoxyethoxy)-5-fluoro-2-pyrazolo[1,5-a]pyridin-3-ylpyrimidin-4-yl]amino}piperidin-1-yl)-2-oxoethanol Obtained as a white solid (51%) from 3-{4-(2-ethoxyethoxy)-5-fluoro-6-[(3R)-piperidin-3-yloxy]pyrimidin-2-yl}pyrazolo[1,5-a]pyridine (Example 83b) following the experimental procedure described in Preparation 7 followed by purification by reverse phase chromatography (C-18 silica from Waters®, water/methanol as eluents 0% to 100%).

LRMS (m/z): 459 (M+1)+.

$^1$H-NMR (400 MHz, CDCl$_3$): δ 1.20-1.29 (m, 3H), 1.65-1.94 (m, 3H), 2.17 (s, 1H), 2.92-3.20 (m, 2H), 3.29-3.66 (m, 3H), 3.66-3.78 (m, 1H), 3.81-3.90 (m, 2H), 3.95-4.04 (m, 1H), 4.14-4.32 (m, 2H), 4.60-4.78 (m, 3H), 6.85 (q, 1H), 7.26-7.36 (m, 1H), 8.28-8.70 (m, 3H).

Example 84

2-[(3R)-3-({5-Fluoro-6-[6-(hydroxymethyl)pyridin-3-yl]-2-pyrazolo[1,5-a]pyridin-3-ylpyrimidin-4-yl}amino)piperidin-1-yl]-2-oxoethanol a) Tert-butyl (3R)-3-[(5-fluoro-2-pyrazolo[1,5-a]pyridin-3-yl-6-{6-[(tetrahydro-2H-pyran-2-yloxy)methyl]pyridin-3-yl}pyrimidin-4-yl)amino]piperidine-1-carboxylate Obtained from tert-butyl (3R)-3-[(6-chloro-5-fluoro-2-pyrazolo[1,5-a]pyridin-3-ylpyrimidin-4-yl) amino]piperidine-1-carboxylate (Preparation 5, 0.250 g, 0.56 mmol) and 2-[(tetrahydro-2H-pyran-2-yloxy)methyl]-5-(4,4,5,5-tetramethyl-1,3,2-dioxaborolan-2-yl)pyridine (prepared as described in Example 37a and 37b from (5-bromopyrimidin-2-yl)methanol) following the experimental procedure as described in Example 20a. The crude product was purified by flash chromatography (hexane to hexane/ethyl acetate 20:80) to yield the title compound (0.237 g, 70%) as a white solid.

LRMS (m/z): 605 (M+1)$^+$.

b) (5-{5-Fluoro-6-[(3R)-piperidin-3-ylamino]-2-pyrazolo[1,5-a]pyridin-3-ylpyrimidin-4-yl}pyridin-2-yl)methanol Obtained as a white solid (100%) from tert-butyl (3R)-3-[(5-fluoro-2-pyrazolo[1,5-a]pyridin-3-yl-6-{6-[(tetrahydro-2H-pyran-2-yloxy)methyl]pyridin-3-yl}pyrimidin-4-yl)amino]piperidine-1-carboxylate (Example 84a) following the experimental procedure as described in Example 73b.

LRMS (m/z): 420 (M+1)$^+$.

c) 2-[(3R)-3-({5-Fluoro-6-[6-(hydroxymethyl)pyridin-3-yl]-2-pyrazolo[1,5-a]pyridin-3-ylpyrimidin-4-yl}amino)piperidin-1-yl]-2-oxoethanol Prepared from (5-{5-Fluoro-6-[(3R)-piperidin-3-ylamino]-2-pyrazolo[1,5-a]pyridin-3-ylpyrimidin-4-yl}pyridin-2-yl)methanol (Example 84b, 0.065 g, 0.16 mmol) following the experimental procedure as described in Example 67c. The crude product was purified first by reverse phase chromatography (C-18 silica from Waters®, water/1:1 acetonitrile-methanol as eluents 0% to 100%) and then by preparative HPLC (gradient from water to methanol) to yield the pure title compound (0.005 g, 7%) as a white solid.

LRMS (m/z): 478 (M+1)$^+$.

$^1$H-NMR (400 MHz, CDCl$_3$): δ 1.68-2.30 (m, 3H), 2.98-4.95 (m, 11H), 5.01-5.23 (m, 1H), 6.82-6.98 (m, 1H), 7.29-7.57 (m, 2H), 8.39-8.60 (m, 2H), 8.60-8.80 (m, 1H), 9.32 (s, 1H).

Example 85

3-[(3R)-3-({5-Fluoro-6-[6-(hydroxymethyl)pyridin-3-yl]-2-pyrazolo[1,5-a]pyridin-3-ylpyrimidin-4-yl}amino)piperidin-1-yl]-3-oxopropanenitrile Obtained as a pale solid (23%) from (5-{5-fluoro-6-[(3R)-piperidin-3-ylamino]-2-pyrazolo[1,5-a]pyridin-3-ylpyrimidin-4-yl}pyridin-2-yl)methanol (Example 84b, 0.023 g, 0.06 mmol) following the experimental procedure as described in Preparation 6b. The crude was purified by flash chromatography (dichloromethane to 90:10 dichloromethane/methanol).

LRMS (m/z): 487 (M+1)$^+$.

$^1$H-NMR (400 MHz, CDCl$_3$): δ 2.13-2.40 (m, 2H), 3.08-4.97 (m, 9H), 6.77-7.02 (m, 1H), 7.31-7.43 (m, 1H), 7.43-7.58 (m, 1H), 8.34-8.83 (m, 3H), 9.25 (d, 1H).

Example 86

2-((3R)-3-{[6-(2,6-Dimethylpyridin-4-yl)-5-fluoro-2-pyrazolo[1,5-a]pyridin-3-ylpyrimidin-4-yl]amino}piperidin-1-yl)-2-oxoethanol Obtained from 2-{(3R)-3-[(6-chloro-5-fluoro-2-pyrazolo[1,5-a]pyridin-3-ylpyrimidin-4-yl)amino]piperidin-1-yl}-2-oxoethanol (Preparation 7, 0.098 g, 0.24 mmol) and 2,6-dimethyl-4-(4,4,5,5-tetramethyl-1,3,2-dioxaborolan-2-yl)pyridine (prepared as described in Example 37b from 4-bromo-2,6-dimethylpyridine) following the experimental procedure as described in Example 20a. The crude product was purified first by flash chromatography (dichloromethane to dichloromethane/methanol 98:2) and then by reverse phase chromatography (C-18 silica from Waters®, water/1:1 acetonitrile-methanol as eluents [0.1% v/v ammonium formate buffered] 0% to 100%) to yield the title compound (0.014 g, 12%) as a white solid.

LRMS (m/z): 476 (M+1)$^+$.

$^1$H-NMR (400 MHz, CDCl$_3$): δ 1.76-2.32 (m, 4H), 2.65 (s, 6H), 2.96-5.39 (m, 9H), 6.76-6.99 (m, 1H), 7.35 (q, 1H), 7.64 (d, 2H), 8.41-8.61 (m, 2H), 8.70 (m, 1H).

Example 87

3-((3R)-3-{[6-(2,6-Dimethylpyridin-4-yl)-5-fluoro-2-pyrazolo[1,5-a]pyridin-3-ylpyrimidin-4-yl]amino}piperidin-1-yl)-3-oxopropanenitrile a) Tert-butyl (3R)-3-{[6-(2,6-dimethylpyridin-4-yl)-5-fluoro-2-pyrazolo[1,5-a]pyridin-3-ylpyrimidin-4-yl]amino}piperidine-1-carboxylate Obtained from tert-butyl (3R)-3-[(6-chloro-5-fluoro-2-pyrazolo[1,5-a]pyridin-3-ylpyrimidin-4-yl) amino]piperidine-1-carboxylate (Preparation 5, 0.300 g, 0.67 mmol) and 2,6-dimethyl-4-(4,4,5,5-tetramethyl-1,3,2-dioxaborolan-2-yl)pyridine (prepared as described in Example 37b from 4-bromo-2,6-dimethylpyridine) following the experimental procedure as described in Example 20a. The crude product was purified by reverse phase chromatography (C-18 silica from Waters®, water/1:1 acetonitrile-methanol as eluents 0% to 100%) to yield the title compound (0.149 g, 43%) as a white solid.

LRMS (m/z): 519 (M+1)$^+$.

b) 6-(2,6-Dimethylpyridin-4-yl)-5-fluoro-N-[(3R)-piperidin-3-yl]-2-pyrazolo[1,5-a]pyridin-3-ylpyrimidin-4-amine To a solution of tert-butyl (3R)-3-{[6-(2,6-dimethylpyridin-4-yl)-5-fluoro-2-pyrazolo[1,5-a]pyridin-3-ylpyrimidin-4-yl]amino}piperidine-1-carboxylate (Example 87a, 0.149 g, 0.29 mmol) in dioxane (2 mL) was added a 4 M solution of hydrochloric acid in dioxane (1.5 mL). The reaction mixture was stirred at room temperature for 1 hour and then the volatiles were removed under reduced pressure to give 0.141 g (100% yield) of the title compound as a dichlorohydrate salt.

LRMS (m/z): 418 (M+1)$^+$.

c) 3-((3R)-3-{[6-(2,6-Dimethylpyridin-4-yl)-5-fluoro-2-pyrazolo[1,5-a]pyridin-3-ylpyrimidin-4-yl]amino}piperidin-1-yl)-3-oxopropanenitrile Obtained as a light yellow solid (77%) from 6-(2,6-Dimethylpyridin-4-yl)-5-fluoro-N-[(3R)-piperidin-3-yl]-2-pyrazolo[1,5-a]pyridin-3-ylpyrimidin-4-amine (Example 87b) following the experimental procedure as described in Preparation 6b. The crude product was purified by flash chromatography (dichloromethane to dichloromethane/methanol 90:10).

LRMS (m/z): 485 (M+1)$^+$.

$^1$H-NMR (400 MHz, CDCl$_3$): δ 1.74-2.33 (m, 4H), 2.67 (s, 6H), 2.99-5.28 (m, 8H), 6.80-7.03 (m, 1H), 7.31-7.47 (m, 1H), 7.58-7.76 (m, 2H), 8.39-8.60 (m, 2H), 8.60-8.78 (m, 1H).

Example 88

2-[(3R)-3-({5-Fluoro-6-[5-(hydroxymethyl)pyridin-3-yl]-2-pyrazolo[1,5-a]pyridin-3-ylpyrimidin-4-yl}amino)piperidin-1-yl]-2-oxoethanol a) Tert-butyl (3R)-3-[(5-fluoro-2-pyrazolo[1,5-a]pyridin-3-yl-6-{5-[(tetrahydro-2H-pyran-2-yloxy)methyl]pyridin-3-yl}pyrimidin-4-yl)amino]piperidine-1-carboxylate Obtained from tert-butyl (3R)-3-[(6-chloro-5-fluoro-2-pyrazolo[1,5-a]pyridin-3-ylpyrimidin-4-yl) amino]piperidine-1-carboxylate (Preparation 5, 0.335 g, 0.56 mmol) and 3-[(tetrahydro-2H-pyran-2-yloxy)methyl]-5-(4,4,5,5-tetramethyl-1,3,2-dioxaborolan-2-yl)pyridine (prepared as described in Example 37a and 37b from (5-bromopyridin-3-yl)methanol) following the experimental procedure as described in Example 20a. The crude product was purified by flash chromatography (hexane to hexane/ethyl acetate 20:80) to yield the title compound (0.335 g, 99%) as a white solid.

LRMS (m/z): 605 (M+1)$^+$.

b) (5-{5-Fluoro-6-[(3R)-piperidin-3-ylamino]-2-pyrazolo[1,5-a]pyridin-3-ylpyrimidin-4-yl}pyridin-3-yl)methanol To a solution of tert-butyl (3R)-3-[(5-fluoro-2-pyrazolo[1,5-a]pyridin-3-yl-6-{5-[(tetrahydro-2H-pyran-2-yloxy)methyl]pyridin-3-yl}pyrimidin-4-yl)amino]piperidine-1-carboxylate (Example 88a, 0.335 g, 0.56 mmol) in tetrahydrofuran (2 mL), 1N hydrochloric acid (1.70 mL) was added. The reaction mixture was stirred at room temperature for 1 hour and then at 60° C. for 3 hours, then water (15 mL) and a 2M solution of sodium hydroxide (1 mL) were added. The product was extracted with dichloromethane (×3), the combined organic layers were washed with brine, dried over magnesium sulfate and the solvent was evaporated to dryness to yield the title compound (0.209 g, 90%) as a pale solid.

LRMS (m/z): 420 (M+1)$^+$.

c) 2-[(3R)-3-({5-Fluoro-6-[5-(hydroxymethyl)pyridin-3-yl]-2-pyrazolo[1,5-a]pyridin-3-ylpyrimidin-4-yl}amino)piperidin-1-yl]-2-oxoethanol Prepared from (5-{5-Fluoro-6-[(3R)-piperidin-3-ylamino]-2-pyrazolo[1,5-a]pyridin-3-ylpyrimidin-4-yl}pyridin-3-yl)methanol (Example 88b, 0.104 g, 0.25 mmol) following the experimental procedure as described in Example 67c. The crude product was treated with a mixture of methanol (15 mL), water (15 mL) and a few drops of a 2 M solution of sodium hydroxide for 1 hour and then purified by flash chromatography (dichloromethane to 85:15 dichloromethane/methanol) to yield the title compound (0.041 g, 35%) as a white solid.

LRMS (m/z): 478 (M+1)$^+$.

$^1$H-NMR (400 MHz, CDCl$_3$): δ 1.58-2.32 (m, 5H), 3.04-4.43 (m, 7H), 4.55-4.70 (m, 1H), 4.79 (s, 2H), 6.77-6.97 (m, 1H), 7.27-7.39 (m, 1H), 8.38-8.53 (m, 2H), 8.53-8.73 (m, 3H), 9.17 (s, 1H).

Example 89

3-[(3R)-3-({5-Fluoro-6-[5-(hydroxymethyl)pyridin-3-yl]-2-pyrazolo[1,5-a]pyridin-3-ylpyrimidin-4-yl}amino)piperidin-1-yl]-3-oxopropanenitrile Obtained as a light yellow solid (51%) from (5-{5-fluoro-6-[(3R)-piperidin-3-ylamino]-2-pyrazolo[1,5-a]pyridin-3-ylpyrimidin-4-yl}pyridin-3-yl)methanol (Example 88b) following the experimental procedure as described in Preparation 6b. The crude product was purified by flash chromatography (dichloromethane to dichloromethane/methanol 90:10).

LRMS (m/z): 487 (M+1)$^+$.

$^1$H-NMR (400 MHz, CDCl$_3$): δ 1.61-2.29 (m, 4H), 2.99-4.18 (m, 6H), 4.17-4.36 (m, 1H), 4.46-4.63 (m, 1H), 4.80 (s, 2H), 6.79-6.97 (m, 1H), 7.30-7.44 (m, 1H), 8.28-8.54 (m, 2H), 8.54-8.76 (m, 2H), 9.06-9.28 (m, 1H).

Example 90

(2S)-1-[(5-Fluoro-6-{[(3R)-1-glycoloylpiperidin-3-yl]oxy}-2-pyrazolo[1,5-a]pyridin-3-ylpyrimidin-4-yl)oxy]propan-2-ol a) Tert-butyl (3R)-3-[(5-fluoro-6-{[(2S)-2-hydroxypropyl]oxy}-2-pyrazolo[1,5-a]pyridin-3-ylpyrimidin-4-yl)oxy]piperidine-1-carboxylate Obtained as a (1.8:1) mixture of the title compound and tert-butyl (3R)-3-({5-fluoro-6-[(1S)-2-hydroxy-1-methylethoxy]-2-pyrazolo[1,5-a]pyridin-3-ylpyrimidin-4-yl}oxy)piperidine-1-carboxylate from tert-butyl (3R)-3-[(6-chloro-5-fluoro-2-pyrazolo[1,5-a]pyridin-3-ylpyrimidin-4-yl)amino]piperidine-1-carboxylate (Preparation 5) and (2S)-1-methoxypropan-2-ol following the experimental procedure described in Example 15a.

LRMS (m/z): 488 (M+1)$^+$.

b) (2S)-1-({5-Fluoro-6-[(3R)-piperidin-3-yloxy]-2-pyrazolo[1,5-a]pyridin-3-ylpyrimidin-4-yl}oxy)propan-2-ol Obtained as a (2:1) mixture of the title compound and (2S)-2-({5-fluoro-6-[(3R)-piperidin-3-yloxy]-2-pyrazolo[1,5-a]pyridin-3-ylpyrimidin-4-yl}oxy)propan-1-ol (71%) from the mixture obtained in Example 90a, following the experimental procedure described in Example 20a.

LRMS (m/z): 388 (M+1)$^+$.

c) (2S)-1-[(5-Fluoro-6-{[(3R)-1-glycoloylpiperidin-3-yl]oxy}-2-pyrazolo[1,5-a]pyridin-3-ylpyrimidin-4-yl)oxy]propan-2-ol Obtained as a white solid (16%) from the mixture obtained in Example 90b, following the experimental procedure described in Preparation 7 followed by purification by reverse phase chromatography (C-18 silica from Waters®, water/methanol as eluents 0% to 100%).

LRMS (m/z): 445 (M+1)$^+$.

$^1$H NMR (400 MHz, CDCl$_3$): δ 1.29-1.39 (m, 3H), 1.66-1.96 (m, 3H), 2.13-2.25 (m, 1H), 2.98-3.79 (m, 5H), 3.93-4.81 (m, 7H), 6.82-6.94 (m, 1H), 7.28-7.39 (m, 1H), 8.32-8.47 (m, 1H), 8.61 (s, 2H).

Example 91

5-[(3R)-3-({5-Fluoro-6-[(1R)-2-methoxy-1-methylethoxy]-2-pyrazolo[1,5-a]pyridin-3-ylpyrimidin-4-yl}amino)piperidin-1-yl]pyrazine-2-carbonitrile Obtained as a pale yellow solid (47%) from 5-fluoro-6-[(1R)-2-methoxy-1-methylethoxy]-N-[(3R)-piperidin-3-yl]-2-pyrazolo[1,5-a]pyridin-3-ylpyrimidin-4-amine (Example 60b) following the experimental procedure described in Example 54 followed by purification by flash chromatography (gradient from hexane to ethyl acetate).

LRMS (m/z): 504 (M+1)$^+$.

$^1$H NMR (300 MHz, DMSO-d6): δ 1.31-1.39 (m, 3H), 1.54-2.16 (m, 5H), 2.91-3.21 (m, 3H), 3.48-3.73 (m, 2H), 4.74 (s, 5H), 5.54 (td, 1H), 6.94-7.07 (m, 1H), 7.20-7.37 (m, 2H), 8.23-8.35 (m, 1H), 8.39-8.49 (m, 1H), 8.56 (s, 1H), 8.75-8.83 (m, 1H).

Example 92

Isopropyl 5-fluoro-6-{[(3R)-1-glycoloylpiperidin-3-yl]amino}-2-pyrazolo[1,5-a]pyridin-3-ylpyrimidine-4-carboxylate a) Isopropyl 6-{[(3R)-1-(tert-butoxycarbonyl)piperidin-3-yl]amino}-5-fluoro-2-pyrazolo[1,5-a]pyridin-3-ylpyrimidine-4-carboxylate A mixture of 6-{[(3R)-1-(tert-butoxycarbonyl)piperidin-3-yl]amino}-5-fluoro-2-pyrazolo[1,5-a]pyridin-3-ylpyrimidine-4-carboxylic acid (Example 46b, 0.093 g, 0.18 mmol), cesium carbonate (0.115 g, 0.35 mmol) and 2-iodopropane (0.027 mL, 1.50 mmol) in N,N-dimethylformamide (2.5 mL) was stirred at 60° C. for 1 hour. Then the reaction mixture was partitioned between water and ethyl acetate and the organic layer was washed with brine, dried over magnesium sulfate, filtered and the solvents were evaporated in vacuo. The product was purified by flash chromatography (dichloromethane to dichloromethane/methanol 95:5) to give the title compound (0.085 g, 90%) as an oil.

LRMS (m/z): 499 (M+1)$^+$.

b) Isopropyl 5-fluoro-6-[(3R)-piperidin-3-ylamino]-2-pyrazolo[1,5-a]pyridin-3-ylpyrimidine-4-carboxylate To a solution of isopropyl 6-{[(3R)-1-(tert-butoxycarbonyl)piperidin-3-yl]amino}-5-fluoro-2-pyrazolo[1,5-a]pyridin-3-ylpyrimidine-4-carboxylate (Example 92a, 0.085 g, 0.17 mmol) in dichloromethane (3 mL), trifluoroacetic acid (0.302 mL) was added. The mixture was stirred at room temperature for 30 minutes, the volatiles were removed in vacuo and the residue was redissolved in water. The pH was adjusted to 9 with a saturated sodium bicarbonate solution and the product was extracted with dichloromethane (×3). The combined organic layer was washed with brine, dried over magnesium sulfate, filtered and the solvents were evaporated in vacuo to give the title compound (0.068 g, 100%) as an oil.

LRMS (m/z): 399 (M+1)$^+$.

c) Isopropyl 5-fluoro-6-{[(3R)-1-glycoloylpiperidin-3-yl]amino}-2-pyrazolo[1,5-a]pyridin-3-ylpyrimidine-4-carboxylate Prepared from isopropyl 5-fluoro-6-[(3R)-piperidin-3-ylamino]-2-pyrazolo[1,5-a]pyridin-3-ylpyrimidine-4-carboxylate (Example 92b, 0.068 g, 0.17 mmol) following the experimental procedure as described in Example 67c. The crude product was purified by flash chromatography (dichloromethane to 95:5 dichloromethane/methanol) to yield the title compound (0.015 g, 19%) as a pale yellow solid.

LRMS (m/z): 457 (M+1)$^+$.

$^1$H-NMR (400 MHz, CDCl$_3$): δ 1.37-1.47 (m, 6H), 1.69-2.27 (m, 4H), 3.09-4.67 (m, 8H), 5.19 (s, 1H), 5.28-5.45 (m, 1H), 6.82-6.92 (m, 1H), 7.29-7.41 (m, 1H), 8.46-8.55 (m, 1H), 8.55-8.78 (m, 2H).

Example 93

2-{(3R)-3-[(6-Methoxy-5-methyl-2-pyrazolo[1,5-a]pyridin-3-ylpyrimidin-4-yl)amino]piperidin-1-yl}-2-oxoethanol a) Tert-butyl (3R)-3-[(6-methoxy-5-methyl-2-pyrazolo[1,5-a]pyridin-3-ylpyrimidin-4-yl)amino]piperidine-1-carboxylate Obtained as an oil (31%) from (R)-tert-butyl 3-((6-chloro-5-methyl-2-(pyrazolo[1,5-a]pyridin-3-yl)pyrimidin-4-yl)amino)piperidine-1-carboxylate (Preparation 8c) following the experimental procedure described in Example 42c.

LRMS (m/z): 439 (M+1)$^+$.

b) 6-Methoxy-5-methyl-N-[(3R)-piperidin-3-yl]-2-pyrazolo[1,5-a]pyridin-3-ylpyrimidin-4-amine Obtained as a solid dihydrochloride salt (99%) from tert-butyl (3R)-3-[(6-methoxy-5-methyl-2-pyrazolo[1,5-a]pyridin-3-ylpyrimidin-4-yl)amino]piperidine-1-carboxylate (Example 93a) following the experimental procedure described in Example 14b.

LRMS (m/z): 339 (M+1)$^+$.

c) 2-{(3R)-3-[(6-Methoxy-5-methyl-2-pyrazolo[1,5-a]pyridin-3-ylpyrimidin-4-yl)amino]piperidin-1-yl}-2-oxoethanol Obtained as a white solid (41%) from 6-methoxy-5-methyl-N-[(3R)-piperidin-3-yl]-2-pyrazolo[1,5-a]pyridin-3-ylpyrimidin-4-amine (Example 93b) following the experimental procedure described in Example 67c followed by purification by reverse phase chromatography (C-18 silica from Waters®, water/methanol as eluents 0% to 100%).

LRMS (m/z): 396 (M+1)$^+$.

$^1$H NMR (400 MHz, CDCl$_3$): δ 1.59-1.86 (m, 6H), 2.06-2.15 (m, 1H), 3.02-3.93 (m, 6H), 4.01 (d, 3H), 4.09-4.35 (m, 3H), 6.75-6.86 (m, 1H), 7.21 (s, 1H), 8.39-8.72 (m, 3H).

Example 94

2-{(3R)-3-[(6-Methoxy-2-pyrazolo[1,5-a]pyridin-3-ylpyrimidin-4-yl)amino]piperidin-1-yl}-2-oxoethanol a) Tert-butyl (3R)-3-[(6-methoxy-2-pyrazolo[1,5-a]pyridin-3-ylpyrimidin-4-yl)amino]piperidine-1-carboxylate Obtained as a white solid (74%) from tert-butyl (3R)-3-[(6-chloro-2-pyrazolo[1,5-a]pyridin-3-ylpyrimidin-4-yl)amino]piperidine-1-carboxylate (Preparation 10c, 0.300 g, 0.70 mmol) following the experimental procedure as described in Example 42a. Excess solution of sodium methoxide in methanol was added until the reaction was completed.

LRMS (m/z): 425 (M+1)$^+$.

b) 6-Methoxy-N-[(3R)-piperidin-3-yl]-2-pyrazolo[1,5-a]pyridin-3-ylpyrimidin-4-amine Obtained as a pale white solid (80%) from tert-butyl (3R)-3-[(6-methoxy-2-pyrazolo[1,5-a]pyridin-3-ylpyrimidin-4-yl)amino]piperidine-1-carboxylate (Example 94a) following the experimental procedure as described in Example 20b.

LRMS (m/z): 343 (M+1)⁺.

c) 2-{(3R)-3-[(6-Methoxy-2-pyrazolo[1,5-a]pyridin-3-ylpyrimidin-4-yl)amino]piperidin-1-yl}-2-oxoethanol Obtained as a white solid (80%) from 6-methoxy-N-[(3R)-piperidin-3-yl]-2-pyrazolo[1,5-a]pyridin-3-ylpyrimidin-4-amine (Example 94b) following the experimental procedure as described in Preparation 7. The crude was purified by flash chromatography (gradient from dichloromethane to dichloromethane/methanol 91:9).

LRMS (m/z): 383 (M+1)⁺.

¹H-NMR (400 MHz, CDCl₃): δ 1.65-2.23 (m, 4H), 3.01-3.18 (m, 1H), 3.31-3.92 (m, 4H), 3.92-4.10 (m, 3H), 4.10-4.93 (m, 3H), 5.43-5.64 (m, 1H), 6.77-6.94 (m, 1H), 7.28-7.42 (m, 1H), 8.39-8.60 (m, 2H), 8.60-8.78 (m, 1H).

Example 95

3-{(3R)-3-[(6-Methoxy-2-pyrazolo[1,5-a]pyridin-3-ylpyrimidin-4-yl)amino]piperidin-1-yl}-3-oxopropanenitrile Obtained as a white solid (93%) from 6-methoxy-N-[(3R)-piperidin-3-yl]-2-pyrazolo[1,5-a]pyridin-3-ylpyrimidin-4-amine (Example 94b) following the experimental procedure as described in Preparation 6b. The crude was purified by flash chromatography (gradient from dichloromethane to dichloromethane/methanol 80:20).

LRMS (m/z): 383 (M+1)⁺.

¹H-NMR (400 MHz, CDCl₃): δ 1.66-2.25 (m, 4H), 3.23-3.91 (m, 5H), 3.93-4.15 (m, 3H), 4.18-4.86 (m, 2H), 5.57 (d, 1H), 6.88 (dt, 1H), 7.28-7.42 (m, 1H), 8.46-8.59 (m, 2H), 8.59-8.75 (m, 1H).

Example 96

2-((3R)-3-{[6-(2-Methoxyethoxy)-2-pyrazolo[1,5-a]pyridin-3-ylpyrimidin-4-yl]amino}piperidin-1-yl)-2-oxoethanol a) Tert-butyl (3R)-3-{[6-(2-methoxyethoxy)-2-pyrazolo[1,5-a]pyridin-3-ylpyrimidin-4-yl]amino}piperidine-1-carboxylate A solution of 2-methoxyethanol (0.55 mL, 7.0 mmol) and potassium tert-butanol (0.236 g, 2.1 mmol) in dioxane (3 mL) was stirred at room temperature for 30 minutes. Then tert-butyl (3R)-3-[(6-chloro-2-pyrazolo[1,5-a]pyridin-3-ylpyrimidin-4-yl)amino]piperidine-1-carboxylate (Preparation 10c, 0.300 g, 0.70 mmol) was added and the reaction mixture was stirred under reflux overnight. The reaction mixture was cooled to room temperature and partitioned between water and ethyl acetate. The organic layer was separated and the aqueous layer was extracted with ethyl acetate. The combined organic layers were washed with brine, dried over magnesium sulfate and concentrated in vacuo. The resulting crude was purified by flash chromatography (gradient from dichloromethane to dichloromethane/methanol 95:5) to yield the title compound (0.188 g, 57%) as a solid.

LRMS (m/z): 469 (M+1)⁺.

b) 6-(2-Methoxyethoxy)-N-[(3R)-piperidin-3-yl]-2-pyrazolo[1,5-a]pyridin-3-ylpyrimidin-4-amine Obtained as a pale white solid (86%) from tert-butyl (3R)-3-{[6-(2-methoxyethoxy)-2-pyrazolo[1,5-a]pyridin-3-ylpyrimidin-4-yl]amino}piperidine-1-carboxylate (Example 96a) following the experimental procedure as described in Example 20b.

LRMS (m/z): 369 (M+1)⁺.

c) 2-((3R)-3-{[6-(2-Methoxyethoxy)-2-pyrazolo[1,5-a]pyridin-3-ylpyrimidin-4-yl]amino}piperidin-1-yl)-2-oxoethanol Obtained as a white solid (20%) from 6-(2-methoxyethoxy)-N-[(3R)-piperidin-3-yl]-2-pyrazolo[1,5-a]pyridin-3-ylpyrimidin-4-amine (Example 96b) following the experimental procedure as described in Preparation 6b. The crude was purified first by reverse phase chromatography (C-18 silica from Waters®, water/1:1 acetonitrile-methanol as eluents 0% to 100%), then by flash chromatography (dichloromethane to dichloromethane/methanol 85:15) and finally by preparative HPLC (gradient from water to methanol).

LRMS (m/z): 427 (M+1)⁺.

¹H-NMR (400 MHz, CDCl₃): δ 1.63-2.25 (m, 4H), 3.01-3.25 (m, 2H), 3.25-4.30 (m, 9H), 4.37-4.81 (m, 3H), 5.47-5.70 (m, 1H), 6.79-6.96 (m, 1H), 7.27-7.37 (m, 1H), 8.40-8.57 (m, 2H), 8.57-8.71 (m, 1H).

Example 97

3-((3R)-3-{[6-(2-Methoxyethoxy)-2-pyrazolo[1,5-a]pyridin-3-ylpyrimidin-4-yl]amino}piperidin-1-yl)-3-oxopropanenitrile Obtained as a white solid (25%) from 6-(2-methoxyethoxy)-N-[(3R)-piperidin-3-yl]-2-pyrazolo[1,5-a]pyridin-3-ylpyrimidin-4-amine (Example 96b) following the experimental procedure as described in Preparation 6b. The crude was purified first by flash chromatography (dichloromethane to dichloromethane/methanol 85:15), then by reverse phase chromatography (C-18 silica from Waters®, water/1:1 acetonitrile-methanol as eluents 0% to 100%) and finally by preparative HPLC (gradient from water to methanol).

LRMS (m/z): 436 (M+1)⁺.

¹H-NMR (400 MHz, CDCl₃): δ 1.64-2.25 (m, 4H), 2.87-4.17 (m, 11H), 4.34-4.81 (m, 3H), 5.53-5.67 (m, 1H), 7.28-7.40 (m, 1H), 8.41-8.58 (m, 2H), 8.58-8.70 (m, 1H)

Example 98

2-((3R)-3-{[6-(2-Methoxypyridin-4-yl)-2-pyrazolo[1,5-a]pyridin-3-ylpyrimidin-4-yl]amino}piperidin-1-yl)-2-oxoethanol a) Tert-butyl (3R)-3-{[6-(2-methoxypyridin-4-yl)-2-pyrazolo[1,5-a]pyridin-3-ylpyrimidin-4-yl]amino}piperidine-1-carboxylate Obtained from tert-butyl (3R)-3-[(6-chloro-2-pyrazolo[1,5-a]pyridin-3-ylpyrimidin-4-yl)amino]piperidine-1-carboxylate (Preparation 10c, 0.300 g, 0.70 mmol) following the experimental procedure as described in Example 20a. The crude product was purified by reverse phase chromatography (C-18 silica from Waters®, water/1:1 acetonitrile-methanol as eluents 0% to 100%) to yield the title compound (0.153 g, 38%) as a white solid.

LRMS (m/z): 502 (M+1)+.

b) 6-(2-Methoxypyridin-4-yl)-N-[(3R)-piperidin-3-yl]-2-pyrazolo[1,5-a]pyridin-3-ylpyrimidin-4-amine Obtained as a pale white solid (57%) from tert-butyl (3R)-3-{[6-(2-methoxypyridin-4-yl)-2-pyrazolo[1,5-a]pyridin-3-ylpyrimidin-4-yl]amino}piperidine-1-carboxylate (Example 98a) following the experimental procedure as described in Example 20b.

LRMS (m/z): 402 (M+1)+.

c) 2-((3R)-3-{[6-(2-Methoxypyridin-4-yl)-2-pyrazolo[1,5-a]pyridin-3-ylpyrimidin-4-yl]amino}piperidin-1-yl)-2-oxoethanol Obtained as a white solid (29%) from 6-(2-methoxypyridin-4-yl)-N-[(3R)-piperidin-3-yl]-2-pyrazolo[1,5-a]pyridin-3-ylpyrimidin-4-amine (Example 98b) following the experimental procedure as described in Preparation 7. The crude was purified first by flash chromatography (gradient from dichloromethane to dichloromethane/methanol 91:9), then by reverse phase chromatography (C-18 silica from Waters®, water/1:1 acetonitrile-methanol as eluents 0% to 100%) and finally by preparative HPLC (gradient from water to methanol).

LRMS (m/z): 460 (M+1)+.
1H-NMR (400 MHz, CDCl3): δ 1.65-2.32 (m, 4H), 3.08-3.90 (m, 5H), 4.02 (s, 3H), 4.09-5.03 (m, 3H), 6.57 (m, 1H), 6.90 (m, 1H), 7.31-7.48 (m, 2H), 7.53 (m, 1H), 8.31 (d, 1H), 8.54 (t, 1H), 8.63 (dd, 1H), 8.75 (m, 1H).

Example 99

2-((3R)-3-{[6-(6-Methylpyridin-3-yl)-2-pyrazolo[1,5-a]pyridin-3-ylpyrimidin-4-yl]amino}piperidin-1-yl)-2-oxoethanol a) Tert-butyl (3R)-3-{[6-(6-methylpyridin-3-yl)-2-pyrazolo[1,5-a]pyridin-3-ylpyrimidin-4-yl]amino}piperidine-1-carboxylate Obtained from tert-butyl (3R)-3-[(6-chloro-2-pyrazolo[1,5-a]pyridin-3-ylpyrimidin-4-yl)amino]piperidine-1-carboxylate (Preparation 10c, 0.300 g, 0.70 mmol) following the experimental procedure as described in Example 20a. The crude product was purified first by flash chromatography (gradient from dichloromethane to dichloromethane/methanol 85:15) and then by reverse phase chromatography (C-18 silica from Waters®, water/1:1 acetonitrile-methanol as eluents 0% to 100%) to yield the title compound (0.128 g, 41%) as a white solid.

LRMS (m/z): 486 (M+1)+.

b) 6-(6-Methylpyridin-3-yl)-N-[(3R)-piperidin-3-yl]-2-pyrazolo[1,5-a]pyridin-3-ylpyrimidin-4-amine Obtained from tert-butyl (3R)-3-{[6-(6-methylpyridin-3-yl)-2-pyrazolo[1,5-a]pyridin-3-ylpyrimidin-4-yl]amino}piperidine-1-carboxylate (Example 99a) following the experimental procedure as described in Example 67b to give the title compound (93% yield) as the dichlorohydrate salt.

LRMS (m/z): 386 (M+1)+.

c) 2-((3R)-3-{[6-(6-Methylpyridin-3-yl)-2-pyrazolo[1,5-a]pyridin-3-ylpyrimidin-4-yl]amino}piperidin-1-yl)-2-oxoethanol Prepared from 6-(6-methylpyridin-3-yl)-N-[(3R)-piperidin-3-yl]-2-pyrazolo[1,5-a]pyridin-3-ylpyrimidin-4-amine dichlorohydrate salt (Example 99b, 0.085 g, 0.18 mmol) following the experimental procedure as described in Example 67c. The crude product was purified first by flash chromatography (dichloromethane to 85:15 dichloromethane/methanol) and then by reverse phase chromatography (C-18 silica from Waters®, water/1:1 acetonitrile-methanol as eluents 0% to 100%) to yield the title compound (0.082 g, 50%) as a pale solid.

LRMS (m/z): 444 (M+1)+.
1H-NMR (400 MHz, DMSO-d6): δ 1.38-2.10 (m, 4H), 2.55 (s, 3H), 2.60-3.15 (m, 2H), 3.57-4.80 (m, 4H), 6.67-6.89 (m, 1H), 7.04 (s, 1H), 7.27-7.58 (m, 2H), 8.18-9.30 (m, 4H).

Example 100

3-((3R)-3-{[6-(6-Methylpyridin-3-yl)-2-pyrazolo[1,5-a]pyridin-3-ylpyrimidin-4-yl]amino}piperidin-1-yl)-3-oxopropanenitrile Obtained as a white solid (48%) from 6-(6-methylpyridin-3-yl)-N-[(3R)-piperidin-3-yl]-2-pyrazolo[1,5-a]pyridin-3-ylpyrimidin-4-amine dichlorohydrate salt (Example 99b) following the experimental procedure as described in Preparation 6b. The crude was purified first by flash chromatography (dichloromethane to dichloromethane/methanol 85:15) and then by reverse phase chromatography (C-18 silica from Waters®, water/1:1 acetonitrile-methanol as eluents 0% to 100%).

LRMS (m/z): 453 (M+1)+.
1H-NMR (400 MHz, CDCl3): δ 1.68-2.30 (m, 4H), 2.65 (s, 3H), 3.06-3.93 (m, 5H), 4.03-4.55 (m, 2H), 4.81-5.04 (m, 1H), 6.48-6.69 (m, 1H), 6.80-7.02 (m, 1H), 7.28-7.44 (m, 2H), 8.29 (d, 1H), 8.47-8.82 (m, 3H), 9.23 (s, 1H).

Example 101

2-((3R)-3-{[6-(2,6-Dimethylpyridin-4-yl)-2-pyrazolo[1,5-a]pyridin-3-ylpyrimidin-4-yl]amino}piperidin-1-yl)-2-oxoethanol a) Tert-butyl (3R)-3-{[6-(2,6-dimethylpyridin-4-yl)-2-pyrazolo[1,5-a]pyridin-3-ylpyrimidin-4-yl]amino}piperidine-1-carboxylate Obtained from tert-butyl (3R)-3-[(6-chloro-2-pyrazolo[1,5-a]pyridin-3-ylpyrimidin-4-yl)amino]piperidine-1-carboxylate (Preparation 10c, 0.276 g, 0.64 mmol) following the experimental procedure as described in Example 20a. The crude product was purified by flash chromatography (gradient from dichloromethane to dichloromethane/methanol 85:15) to yield the title compound as a white solid.

LRMS (m/z): 500 (M+1)+.

b) 6-(2,6-Dimethylpyridin-4-yl)-N-[(3R)-piperidin-3-yl]-2-pyrazolo[1,5-a]pyridin-3-ylpyrimidin-4-amine Obtained as a solid dihydrochloride salt (52%) from tert-butyl (3R)-3-{[6-(2,6-dimethylpyridin-4-yl)-2-pyrazolo[1,5-a]pyridin-3-ylpyrimidin-4-yl]amino}piperidine-1-carboxylate (Example 101a) following the experimental procedure described in Example 14b.
LRMS (m/z): 400 (M+1)$^+$.

c) 2-((3R)-3-{[6-(2,6-Dimethylpyridin-4-yl)-2-pyrazolo[1,5-a]pyridin-3-ylpyrimidin-4-yl]amino}piperidin-1-yl)-2-oxoethanol Obtained as a white solid (55%) from 6-(2,6-dimethylpyridin-4-yl)-N-[(3R)-piperidin-3-yl]-2-pyrazolo[1,5-a]pyridin-3-ylpyrimidin-4-amine dihydrochloride salt (Example 101b) following the experimental procedure described in Preparation 7. The crude was purified first by flash chromatography (dichloromethane to dichloromethane/methanol 85:15) and then by reverse phase chromatography (C-18 silica from Waters®, water/1:1 acetonitrile-methanol as eluents 0% to 100%).
LRMS (m/z): 458 (M+1)$^+$.
$^1$H-NMR (400 MHz, CDCl$_3$): δ 1.65-2.29 (m, 4H), 2.65 (s, 6H), 3.01-5.07 (m, 9H), 6.43-6.73 (m, 1H), 6.77-7.06 (m, 1H), 7.31-7.46 (m, 1H), 7.52-7.75 (m, 2H), 8.45-8.86 (m, 3H).

Example 102

3-((3R)-3-{[6-(2,6-Dimethylpyridin-4-yl)-2-pyrazolo[1,5-a]pyridin-3-ylpyrimidin-4-yl]amino}piperidin-1-yl)-3-oxopropanenitrile Obtained as a white solid (54%) from 6-(2,6-dimethylpyridin-4-yl)-N-[(3R)-piperidin-3-yl]-2-pyrazolo[1,5-a]pyridin-3-ylpyrimidin-4-amine dihydrochloride salt (Example 101b) following the experimental procedure as described in Preparation 6b. The crude was purified first by reverse phase chromatography (C-18 silica from Waters®, water/1:1 acetonitrile-methanol as eluents 0% to 100%) and then by flash chromatography (chloroform to chloroform/methanol 95:5).
LRMS (m/z): 467 (M+1)$^+$.
$^1$H-NMR (400 MHz, CDCl$_3$): δ 1.69-2.30 (m, 4H), 2.65 (s, 6H), 3.19-4.53 (m, 7H), 4.76-5.12 (m, 1H), 6.63 (d, 1H), 6.82-7.03 (m, 1H), 7.32-7.49 (m, 1H), 7.56-7.71 (m, 2H), 8.45-8.70 (m, 2H), 8.70-8.85 (m, 1H).

Example 103

3-((3R)-3-{[6-(2-Hydroxyethoxy)-2-pyrazolo[1,5-a]pyridin-3-ylpyrimidin-4-yl]amino}piperidin-1-yl)-3-oxopropanenitrile a) Tert-butyl (3R)-3-{[6-(2-hydroxyethoxy)-2-pyrazolo[1,5-a]pyridin-3-ylpyrimidin-4-yl]amino}piperidine-1-carboxylate To a solution of potassium tert-butoxide (0.523 g, 4.7 mmol) in dioxane (3 mL), ethylene glycol (2 mL) was added and the resulting solution was stirred at room temperature for 30 minutes. Then tert-butyl (3R)-3-[(6-chloro-2-pyrazolo[1,5-a]pyridin-3-ylpyrimidin-4-yl)amino]piperidine-1-carboxylate (Preparation 10c, 0.400 g, 0.93 mmol) was added and the mixture was heated at 85° C. overnight. Excess reagents were added and the mixture was heated at reflux until the starting material was consumed. The reaction mixture was partitioned between water and ethyl acetate and the organic layer was washed with water and brine, dried over magnesium sulfate, filtered and evaporated under reduced pressure. The crude product was purified by reverse phase chromatography (C-18 silica from Waters®, water/1:1 acetonitrile-methanol as eluents 0% to 100%) to yield the title compound (0.324 g, 76%) as a yellowish oil.
LRMS (m/z): 455 (M+1)$^+$.

b) 2-({6-[(3R)-Piperidin-3-ylamino]-2-pyrazolo[1,5-a]pyridin-3-ylpyrimidin-4-yl}oxy)ethanol Obtained as a solid dihydrochloride salt (100%) from tert-butyl (3R)-3-{[6-(2-hydroxyethoxy)-2-pyrazolo[1,5-a]pyridin-3-ylpyrimidin-4-yl]amino}piperidine-1-carboxylate (Example 103a) following the experimental procedure described in Example 14b.
LRMS (m/z): 355 (M+1)$^+$.

c) 3-((3R)-3-{[6-(2-Hydroxyethoxy)-2-pyrazolo[1,5-a]pyridin-3-ylpyrimidin-4-yl]amino}piperidin-1-yl)-3-oxopropanenitrile Obtained as a pale solid (61%) from 2-({6-[(3R)-piperidin-3-ylamino]-2-pyrazolo[1,5-a]pyridin-3-ylpyrimidin-4-yl}oxy)ethanol dihydrochloride salt (Example 103b) following the experimental procedure as described in Preparation 6b. The crude was purified by flash chromatography (dichloromethane to dichloromethane/methanol 85:15).
LRMS (m/z): 422 (M+1)$^+$.
$^1$H-NMR (400 MHz, CDCl$_3$): δ 1.67-2.23 (m, 4H), 2.91-4.18 (m, 10H), 4.36-4.92 (m, 3H), 5.62 (s, 1H), 6.77-6.99 (m, 1H), 7.28-7.44 (m, 1H), 8.41-8.57 (m, 2H), 8.57-8.68 (m, 1H).

Example 104

5-((3R)-3-{[6-(2-Hydroxyethoxy)-2-pyrazolo[1,5-a]pyridin-3-ylpyrimidin-4-yl]amino}piperidin-1-yl)pyrazine-2-carbonitrile A suspension of 2-({6-[(3R)-piperidin-3-ylamino]-2-pyrazolo[1,5-a]pyridin-3-ylpyrimidin-4-yl}oxy)ethanol dihydrochloride salt (Example 103b, 0.292 g, 0.82 mmol), 5-chloropyrazine-2-carbonitrile (0.126 g, 0.91 mmol) and potassium carbonate (0.182 g, 1.32 mmol) in N,N-dimethylformamide (8 mL) was heated at 120° C. for 1 hour under microwave irradiation. The reaction mixture was partitioned between water and ethyl acetate and the organic layer was washed with water and brine, dried over magnesium sulfate, filtered and evaporated under reduced pressure. The crude product was purified first by flash chromatography (100% hexane to 100% ethyl acetate) and then by reverse phase chromatography (C-18 silica from Waters®, water/1:1 acetonitrile-methanol as eluents 0% to 100%) to yield the title compound (0.068 g, 18%) as a solid.
LRMS (m/z): 458 (M+1)$^+$.
$^1$H-NMR (400 MHz, CDCl$_3$): δ 1.65-2.30 (m, 4H), 3.10-3.52 (m, 3H), 3.87-4.15 (m, 4H), 4.44-4.68 (m, 3H), 4.78 (s, 1H), 5.60 (s, 1H), 6.77-6.96 (m, 1H), 7.19-7.25 (m, 1H), 8.11-8.21 (m, 1H), 8.34 (d, 1H), 8.40-8.48 (m, 1H), 8.48-8.56 (m, 1H), 8.64 (s, 1H).

Example 105

5-(6-{[(3R)-1-Glycoloylpiperidin-3-yl]amino}-2-pyrazolo[1,5-a]pyridin-3-ylpyrimidin-4-yl)pyridin-3-ol a) Tert-butyl (3R)-3-{[6-(5-hydroxypyridin-3-yl)-2-pyrazolo[1,5-a]pyridin-3-ylpyrimidin-4-yl]amino}piperidine-1-carboxylate Obtained from tert-butyl (3R)-3-[(6-chloro-2-pyrazolo[1,5-a]pyridin-3-ylpyrimidin-4-yl)amino]piperidine-1-carboxylate (Preparation 10c, 0.400 g, 0.93 mmol) following the experimental procedure as described in Example 20a. The crude product was used without further purification in the next step.

LRMS (m/z): 488 (M+1)$^+$.

b) 5-{6-[(3R)-Piperidin-3-ylamino]-2-pyrazolo[1,5-a]pyridin-3-ylpyrimidin-4-yl}pyridin-3-ol Obtained as a solid dihydrochloride salt from tert-butyl (3R)-3-{[6-(5-hydroxypyridin-3-yl)-2-pyrazolo[1,5-a]pyridin-3-ylpyrimidin-4-yl]amino}piperidine-1-carboxylate (crude product obtained in Example 105a) following the experimental procedure described in Example 14b.

LRMS (m/z): 388 (M+1)$^+$.

c) 5-(6-{[(3R)-1-Glycoloylpiperidin-3-yl]amino}-2-pyrazolo[1,5-a]pyridin-3-ylpyrimidin-4-yl)pyridin-3-ol Obtained as a white solid (0.031 g, 27%) from 5-{6-[(3R)-piperidin-3-ylamino]-2-pyrazolo[1,5-a]pyridin-3-ylpyrimidin-4-yl}pyridin-3-ol dihydrochloride salt (Example 105b) following the experimental procedure described in Preparation 7. The crude was purified first by reverse phase chromatography (C-18 silica from Waters®, water/1:1 acetonitrile-methanol as eluents 0% to 100%) and then by preparative HPLC (gradient from water to methanol).

LRMS (m/z): 446 (M+1)$^+$.

$^1$H-NMR (400 MHz, DMSO-d6) δ 1.45-2.15 (m, 4H), 2.60-3.21 (m, 3H), 3.49-4.81 (m, 6H), 6.76 (s, 1H), 7.04 (s, 1H), 7.33-7.62 (m, 2H), 7.82 (s, 1H), 8.14-8.35 (m, 1H), 8.49-8.94 (m, 3H), 10.19 (s, 1H).

Example 106

3-((3R)-3-{[6-(5-Hydroxypyridin-3-yl)-2-pyrazolo[1,5-a]pyridin-3-ylpyrimidin-4-yl]amino}piperidin-1-yl)-3-oxopropanenitrile Obtained as a pale solid (0.030 g, 26%) from 5-{6-[(3R)-piperidin-3-ylamino]-2-pyrazolo[1,5-a]pyridin-3-ylpyrimidin-4-yl}pyridin-3-ol dihydrochloride salt (Example 105b) following the experimental procedure as described in Preparation 6b. The crude was purified by preparative HPLC (gradient from water to methanol).

LRMS (m/z): 455 (M+1)$^+$.

$^1$H-NMR (400 MHz, DMSO-d6) δ 1.38-1.83 (m, 4H), 2.59-3.19 (m, 5H), 3.45-4.43 (m, 4H), 6.66-6.94 (m, 1H), 6.95-7.19 (m, 1H), 7.31-7.68 (m, 2H), 7.82 (s, 1H), 8.23 (s, 1H), 8.45-8.94 (m, 3H), 10.19 (s, 1H).

Example 107

2-{(3R)-3-[(5-Fluoro-6-morpholin-4-yl-2-pyrazolo[1,5-a]pyridin-3-ylpyrimidin-4-yl)(methyl)amino]piperidin-1-yl}-2-oxoethanol Pharmacological Activity In Vitro JAK kinase Assays Compounds were screened for their ability to inhibit JAK1, JAK2 and JAK3 using the assays as indicated below.

The catalytic domains of human JAK1 (aa 850-1154), JAK2 (aa 826-1132), JAK3 (aa 795-1124) and Tyk2 (aa 871-1187) were expressed as N-terminal GST-fusion proteins using a baculovirus expression system and were purchased from Carna Biosciences. The enzymatic activity was assayed using as substrate a biotinylated peptide, poly (GT)-Biotin (CisBio). The peptide concentration in the reactions was 60 nM for JAK1, 20 nM for JAK2, 140 nM for JAK3 and 50 nM for Tyk2. The degree of phosphorylation was detected by TR-FRET (time-resolved fluorescence energy transfer).

IC$_{50}$s of compounds were measured for each kinase in a reaction mixture containing the enzyme, ATP and the peptide in 8 mM MOPS (pH 7.0), 10 mM MgCl$_2$, 0.05% β-mercaptoethanol, 0.45 mg/ml BSA. The ATP concentration in the reactions was 3 μM for JAK1, 0.2 μM for JAK2, 0.6 μM for JAK3 and 1.8 μM for Tyk2. The enzymatic reactions took place for 30 minutes at room temperature. Then, the reactions were stopped with 20 μL of quench detection buffer (50 mM HEPES, 0.5 M KF, EDTA 0.25 M, 0.1% (w/v) BSA, pH 7.5) containing 0.115 μg/mL of anti-phosphoTyr (PT66)-Cryptate (CisBio) and a variable concentration of SA-XL665 (CisBio) to keep the SA-B ratio constant. Incubate for 3 h and read on Victor 2V spectrofluorometer (Perkin Elmer) set to read fluorescence resonance energy transfer.

Some of the acronyms used above have the following meaning:

AA: aminoacids
GST: glutathione-S-transferase
MOPS: 3-(N-morpholino)propane sulfonic acid
BSA: bovine serum albumin
ATP: adenosine tri-phosphate
EDTA: ethylenediaminetetraacetic acid
HEPES: 4-(2-hydroxyethyl)-1-piperazineethanesulfonic acid
SA-XL665: Streptavidin (biotin-binding tetrameric protein isolated from *Streptomyces avidinii*) XL665

Table 1 depicts IC$_{50}$ values for certain exemplary compounds described in the invention.

TABLE 1

| Example No. | IC$_{50}$ JAK3 (nM) | IC$_{50}$ JAK2 (nM) | IC$_{50}$ JAK1 (nM) |
|---|---|---|---|
| 1 | 3 | 0.5 | 12 |
| 2 | 4 | 1 | 82 |
| 3 | 4 | 0.8 | 150 |
| 4 | 4 | 1 | 220 |
| 5 | 2 | 0.5 | 9 |
| 6 | 3 | 0.7 | 15 |
| 7 | 2 | 0.5 | 10 |
| 8 | 10 | 0.7 | 16 |
| 9 | 3 | 0.7 | 85 |

TABLE 1-continued

| Example No. | IC$_{50}$ JAK3 (nM) | IC$_{50}$ JAK2 (nM) | IC$_{50}$ JAK1 (nM) |
|---|---|---|---|
| 10 | 0.7 | 0.5 | 32 |
| 11 | 3 | 1 | 40 |
| 12 | 4 | 0.5 | 4 |
| 13 | 4 | 1 | 4 |
| 14 | 1 | 0.5 | 1 |
| 15 | 2 | 1 | 13 |
| 16 | 1 | 0.7 | 4 |
| 17 | 1 | 0.6 | 2 |
| 18 | 2 | 0.6 | 1 |
| 19 | 2 | 0.3 | 2 |
| 20 | 1 | 0.5 | 1 |
| 21 | 11 | 1 | 6 |
| 22 | 4 | 0.7 | 7 |
| 23 | 5 | 1 | 8 |
| 24 | 6 | 1 | 17 |
| 25 | 2 | 0.6 | 22 |
| 26 | 30 | 4 | 26 |
| 27 | 3 | 0.7 | 19 |
| 28 | 3 | 0.8 | 5 |
| 29 | 10 | 4 | 27 |
| 30 | 2 | 0.6 | 4 |
| 31 | 2 | 0.4 | 1 |
| 32 | 4 | 0.6 | 2 |
| 33 | 2 | 0.6 | 6 |
| 34 | 4 | 0.2 | 2 |
| 35 | 2 | 2 | 7 |
| 36 | 2 | 0.5 | 2 |
| 37 | 7 | 1 | 2 |
| 38 | 6 | 2 | 4 |
| 39 | 3 | 0.8 | 11 |
| 40 | 2 | 0.8 | 4 |
| 41 | 3 | 1 | 8 |
| 42 | 1 | 1 | 13 |
| 43 | 1 | 0.7 | 4 |
| 44 | 140 | 74 | 970 |
| 45 | 3 | 1 | 4 |
| 46 | 4 | 3 | 10 |
| 47 | 12 | 4 | 10 |
| 48 | 5 | 2 | 13 |
| 49 | 14 | 10 | 35 |
| 50 | 9 | 3 | 15 |
| 51 | 3 | 2 | 36 |
| 52 | 11 | 1 | 11 |
| 53 | 3 | 0.5 | 2 |
| 54 | 2 | 2 | 7 |
| 55 | 33 | 12 | 170 |
| 56 | 8 | 7 | 43 |
| 57 | 2 | 2 | 19 |
| 58 | 7 | 2 | 66 |
| 59 | 4 | 3 | 29 |
| 60 | 16 | 7 | 110 |
| 61 | 8 | 10 | 58 |
| 62 | 7 | 1 | 4 |
| 63 | 9 | 3 | 127 |
| 64 | 4 | 3 | 28 |
| 65 | 9 | 2 | 38 |
| 66 | 4 | 0.3 | 10 |
| 67 | 23 | 5 | 139 |
| 68 | 6 | 1 | 48 |
| 69 | 11 | 3 | 37 |
| 70 | 8 | 3 | 28 |
| 71 | 26 | 2 | 35 |
| 72 | 6 | 1 | 6 |
| 73 | 27 | 2 | 13 |
| 74 | 4 | 1 | 3 |
| 75 | 26 | 4 | 29 |
| 76 | 5 | 1 | 9 |
| 77 | 23 | 2 | 3 |
| 78 | 1 | 0.5 | 2 |
| 79 | 6 | 1 | 2 |
| 80 | 4 | 1 | 2 |
| 81 | 2 | 1 | 3 |
| 82 | 8 | 2 | 9 |
| 83 | 4 | 2 | 32 |
| 84 | 5 | 1 | 2 |
| 85 | 4 | 1 | 1 |
| 86 | 1 | 3 | 1 |
| 87 | 3 | 1 | 10 |
| 88 | 4 | 1 | 14 |
| 89 | 3 | 1 | 5 |
| 90 | 4 | 1 | 14 |
| 91 | 5 | 2 | 114 |
| 92 | 4 | 1 | 12 |
| 93 | 6 | 3 | 23 |
| 94 | 7 | 1 | 7 |
| 95 | 7 | 3 | 3 |
| 96 | 2 | 1 | 6 |
| 97 | 1 | 1 | 2 |
| 98 | 5 | 2 | 3 |
| 99 | 7 | 9 | 2 |
| 100 | 2 | 2 | 0.5 |
| 101 | 1 | 1 | 2 |
| 102 | 5 | 2 | 1 |
| 103 | 1 | 1 | 1 |
| 104 | 1 | 3 | 4 |
| 105 | 5 | 5 | 2 |
| 106 | 1 | 1 | 1 |

It can be seen from Table 1 that the compounds of formula (I) are potent inhibitors of JAK1, JAK2 and JAK3 kinases. Preferred compounds of the invention possess an IC$_{50}$ value for the inhibition of JAK1, JAK2 and JAK3 kinases (determined as defined above) of less than 1 µM (1000 nM), preferably of less than 0.5 µM (500 nM), more preferably of less than 0.2 µM (200 nM) for each Janus Kinase.

The compounds of this invention have been shown to display an improved profile in the Ames genotoxicity screen.

The invention is also directed to a compound of the invention as described herein for use in the treatment of the human or animal body by therapy. Compounds of the invention intended for pharmaceutical use may be administered as crystalline or amorphous products, or mixtures thereof. They may be obtained, for example, as solid plugs, powders, or films by methods such as precipitation, crystallization, freeze drying, spray drying, or evaporative drying. Microwave or radio frequency drying may be used for this purpose.

Combinations

The 2-(pyrazolopyridin-3-yl)pyrimidine derivatives of the present invention may also be combined with other active compounds in the treatment of a pathological condition or disease susceptible to amelioration by inhibition of Janus Kinases.

The combinations of the invention can optionally comprise one or more additional active substances which are known to be useful in the treatment of dermatological diseases, a respiratory diseases, allergic diseases, inflammatory or autoimmune-mediated diseases, function disorders, neurological disorders, cardiovascular diseases, viral infections, metabolism/endocrine function disorders, neurological disorders, pain, bone marrow and organ transplant rejections, myelo-dysplastic syndromes, myeloproliferative disorder (MPDs), cancer, hematologic malignancies, leukemia, lymphoma and solid tumors; more in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca, such as a) Corticoids and glucocorticoids, such as beclomethasone, betamethasone, betamethasone dipropionate, budesonide, dexamethasone, fluticasone furoate, fluticasone propionate, hydrocortisone, methylprednisolone, mometasone furoate, prednicarbate, prednisolone or prednisone;

b) Dyhydrofolate reductase inhibitors, such as methotrexate or pralatrexate;

c) Dihydroorotate dehydrogenase (DHODH) inhibitors such as leflunomide, teriflunomide or ASLAN-003 or LAS186323;

d) Purine antagonists, such as azathioprine, mercaptopurine or tioguanine;

e) Antimalarials, such as hydroxichloroquine, chloroquine or quinacrine;

f) Calcineurin inhibitors, such as cyclosporine A, tacrolimus, pimecrolimus or voclosporin;

g) Inosine-monophosphate dehydrogenase (IMPDH) inhibitors, such as mycophenolate mophetyl, ribavirin or mizoribine;

h) Fumaric acid esters, such as dimethyl fumarate;

i) Vitamine D3 derivatives such as calcipotriol, calcitriol or tacalcitol;

j) Retinoids, such as tazarotene, alitretinoin, acitretin or isotretinoin;

k) Anti-tumor necrosis factor-alpha (Anti-TNF-alpha) monoclonal antibodies, such as infliximab, adalimumab, certolizumab pegol or golimumab;

l) Soluble Tumor necrosis factor-alpha (TNF-alpha) receptors such as etanercept or CC-11050;

m) Anti-Interleukin 6 Receptor (IL-6R) antibody, such as tocilizumab, sarilumab, SA-237 or ALX-0061;

n) Anti-Interleukin 12 Receptor (IL-12R)/Interleukin 23 Receptor (IL-23R) antibody, such as ustekinumab;

o) Anti-Interleukin 17 Receptor (IL-17R) antibody, such as brodalumab;

p) Anti-CD20 (B lymphocyte protein) antibody, such as rituximab, ofatumumab, obinutuzumab, ocrelizumab, ublituximab, veltuzumab, ocaratuzumab;

q) Anti-Interleukin 5 (IL-5) antibody, such as mepolizumab;

r) Anti-Interleukin 5 Receptor (IL-5R) antibody, such as benralizumab;

s) Anti-Interleukin 13 (IL-13) antibody, such as lebrikizumab or tralokinumab;

t) Anti-Interleukin 4 Receptor (IL-4R)/Interleukin 13 Receptor (IL-13R) antibody, such as dupilumab;

u) Anti-Interleukin 17 (IL-17) antibody, such as secukinumab, ixekizumab or bimekizumab;

v) Anti-Interleukin 1 Receptor (IL-1R) antibody w) Anti-Inmunoglobuline E (IgE) antibody, such as omalizumab or quilizumab;

x) Anti-B-cell activating factor (BAFF), such as belimumab or atacicept;

y) Anti-CD19 (B lymphocyte protein) monoclonal antibody, such as blinatumomab, MEDI-551 or MOR-208;

z) Kappa opioid agonists, such as nalfurafine, nalbuphine, asimadoline or CR-845;

aa) Neurokinin receptor 1 antagonists, such as aprepitant, fosaprepitant, rolapitant, orvepitant, tradipitant or serlopitant;

bb) Dihydropteroate synthase inhibitors, such as dapsone or sulfadoxine;

cc) Histamine 1 (H1) receptor antagonists, such as azelastine, ebastine, desloratadine, promethazine, mizolastine or cetirizine;

dd) Cysteinyl leukotriene (CysLT) receptor antagonists, such as montelukast, zafirlukast, tipelukast, masilukast;

ee) Chemoattractant receptor homologous molecule expressed on TH2 cells (CRTH2) inhibitors, such as OC-459, AZD-1981, ADC-3680, ARRY-502 or setipripant; or ff) Topical anti-septics, such as triclosan, chlorhexidine, crystal violet 0.3% or sodium hypochlorite water-baths.

The compounds of formula (I) and the combinations of the invention may be used in the treatment of dermatological diseases, a respiratory diseases, allergic diseases, inflammatory or autoimmune-mediated diseases, function disorders, neurological disorders, cardiovascular diseases, viral infections, metabolism/endocrine function disorders, neurological disorders, pain, bone marrow and organ transplant rejections, myelo-dysplastic syndromes, myeloproliferative disorder (MPDs), cancer, hematologic malignancies, leukemia, lymphoma and solid tumors; more in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca; preferably in the treatment of atopic dermatitis, psoriasis, chronic hand eczema, cutaneous lupus, alopecia areata and vitiligo.

In a preferred embodiment the compounds of formula (I) and the combinations of the invention may be used in the treatment of dermatological diseases.

The active compounds in the combination product may be administered together in the same pharmaceutical composition or in different compositions intended for separate, simultaneous, concomitant or sequential administration by the same or a different route.

It is contemplated that all active agents would be administered at the same time, or very close in time. Alternatively, one or two actives could be administered in the morning and the other (s) later in the day. Or in another scenario, one or two actives could be administered twice daily and the other (s) once daily, either at the same time as one of the twice-a-day dosing occurred, or separately. Preferably at least two, and more preferably all, of the actives would be administered together at the same time. Preferably, at least two, and more preferably all actives would be administered as an admixture.

The invention is also directed to a combination product of the 2-(pyrazolopyridin-3-yl)pyrimidine derivatives of the invention together with one or more other therapeutic agents for use in the treatment of a pathological condition or disease susceptible to amelioration by inhibition of Janus Kinases (JAK), in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca; preferably in the treatment of atopic dermatitis, psoriasis, chronic hand eczema, cutaneous lupus, alopecia areata and vitiligo.

The invention also encompasses the use of a combination of the compounds of the invention together with one or more other therapeutic agents for the manufacture of a formulation or medicament for treating these diseases.

The invention also provides a method of treatment of a pathological condition or disease susceptible to amelioration by inhibition of Janus Kinases (JAK), in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca; preferably in the treatment of atopic dermatitis, psoriasis, chronic hand eczema, cutaneous lupus, alopecia areata and vitiligo, comprising administering a therapeutically effective amount of a combination of the 2-(pyrazolopyridin-3-yl)pyrimidine derivatives of the invention together with one or more other therapeutic agents.

The active compounds in the combinations of the invention may be administered by any suitable route, depending on the nature of the disorder to be treated, e.g. orally (as syrups, tablets, capsules, lozenges, controlled-release preparations, fast-dissolving preparations, etc.); topically (as creams, ointments, lotions, nasal sprays or aerosols, etc.) or by injection (subcutaneous, intradermic, intramuscular, intravenous, etc.).

The active compounds in the combination, i.e. the 2-(pyrazolopyridin-3-yl)pyrimidine derivatives of the invention, and the other optional active compounds may be administered together in the same pharmaceutical composition or in different compositions intended for separate, simultaneous, concomitant or sequential administration by the same or a different route.

One execution of the present invention consists of a kit of parts comprising a 2-(pyrazolopyridin-3-yl)pyrimidine derivative of the invention together with instructions for simultaneous, concurrent, separate or sequential use in combination with another active compound useful in the treatment of atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca; preferably in the treatment of atopic dermatitis, psoriasis, chronic hand eczema, cutaneous lupus, alopecia areata and vitiligo.

Another execution of the present invention consists of a package comprising a 2-(pyrazolopyridin-3-yl)pyrimidine derivative of the invention and another active compound useful in the treatment of atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca; preferably in the treatment of atopic dermatitis, psoriasis, chronic hand eczema, cutaneous lupus, alopecia areata and vitiligo.

Pharmaceutical Compositions

Pharmaceutical compositions according to the present invention comprise the 2-(pyrazolopyridin-3-yl)pyrimidine derivatives of the invention in association with a pharmaceutically acceptable diluent or carrier.

As used herein, the term pharmaceutical composition refers to a mixture of one or more of the 2-(pyrazolopyridin-3-yl)pyrimidine derivatives described herein, or physiologically/pharmaceutically acceptable salts, solvates, N-oxides, stereoisomers, deuterated derivatives thereof or prodrugs thereof, with other chemical components, such as physiologically/pharmaceutically acceptable carriers and excipients. The purpose of a pharmaceutical composition is to facilitate administration of a compound to an organism.

As used herein, a physiologically/pharmaceutically acceptable diluent or carrier refers to a carrier or diluent that does not cause significant irritation to an organism and does not abrogate the biological activity and properties of the administered compound.

The invention further provides pharmaceutical compositions comprising the 2-(pyrazolopyridin-3-yl)pyrimidine derivatives of the invention in association with a pharmaceutically acceptable diluent or carrier together with one or more other therapeutic agents for use in the treatment of a pathological condition or disease susceptible to amelioration by inhibition of Janus Kinases (JAK), such as the ones previously described.

The invention is also directed to pharmaceutical compositions of the invention for use in the treatment of a pathological condition or disease susceptible to amelioration by inhibition of Janus Kinases (JAK), in particular atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca; preferably in the treatment of atopic dermatitis, psoriasis, chronic hand eczema, cutaneous lupus, alopecia areata and vitiligo.

The invention also encompasses the use of a pharmaceutical composition of the invention for the manufacture of a medicament for treating these diseases.

The invention also provides a method of treatment of a pathological condition or disease susceptible to amelioration by inhibition of Janus Kinases (JAK), in particular wherein the pathological condition or disease is selected from atopic dermatitis, psoriasis, contact dermatitis, eczema, chronic hand eczema, basal cell carcinoma, squamous cell carcinoma, actinic keratosis, melanoma, vitiligo, alopecia areata, cutaneous lupus erythematosus, cutaneous vasculitits, dermatomyositis, cutaneous T-cell lymphoma, Széry syndrome, pyoderma gangrenosum, lichen planus, blistering diseases including but not limited to pemphigus vulgaris, bullous pemphigoid and epidermolysis bullosa, leukemia, lymphomas and solid tumors, rheumatoid arthritis, multiple sclerosis, amyotrophic lateral sclerosis, systemic lupus erythematosis, autoimmune hemolytic anemia, type I diabetes, asthma, chronic obstructive pulmonary disease (COPD), cystic fibrosis, bronchiectasis, cough, idiopathic pulmonary fibrosis, sarcoidosis, allergic rhinitis, inflammatory bowel disease, ulcerative colitis, Crohn's disease, dry eye, uveitis, allergic conjunctivitis and keratoconjuntivitis sicca; preferably in the treatment of atopic dermatitis, psoriasis, chronic hand eczema, cutaneous lupus, alopecia areata and vitiligo, comprising administering a therapeutically effective amount of a pharmaceutical composition of the invention.

The present invention also provides pharmaceutical compositions which comprise, as an active ingredient, at least a 2-(pyrazolopyridin-3-yl)pyrimidine derivative which is a compound of formula (I) or a pharmaceutically acceptable salt, or solvate, or N-oxide, or stereoisomer or deuterated derivative thereof in association with a pharmaceutically acceptable excipient such as a carrier or diluent. Preferably the compositions are made up in a form suitable for oral, topical, nasal, rectal, percutaneous or injectable administration. The compounds of the present invention show physicochemical properties (such as solubility water and in a range of lipophilic and hydrophilic solvents, melting point and stability), which make them specially suitable for topical administration.

In a preferred embodiment, the compositions are made up in a form suitable for topical administration.

Pharmaceutical compositions suitable for the delivery of 2-(pyrazolopyridin-3-yl)pyrimidine derivatives of the invention and methods for their preparation will be readily apparent to those skilled in the art. Such compositions and methods for their preparation can be found, for example, in Remington: The Science and Practice of Pharmacy, 21st Edition, Lippincott Williams & Wilkins, Philadelphia, Pa., 2001.

i) Topical Administration

The 2-(pyrazolopyridin-3-yl)pyrimidine derivatives of the invention may be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibers, bandages and microemulsions. Other means of topical administration include delivery by electroporation, iontophoresis, phonophoresis, sonophoresis and microneedle or needle-free injection.

Formulations for topical administration may be formulated to be immediate and/or modified release. Modified release formulations include delayed-, sustained-, pulsed-, controlled-, targeted and programmed release.

ii) Oral Administration

The 2-(pyrazolopyridin-3-yl)pyrimidine derivatives of the invention may be administered orally (peroral administration; per os (latin)). Oral administration involve swallowing, so that the compound is absorbed from the gut and delivered to the liver via the portal circulation (hepatic first pass metabolism) and finally enters the gastrointestinal (GI) tract.

Compositions for oral administration may take the form of tablets, retard tablets, sublingual tablets, capsules, inhalation aerosols, inhalation solutions, dry powder inhalation, or liquid preparations, such as mixtures, solutions, elixirs, syrups or suspensions, all containing the compound of the invention; such preparations may be made by methods well-known in the art. The active ingredient may also be presented as a bolus, electuary or paste.

iii) Oral Mucosal Administration

The 2-(pyrazolopyridin-3-yl)pyrimidine derivatives of the invention can also be administered via the oral mucosal. Within the oral mucosal cavity, delivery of drugs is classified into three categories: (a) sublingual delivery, which is systemic delivery of drugs through the mucosal membranes lining the floor of the mouth, (b) buccal delivery, which is drug administration through the mucosal membranes lining the cheeks (buccal mucosa), and (c) local delivery, which is drug delivery into the oral cavity.

Pharmaceutical products to be administered via the oral mucosal can be designed using mucoadhesive, quick dissolve tablets and solid lozenge formulations, which are formulated with one or more mucoadhesive (bioadhesive) polymers and/or oral mucosal permeation enhancers.

iv) Inhaled Administration

The 2-(pyrazolopyridin-3-yl)pyrimidine derivatives of the invention can also be administered by inhalation, typically in the form of a dry powder from a dry powder inhaler or as an aerosol spray from a pressurized container, pump, spray, atomizer (preferably an atomizer using electrohydrodynamics to produce a fine mist), or nebulizer, with or without the use of a suitable propellant.

v) Nasal Mucosal Administration

The 2-(pyrazolopyridin-3-yl)pyrimidine derivatives of the invention may also be administered via the nasal mucosal.

Typical compositions for nasal mucosa administration are typically applied by a metering, atomizing spray pump and are in the form of a solution or suspension in an inert vehicle such as water optionally in combination with conventional excipients such as buffers, anti-microbials, tonicity modifying agents and viscosity modifying agents.

vi) Parenteral Administration

The 2-(pyrazolopyridin-3-yl)pyrimidine derivatives of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilization, may readily be accomplished using standard pharmaceutical techniques well known to those skilled in the art. The solubility of compounds of the invention used in the preparation of parenteral solutions may be increased by the use of appropriate formulation techniques, such as the incorporation of solubility-enhancing agents.

vii) Rectal/Intravaginal Administration 2-(pyrazolopyridin-3-yl)pyrimidine derivatives of the invention may be administered rectally or vaginally, for example, in the form of a suppository, pessary, or enema. Cocoa butter is a traditional suppository base, but various alternatives may be used as appropriate. Formulations for rectal/vaginal administration may be formulated to be immediate and/or modified release. Modified release formulations include delayed-, sustained-, pulsed-, controlled-, targeted and programmed release.

viii) Ocular Administration 2-(pyrazolopyridin-3-yl)pyrimidine derivatives of the invention may also be administered directly to the eye or ear, typically in the form of drops of a micronized suspension or solution in isotonic, pH-adjusted, sterile saline. Other formulations suitable for ocular and aural administration include ointments, biodegradable {e.g. absorbable gel sponges, collagen) and nonbiodegradable (e.g. silicone) implants, wafers, lenses and particulate or vesicular systems, such as niosomes or liposomes. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The amount of the active 2-(pyrazolopyridin-3-yl)pyrimidine derivative administered will be dependent on the subject being treated, the severity of the disorder or condition, the rate of administration, the disposition of the compound and the discretion of the prescribing physician. However, an effective dosage is typically in the range of 0.01-3000 mg, more preferably 0.5-1000 mg of active ingredient or the equivalent amount of a pharmaceutically acceptable salt thereof per day. Daily dosage may be administered in one or more treatments, preferably from 1 to 4 treatments, per day.

Preferably, the the pharmaceutical compositions of the invention are made up in a form suitable for oral or topical administration, being particularly preferred topical administration.

The amount of each active which is required to achieve a therapeutic effect will, of course, vary with the particular active, the route of administration, the subject under treatment, and the particular disorder or disease being treated.

The following preparations forms are cited as formulation examples:

FORMULATION EXAMPLES

Formulation Example 1

Oral Suspension

| Ingredient | Amount |
| --- | --- |
| Active Compound | 3 mg |
| Citric acid | 0.5 g |
| Sodium chloride | 2.0 g |
| Methyl paraben | 0.1 g |
| Granulated sugar | 25 g |
| Sorbitol (70% solution) | 11 g |
| Veegum K | 1.0 g |
| Flavoring | 0.02 g |
| Dye | 0.5 mg |
| Distilled water | q.s. to 100 mL |

Formulation Example 2

Hard Gelatine Capsule for Oral Administration

| Ingredient | Amount |
| --- | --- |
| Active Compound | 1 mg |
| Lactose | 150 mg |
| Magnesium stearate | 3 mg |

Formulation Example 3

O/W Emulsion

| Ingredient | Amount |
| --- | --- |
| Active compound | 1% |
| Cetyl alcohol | 3% |
| Stearyl alcohol | 4% |
| Gliceryl monostearate | 4% |
| Sorbitan monostearate | 0.8% |
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

Formulation Example 4

O/W Emulsion

| Ingredient | Amount |
| --- | --- |
| Active compound | 1% |
| Caprylic/Carpic Triglyceride | 5% |
| Cetyl alcohol | 7% |
| Gliceryl monostearate | 3.5% |
| Sorbitan monostearate | 0.8% |
| Sorbitan monostearate POE | 0.7% |
| White petrolatum | 10% |
| Stearoxytrimethysilane | 5% |
| EDTA | 0.1% |
| Methylparaben | 0.18% |
| Propylparaben | 0.02% |
| Glycerine | 20% |
| Purified water csp. | 100% |

Formulation Example 5

O/W Emulsion

| Ingredient | Amount |
| --- | --- |
| Active compound | 1% |
| Octyldodecanol | 5% |
| Cetyl alcohol | 4% |
| Gliceryl monostearate | 6% |
| Ceteareth-12 | 1.5% |
| Ceteareth-20 | 1.5% |
| Sorbitan monostearate POE | 0.7% |
| White petrolatum | 3% |
| Dimethicole | 1.5% |
| Benzyl alcohol | 2% |
| Glycerine | 20% |
| Propilenglycol | 10% |
| Purified water csp. | 100% |

Modifications, which do not affect, alter, change or modify the essential aspects of the 2-(pyrazolopyridin-3-yl)pyrimidine derivatives, combinations or pharmaceutical compositions described, are included within the scope of the present invention.

The invention claimed is:

1. A 2-(pyrazolopyridin-3-yl)pyrimidine derivative, wherein the 2-(pyrazolopyridin-3-yl)pyrimidine derivative is a compound of formula (I), or a pharmaceutically acceptable salt, solvate, N-oxide, stereoisomer, or deuterated derivative thereof:

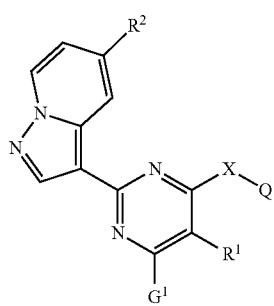

Formula (I)

wherein:
X is a —$NR^3$— group;
$R^1$ and $R^2$ are independently chosen from a hydrogen atom, a halogen atom, a linear or branched $C_{1-4}$ alkyl group, a linear or branched $C_{1-4}$ alkoxy group, and a —CN group;
$R^3$ is chosen from a hydrogen atom, a linear or branched $C_{1-4}$ alkyl group, a —$(CH_2)_{1-3}NR'R''$ group, and a —$(CH_2)_{1-3}$-pyrrolidine group;
$G^1$ is a —O—$R^6$ group;
Q is chosen from Qa, Qb, or Qc:

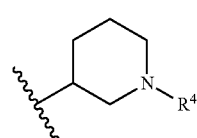

Qa

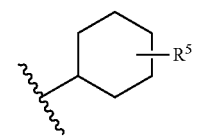

Qb

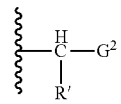

Qc wherein:
$R^4$ is chosen from a —$CO(CH_2)_{1-2}$—OH group and a —$CO(CH_2)_{1-2}$—CN group,
$R^5$ is chosen from a —$(CH_2)_m$—CN group and a —$(CH_2)_m$—OH group;
$G^2$ is chosen from a phenyl group, a pyrimidine group, and a pyridine group, wherein the phenyl, pyrimidine and pyridine groups are unsubstituted or substituted by one or more substituents chosen from a halogen atom, a linear or branched $C_{1-4}$ alkyl group, a hydroxyl group, and a —CN group,
$R^6$ is chosen from a linear or branched ($C_{1-6}$ alkoxy)-($C_{1-6}$ alkyl) group and a linear or branched $C_{1-6}$ alkyl group, wherein the linear or branched $C_{1-6}$ alkyl group is unsubstituted or substituted with one or more substituents chosen from a halogen atom and a hydroxyl group, and
m is independently 0, 1, 2, or 3.

2. The compound according to claim 1, wherein $R^1$ is chosen from a hydrogen atom, a fluorine atom, a chlorine atom, and a methyl group.

3. The compound according to claim 1, wherein $R^2$ is chosen from a hydrogen atom and a fluorine atom.

4. The compound according to claim 1, wherein $R^3$ is a hydrogen atom.

5. The compound according to claim 1, wherein Q is Qa.

6. The compound according to claim 1, wherein:
$R^1$ is chosen from a hydrogen atom, a fluorine atom, a chlorine atom, and a methyl group;
$R^2$ is chosen from a hydrogen atom and a fluorine atom;
X is a —$NR^3$— group;
$R^3$ is a hydrogen atom;
Q is Qa;
$R^4$ is chosen from a —$CO(CH_2)_{1-2}$—OH group and a —$CO(CH_2)_{1-2}$—CN group;
$G^1$ is a —O—$R^6$ group;

R⁶ is chosen from a linear or branched ($C_{1-6}$ alkoxy)-($C_{1-6}$ alkyl) group and a linear or branched $C_{1-6}$ alkyl group, wherein the linear or branched $C_{1-6}$ alkyl group is unsubstituted or substituted with one or more substituents chosen from a halogen atom and a hydroxyl group.

7. The compound according to claim 1, wherein:
X is a —NR³— group;
R¹ and R² are independently chosen from a hydrogen atom, a fluorine atom, and a methyl group;
R³ is chosen from a hydrogen atom and a methyl group;
G¹ is a —O—R⁶ group;
R⁴ is chosen from a —CO(CH₂)—OH group, a —CO(CH₂)—CN group;
R⁵ is a —CH₂—CN group;
G² is chosen from a pyrimidine group and a pyridine group, wherein the pyrimidine and pyridine groups are unsubstituted or substituted by a fluorine atom; and
R⁶ is chosen from a —(CH₂)₂OCH₃ group, a —(CH₂)₂OCH₂CH₃ group, a —CH(CH₃)CH₂OCH₃ group, a methyl group, an ethyl group, a butyl group, a —CH₂CF₃ group, a —CH₂CHF₂ group, a CH(CH₃)₂ group, a —(CH₂)₂₋₃OH group, a —CH(CH₃)—CH₂OH group, and a —CH₂CH(OH)CH₂OH group.

8. The compound according to claim 1, wherein the compound is chosen from:
(Trans-4-{[5-fluoro-6-(2-hydroxyethoxy)-2-pyrazolo[1,5-a]pyridin-3-ylpyrimidin-4-yl]amino}cyclohexyl)acetonitrile;
{Trans-4-[(6-{[(2S)-2,3-dihydroxypropyl]oxy}-5-fluoro-2-pyrazolo[1,5-a]pyridin-3-ylpyrimidin-4-yl)amino]cyclohexyl}acetonitrile;
{Trans-4-[(6-{[(2R)-2,3-dihydroxypropyl]oxy}-5-fluoro-2-pyrazolo[1,5-a]pyridin-3-ylpyrimidin-4-yl)amino]cyclohexyl}acetonitrile;
2-[(5-Fluoro-6-{[(1 S)-1-(5-fluoropyrimidin-2-yl)ethyl]amino}-2-pyrazolo[1,5-a]pyridin-3-ylpyrimidin-4-yl)oxy]etanol;
(2S)-3-[(5-fluoro-6-{[(1 S)-1-(5-fluoropyrimidin-2-yl)ethyl]amino}-2-pyrazolo[1,5-a]pyridin-3-ylpyrimidin-4-yl)oxy]propane-1,2-diol;
3-((3R)-3-{[5-fluoro-6-(2-hydroxyethoxy)-2-pyrazolo[1,5-a]pyridin-3-ylpyrimidin-4-yl]amino}piperidin-1-yl)-3-oxopropanenitrile;
3-{(3R)-3-[(6-butoxy-5-fluoro-2-pyrazolo[1,5-a]pyridin-3-ylpyrimidin-4-yl)amino]piperidin-1-yl}-3-oxopropanenitrile;
2-((3R)-3-{[6-(2-Methoxyethoxy)-5-methyl-2-pyrazolo[1,5-a]pyridin-3-ylpyrimidin-4-yl]amino}piperidin-1-yl)-2-oxoethanol;
2-((3R)-3-{[5-Fluor-6-(2-methoxyethoxy)-2-pyrazolo[1,5-a]pyridin-3-ylpyrimidin-4-yl]amino}piperidin-1-yl)-2-oxoethanol;
2-((3R)-3-{[5-Fluor-6-(2-hydoxyethoxy)-2-pyrazolo[1,5-a]pyridin-3-ylpyrimidin-4-yl]amino}pieridin-1-yl)-2-oxoethanol;
3-[(5-Fluoro-6-{[(3R)-1-glycoloylpiperidin-3-yl]amino}-2-pyrazolo[1,5-a]pyridin-3-ylpyrimidin-4-yl)oxy]propan-1-ol;
2-((3R)-3-{[5-Fluoro-6-methoxy-2-pyrazolo[1,5-a]pyridin-3-ylpyrimidin-4-yl)amino]piperidin-1-yl}-2-oxoethanol;
2-{(3R)-3-[(6-Ethoxy-5-fluoro-2-pyrazoa[1,5-a]pyridin-3-ylpyrimidin-4-yl)amino]piperidin-1-yl}-2-oxoethanol;
2-((3R)-3-{[5-Fluoro-2-pyrazolo[1,5-a]pyridin-3-yl-6-(2,2-trifluoroethoxy)pyrimidin-4-yl]amino}piperidin-1-yl)-2-oxoethanol;
2-((3R)-3-{[6-(2,2-Difluoroethoxy)-5-fluoro-2-pyrazolo[1,5-a]pyridin-3-ylpyrimidin-4-yl]amino}piperidin-1-yl)-2-oxoethanol;
2-{(3R)-3-[(5-Fluoro-6-isopropoxy-2-pyrazolo[1,5-a]pyridin-3-ylpyrimidin-4-yl)amino]piperidin-1-yl}-2-oxoethanol;
2-[(3R)-3-({5-Fluoro-6-[(1 S)-2-methoxy-1-methylethoxy]-2-pyrazolo[1,5-a]pyridin-3-ylpyrimidin-4-yl}amino)piperidin-1-yl]-2-oxoethanol;
(2S)-2-[(5-Fluoro-6-{[(3R)-1-glycoloylpiperidin-3-yl]amino}-2-pyrazolo[1,5-a]pyridin-3-ylpyrimidin-4-yl)oxy]propan-1-ol;
2-[(3R)-3-({5-Fluoro-6-[(1R)-2-methoxy-1-methylethoxy]-2-pyrazolo[1,5-a]pyridin-3-ylpyrimidin-4-yl}amino)piperidin-1-yl]-2-oxoethanol;
(2R)-2-[(5-Fluoro-6-{[(3R)-1-glycoloylpiperidin-3-yl]amino}-2-pyrazolo[1,5-a]pyridin-3-ylpyrimidin-4-yl)oxy]propan-1-ol;
2-((3R)-3-{[6-(2-Ethoxyethoxy)-5-fluoro-2-pyrazolo[1,5-a]pyridin-3-ylpyrimidin-4-yl]amino}piperidin-1-yl)-2-oxoethanol;
(2S)-1-[(5-Fluoro-6-{[(3R)-1-glycoloylpiperidin-3-yl]oxy}-2-pyrazolo[1,5-a]pyridin-3-ylpyrimidin-4-yl)oxy]propan-2-ol;
2-{(3R)-3-[(6-Methoxy-5-methyl-2-pyrazolo[1,5-a]pyridin-3-ylpyrimidin-4-yl)amino]piperidin-1-yl}-2-oxoethanol;
2-{(3R)-3-[(6-Methoxy-2-pyrazolo[1,5-a]pyridin-3-ylpyrimidin-4-yl)amino]piperidin-1-yl)-2-oxoethanol;
3-((3R)-3-[(6-Methoxy-2-pyrazolo[1,5-a]pyridin-3-ylpyrimidin-4-yl)amino]piperidin-1-yl}-3-oxopropanenitrile;
2-((3R)-3-{[6-(2-Methoxyethoxy)-2-pyrazolo[1,5-a]pyridin-3-ylpyrimidin-4-yl]amino}piperidin-1-yl)-2-oxoethanol;
3-((3R)-3-{[6-(2-Methoxyethoxy)-2-pyrazolo[1,5-a]pyridin-3-ylpyrimidin-4-yl]amino}piperidin-1-yl)-3-oxopropanenitrile;
3-((3R)-3-([6-(2-Hydroxyethoxy)-2-pyrazolo[1,5a]pyridin-3-ylpyrimidin-4-yl]amino)piperidin-1-yl)-3-oxopropanenitrile;
a pharmaceutically acceptable salt, N-oxide, solvate, stereoisomer or deuterated derivative thereof.

9. A 2-(pyrazolopyridin-3-yl)pyrimidine derivative according to claim 1 which is 3-[(5-Fluoro-6-{[(3R)-1-glycoloylpiperidin-3-yl]amino}-2-pyrazolo[1,5-a]pyridin-3-ylpyrimidin-4-yl)oxy]propan-1-ol, or a pharmaceutically acceptable salt, N-oxide, solvate, stereoisomer or deuterated derivative thereof.

10. A 2-(pyrazolopyridin-3-yl)pyrimidine derivative according to claim 1 which is 2-{(3R)-3-[(5-Fluoro-6-methoxy-2-pyrazolo[1,5-a]pyridin-3-ylpyrimidin-4-yl)amino]piperidin-1-yl}-2-oxoethanol, or a pharmaceutically acceptable salt, N-oxide, solvate, stereoisomer or deuterated derivative thereof.

11. A 2-(pyrazolopyridin-3-yl)pyrimidine derivative according to claim 1 which is 3-((3R)-3-{[6-(2-Methoxyethoxy)-2-pyrazolo[1,5-a]pyridin-3-ylpyrimidin-4-yl]amino}piperidin-1-yl)-3-oxopropanenitrile, or a pharmaceutically acceptable salt, N-oxide, solvate, stereoisomer or deuterated derivative thereof.

12. A 2-(pyrazolopyridin-3-yl)pyrimidine derivative according to claim 1 which is 3-((3R)-3-{[6-(2-Hydroxyethoxy)-2-pyrazolo[1,5-a]pyridin-3-ylpyrimidin-4-yl]amino}piperidin-1-yl)-3-oxopropanenitrile, or a pharmaceutically acceptable salt, N-oxide, solvate, stereoisomer or deuterated derivative thereof.

13. A combination product comprising (i) at least one 2-(pyrazolopyridin-3-yl)pyrimidine derivative according to claim 1, and (ii) at least one additional active ingredient chosen from:
- a) Corticoids and glucocorticoids;
- b) Dihydrofolate reductase inhibitors;
- c) Dihydroorotate dehydrogenase (DHODH) inhibitors;
- d) Purine antagonists;
- e) Antimalarials;
- f) Calcineurin inhibitors;
- g) Inosine-monophosphate dehydrogenase (IMPDH) inhibitors;
- h) Fumaric acid esters;
- i) Vitamine D3 derivatives;
- j) Retinoids;
- k) Anti-tumor necrosis factor-alpha (Anti-TNF-alpha) monoclonal antibodies;
- l) Soluble Tumor necrosis factor-alpha (TNF-alpha) receptors;
- m) Anti-Interleukin 6 Receptor (IL-6R) antibody;
- n) Anti-Interleukin 12 Receptor (IL-12R)/Interleukin 23 Receptor (IL-23R) antibody;
- o) Anti-Interleukin 17 Receptor (IL-17R) antibody;
- p) Anti-CD20 (B lymphocyte protein) antibody;
- q) Anti-Interleukin 5 (IL-5) antibody;
- r) Anti-Interleukin 5 Receptor (IL-5R) antibody;
- s) Anti-Interleukin 13 (IL-13) antibody;
- t) Anti-Interleukin 4 Receptor (IL-4R)/Interleukin 13 Receptor (IL-13R) antibody;
- u) Anti-Interleukin 17 (IL-17) antibody;
- v) Anti-Interleukin 1 Receptor (IL-1R) antibody;
- w) Anti-Inmunoglobuline E (IgE) antibody;
- x) Anti-B-cell activating factor (BAFF);
- y) Anti-CD19 (B lymphocyte protein) monoclonal antibody;
- z) Kappa opioid agonists;
- aa) Neurokinin receptor 1 antagonists;
- bb) Dihydropteroate synthase inhibitors;
- cc) Histamine 1 (H1) receptor antagonists;
- dd) Cysteinyl leukotriene (CysLT) receptor antagonists;
- ee) Chemoattractant receptor homologous molecule expressed on TH2 cells (CRTH2) inhibitors; and
- ff) Topical anti-septics.

* * * * *

UNITED STATES PATENT AND TRADEMARK OFFICE
CERTIFICATE OF CORRECTION

PATENT NO. : 10,759,793 B2  
APPLICATION NO. : 15/735235  
DATED : September 1, 2020  
INVENTOR(S) : Cristina Esteve Trias et al.

Page 1 of 1

It is certified that error appears in the above-identified patent and that said Letters Patent is hereby corrected as shown below:

In the Claims

Claim 8, Column 107, Lines 50-52, "2-((3R)-3-{[5-Fluor-6-(2-methoxyethoxy)-2-pyrazolo[1,5-a]pyridin-3-ylpyrimidin-4-yl]amino}piperidin-1-yl)-2-oxoethanol;" should read as --2-((3R)-3-{[5-Fluoro-6-(2-methoxyethoxy)-2-pyrazolo[1,5-a]pyridin-3-ylpyrimidin-4-yl]amino}piperidin-1-yl)-2-oxoethanol;--.

Claim 8, Column 107, Lines 53-55, "2-((3R)-3-{[5-Fluor-6-(2-hydoxyethoxy)-2-pyrazolo[1,5-a]pyridin-3-ylpyrimidin-4-yl]amino}pieridin-1-yl)-2-oxoethanol;" should read as --2-((3R)-3-{[5-Fluoro-6-(2-hydroxyethoxy)-2-pyrazolo[1,5-a]pyridin-3-ylpyrimidin-4-yl]amino}piperidin-1-yl)-2-oxoethanol;--.

Claim 8, Column 107, Lines 62-64, "2-{(3R)-3-[(6-Ethoxy-5-fluoro-2-pyrazoa[1,5-a]pyridin-3-ylpyrimidin-4-yl)- amino]piperidin-1-yl}-2-oxoethanol;" should read as --2-{(3R)-3-[(6-Ethoxy-5-fluoro-2-pyrazolo[1,5-a]pyridin-3-ylpyrimidin-4-yl)-amino]piperidin-1-yl}-2-oxoethanol;--.

Signed and Sealed this  
Fifteenth Day of February, 2022

Drew Hirshfeld  
*Performing the Functions and Duties of the*  
*Under Secretary of Commerce for Intellectual Property and*  
*Director of the United States Patent and Trademark Office*